(12) United States Patent
Yoshida et al.

(10) Patent No.: US 6,967,097 B2
(45) Date of Patent: Nov. 22, 2005

(54) PHENYLALAININE AMMONIA LYASE POLYPEPTIDE AND POLYNUCLEOTIDE SEQUENCES AND METHODS OF OBTAINING AND USING SAME

(75) Inventors: Roberta K. Yoshida, Buffalo Grove, IL (US); Anna B. Kootstra, Island Lake, IL (US)

(73) Assignee: PCBU Services, Inc., Wilmington, DE (US)

( * ) Notice: Subject to any disclaimer, the term of this patent is extended or adjusted under 35 U.S.C. 154(b) by 595 days.

(21) Appl. No.: 09/939,408

(22) Filed: Aug. 24, 2001

(65) Prior Publication Data

US 2002/0102712 A1 Aug. 1, 2002

Related U.S. Application Data

(63) Continuation-in-part of application No. 09/624,693, filed on Jul. 24, 2000, now Pat. No. 6,355,468, which is a continuation-in-part of application No. PCT/US01/23270, filed on Jul. 24, 2001.

(51) Int. Cl.$^7$ .............................. C12N 9/88; C12N 1/20; C12N 15/00; C07H 21/04
(52) U.S. Cl. ................. 435/232; 435/252.3; 435/320.1; 536/23.2; 530/350
(58) Field of Search ............................ 435/232, 252.3, 435/320.1; 536/23.2; 530/350

(56) References Cited

U.S. PATENT DOCUMENTS

| | | | |
|---|---|---|---|
| 4,436,813 A | 3/1984 | Wood et al. ................. | 435/109 |
| 4,574,117 A | 3/1986 | Vollmer et al. ............. | 435/108 |
| 4,584,273 A | 4/1986 | Finkelman et al. ......... | 435/232 |
| 4,598,047 A | 7/1986 | McGuire ..................... | 435/108 |
| 4,600,692 A | 7/1986 | Wood et al. ................. | 435/108 |
| 4,636,466 A | 1/1987 | McGuire et al. ............ | 435/108 |
| 4,728,611 A | 3/1988 | Wood et al. ................. | 435/108 |
| 4,732,851 A | 3/1988 | Wood et al. .................. | 435/43 |
| 4,757,015 A | 7/1988 | Orndorff et al. ............ | 435/108 |
| 5,981,239 A | 11/1999 | Liu ............................. | 435/108 |

FOREIGN PATENT DOCUMENTS

| | | |
|---|---|---|
| EP | 0 167 411 | 8/1986 |
| WO | WO 88/02024 | 3/1988 |
| WO | WO 93/07279 | 4/1993 |

OTHER PUBLICATIONS

Bowie et al., 1990. Science, vo. 247, pp. 1306 1310.*
Accession No. AAP80513 (PAL) and Applicants SEQ ID NO: 21 (PAL), are 89.9% identical [EP279655–A, Aug. 24, 1988].*
Accession No. AAN81116 (DNA encoding PAL) and Applicants SEQ ID NO: 20 (DNA encoding PAL), are 67.8% identical [EP279665–A Aug. 24, 1988].*
Accession No. E01783 (DNA encoding PAL) and Applicants' SEQ ID NO: 20, are 67.8% identical [JP 1988317086–A, Sep. 29, 1997].*
Seffernick et al. [J. Bacteriol. Apr. 2001, p. 2406–2410].*
Clara M. Ambrus, et al., "Phenylalanine Depletion for the Management of Phenylketonuria: Use of Enzyme Reactors with Immobilized Enzymes," *Science*, 201:837–839, (1978).
John G. Anson, et al., "Complete nucleotide sequence of the *Rhodosporidium toruloides* gene coding for phenylalanine ammonia–lyase," *Gene*, 58:189–199 (1987).
Godwin B D'Cunha, et al., "Stabilization of phenylalanine ammonia lyase containing *Rhodotorula glutinis* cells for the continuous synthesis of L–phenylalanine methyl ester/96/," *Enzyme and Microbial Technology*, 19:421–472, 1996.
Don R. Durham, et al., "Dissimilation of Aromatic Compounds in *Rhodotorula graminis*: Biochemical Characterization of Pleiotropically Negative Mutants," *Journal of Bacteriology*, 160:771–777, (1984).
Christopher T. Evans, et al., "BioConversion of Trans–Cinnamic Acid to L–Phenylalanine in an Immobilized Whole Cell Reactor," *Biotechnology and Bioengineering*, 30:1067–1072 (1987).
James D. B. Faulkner, et al., "High–level expression of the phenylalanine ammonia lyase–encoding gene from *Rhodosporidium toruloides* in *Saccharomyces cerevisiae* and *Escherichia coli* using bifunctional expression system," *Gene*, 143(1):13–20 (1994).
David Filpula, et al., "Nucleotide sequence of gene for phenylalanine ammonia–lyase for *Rhodotorula rubra*," *Nucleic Acids Research*, 16:11381 (1988).
Andreas Gloge, et al., "Phenylalanine Ammonia–Lyase: The Use of Its Broad Substrate Specificty for Mechanistic Investigations and Biocatalysis—Synthesis of L–Arylalanines," *Chem. Eur. J.* 6:18, 3386–3390 (2000).
Daniel S. Hodgins, "Yeast Phenylalanine Ammonia–lyase, " *The Journal of Biological Chemistry*, 246 (9):2977–2983 (1971).
Katsuhiko Nakamichi, et al., "Induction and Stabilization of L–Phenylalanine Ammonia–Lyase Activity in *Rhodotorula glutinis*," *Eur. J. Appl. Microbiol Biotechnol*, 18:158–162 (1983).
Derwent Abstract 85–095789 (Abstract to JP 83–151415).
JAPIO Abstract 81–026197 (Abstract to JP 56–26197).
JAPIO Abstract 88–148992 (Abstract to JP 63–148992).
GenBank Accession Nos. x13094 and x13095.
GenBank Accession Nos. x51513.

* cited by examiner

*Primary Examiner*—Tekchand Saidha
(74) *Attorney, Agent, or Firm*—Marshall, Gerstein & Borun LLP

(57) ABSTRACT

The present provides a *Rhodotorula* phenylalanine lyase polypeptide, polynucleotides that encode the polypeptide, and methods of obtaining and using these products. In particular the polypeptide can be employed for the production of phenylalanine, phenylalanine analogs, and optically active unnatural amino acids having phenylalanine-like structures.

13 Claims, 10 Drawing Sheets

```
                              1                                              50
R.graminis         (1)   MAPSLDSLATTLANGFTNGSHAAPTKSAAGPTSALRRTPGLDGHAAHQSQ
R.mucilaginosa     (1)   MAPSVDSIATSVANSLSNGLHAAAAANGG-DVHKKTAGAGSLLPTTETTQ
R.toruloides       (1)   MAPSLDSISHSFANGVASAKQAVNGAS------TNLAVAGSHLPTTQVTQ
Consensus          (1)   MAPSLDSIATSXANGXXNGXHAAXXASXXXXXXXXXXAXAGSXLPTTXXTQ 51                                            100
R.graminis        (51)   LEIVQELLSDP-TDDVVELSGYSLTVFDVVGAARKGRRVRVQNDDEIRAR
R.mucilaginosa    (50)   LDIVERILADAGATDQ1KLDGYTLTLGDVVGAARRGRSVKVADSPHIREK
R.toruloides      (45)   VDIVEKMLAAP-TDSTLELDGYSLNLGDVVSAARKGRPVRVKDSDEIRSK
Consensus         (51)   LDIVEXXLADPXTDDXXELDGYSLTLGDVVGAARKGRXVRVXDSDEIRXK 101                                           150
R.graminis       (100)   VDKSVDFLKAQLQNSVYGVTTGFGGSADTRTEDAVSLQKALIEHQLCGVT
R.mucilaginosa   (100)   IDASVEFLRIQLDNSVYGVTTGFGGSADTRTEDAISLQKALLEHQLCGVL
R.toruloides      (94)   IDKSVEFLRSQLSMSVYGVTTGFGGSADTRTEDAISLQKALLEHQLCGVL
Consensus        (101)   IDKSVEFLRXQLXNSVYGVTTGFGGSADTRTEDAISLQKALLEHQLCGVL 151                                           200
R.graminis       (150)   PTSVSSFSVGRGLENTLPLEVVRGAMVIRVNSLTRGHSAVRLVVLEALTN
R.mucilaginosa   (150)   FTSMDGFALGRGLENSLPLEVVRGAMTIRVNSLTRGHSAVRIVVLEALTN
R.toruloides     (144)   FSSFDSFRLGRGLENSLPLEVVRGAMTIRVNSLTRGHSAVRLVVLEALTN
Consensus        (151)   PTSXDSFXLGRGLENSLPLEVVRGAMTIRVNSLTRGHSAVRLVVLEALTN 201                                           250
R.graminis       (200)   FLNHRITPIVPLRGSISASGDLSPLSYIAGAITGHPDVKVHVLHEGTEKT
R.mucilaginosa   (200)   FLNHGITPIVPLRGTISASGDLSPLSYIAASITGHPDSKVEVDG----KT
R.toruloides     (194)   FLNHGITPIVPLRGTISASGDLSPLSYIAAAISGHPDSKVIVVHEGKEKI
Consensus        (201)   FLNHGITPIVPLRGTISASGDLSPLSYIAAAITGHPDSKVHVXHEGXEKI 251                                           300
R.graminis       (250)   MFAREAISLFGLEAVVLGPKEGLGLVNGTAVSASMATLSLHDSHMLSLLS
R.mucilaginosa   (246)   MSAQEAIALKGLQPVVLGPKEGLGLVNGTAVSASMATLALTDAHVLSLLA
R.toruloides     (244)   LYAREAMALFNLEPVVLGPKEGLGLVNGTAVSASMATLALHDAHMLSLLS
Consensus        (251)   MXAREAIALFGLEPVVLGPKEGLGLVNGTAVSASMATLALHDAHMLSLLS 301                                           350
R.graminis       (300)   QALTALTVEAMVGQQGSFAPFIHDVCRPHPGQVEVARNIRTLLSGSSFAV
R.mucilaginosa   (296)   QALTALTVEAMVGHAGSFHPFLHDVTRPHPTQIEVARNIRTLLEGSKYAV
R.toruloides     (294)   QSLTAMTVEAMVGHAGSFHPFLHDVTRPHPTQIEVAGNIRKLLEGSRFAV
Consensus        (301)   QALTALTVEAMVGHAGSFHPFLHDVTRPHPTQIEVARNIRTLLEGSXFAV
```

FIGURE 1A

```
                         351                                            400
R.graminis      (350)    EHEEEVKVKDDEGILRQDRYPLRTSPQFLGPLVEDMMHAYSTLSLEN-NT
R.mucilaginosa  (346)    HHETFVKVKDDEGILRQDRYPLRCSPQWLGPLVSDMIHAHAVLSLEAGQS
R.toruloides    (344)    HHEEEVKVKDDEGILRQDRYPLRTSPQWLGPLVSDLIHAHAVLTIEAGQS
Consensus       (351)    HHEEEVKVKDDEGILRQDRYPLRTSPQWLGPLVSDMIHAHAVLSLEAGQS 401                                            450
R.graminis      (399)    TTDNPLLDVENKQTAHGGNFQASAVSISMEKTRLALALIGKLNFTQCTEL
R.mucilaginosa  (396)    TTDNPLIDLENKMTHHGGAFMASSVGNTMEKTRLAVALMGKVSFTQLTEM
R.toruloides    (394)    TTDNPLIDVENKTSHHGGNFQAAAVANTMEKTRLGLAQIGKLNFTQLTEM
Consensus       (401)    TTDNPLIDVENKXTHHGGNFQASAVXNTMEKTRLALALIGKLNFTQLTEM 451                                            500
R.graminis      (449)    LNAAMNRGLPSCLAAEDPSLNYHGKGLDIHIAAYASELGHLANPVTTFVQ
R.mucilaginosa  (446)    LNAGMNRALPSCLAAEDPSLSYHCKGLDIAAAAYTSELGHLANPVSTHVQ
R.toruloides    (444)    LNAGMNRGLPSCLAAEDPSLSYHCKGLDIAAAAYTSELGHLANPVTTHVQ
Consensus       (451)    LNAGMNRGLPSCLAAEDPSLSYHCKGLDIAAAAYTSELGHLANPVTTHVQ 501                                            550
R.graminis      (499)    PAEMGNQAVNSLALISARRTAEANDVLSLLLASHLYCTLQAVDLRAMELD
R.mucilaginosa  (496)    PAEMGNQAINSLALISARRTAEANDVLSLLLATHLYCVLQAVDLRAMEFE
R.toruloides    (494)    PAEMANQAVNSLALISARRTTESNDVLSLLLATHLYCVLQAIDLPAIEFE
Consensus       (501)    PAEMGNQAVNSLALISARRTAEANDVLSLLLATHLYCVLQAVDLRAMEFE 551                                            600
R.graminis      (549)    FKKQFDPLLPTLLQQHLGTGLDVN---ALALEVKKALNKRLEQTTTYDL
R.mucilaginosa  (546)    HTKAFEPMVTELLKQHFGALAT-----AEVEDKVRKSIYKRLQQNNSYDL
R.toruloides    (544)    FKKQFGPAIVSLIDQHFGSAMTGSNLRDELVEKVNKTLAKRLEQTNSYDL
Consensus       (551)    FKKQFXPXXXXLLXQHFGXXXTXXXXXXXELXXKVXKXLXKRLEQTNSYDL 601                                            650
R.graminis      (595)    EPRWHDAFSYATGTVVELLSSSPSANVTLTAVNAWKVASAEKAISLTREV
R.mucilaginosa  (591)    EQRWHDTFSVATGAVVEALAG---QEVSLASLNAWKVACAEKAIALTRSV
R.toruloides    (594)    VPRWHDAFSFAAGTVVEVLSS---TSLSLAAVNAWKVAAAESAISLTRQV
Consensus       (601)    EPRWHDAFSXATGTVVEXLSSXXXXXVSLAAVNAWKVAXAEKAISLTRXV 651                                            700
R.graminis      (645)    RNRFWQTPSSQAPAHAYLSPRTRVLYSFVREELGVQARRGDVFVGVQQFT
R.mucilaginosa  (638)    RDSFWAAPSSSSPALKYLSPRTRVLYSFVREEVGVKARRGDVYLGKQEVT
R.toruloides    (641)    RETFWSAASTSSPALSYLSPRTQILYAFVREELGVKARRGDVFLGKQEVT
Consensus       (651)    RXXFWXAPSSSSPALXYLSPRTRVLYSFVREELGVKARRGDVFLGKQEVT 701            726
R.graminis      (695)    IGSNVSRIYEAIKDGRINHVLVKMLA
R.mucilaginosa  (688)    IGTNVSRIYEAIKSGCIAPVLVKMMA
R.toruloides    (691)    IGSNVSKIYEAIKSGRINNVLLKMLA
Consensus       (701)    IGSNVSRIYEAIKSGRINXVLVKMLA
```

FIGURE 1B

```
                        1                                                   50
R.graminis      (1)  ATGGCCCCTTCCTTGGACTCGCTCGCCACCACGCTCGCCAACGGCTTTAC
R.mucilaginosa  (1)  ATGGCCCCCTCCGTCGACTCGATCGCGACTTCGGTTGCCAACTCCCTCTC
R.toruloides    (1)  ATGGCACCCTCGCTCGACTCGATCTCGCACTCGTTCGCAAACGGCGTCGC
Consensus       (1)  ATGGCCCCCTCCNTCGACTCGATCGCGACCTCCNTCGCCAACGGCNTCNC 51                                                  100
R.graminis      (51) CAACGGCTCGCACGCCGCTCCGACCAAGTCGGCTGCGGGCCCCACTTCGG
R.mucilaginosa  (51) GAACGGGTTGCACGCCG--CCGCC---GCCGCCAACGGTGGCGACGTCCA
R.toruloides    (51) ATCCGCAAAGCAGGCTG-----TC----------AATGGCGCCTCGACCA
Consensus       (51) NAACGGNTNGCACGCCGNNCCGNCNNNGNCGNCNACGGGCGCCACGTCCA 101                                                 150
R.graminis      (101) CTCTCCGCCGCACGCC-CGGCCTCGATGGCCACG-CCGCGCACCAGTCGC
R.mucilaginosa  (96)  CAAGAAGACGGCCGGTGCTGGCTCCCTCCTCCCGACCACCGAGACGACCC
R.toruloides    (86)  ACCTC-----GCAGTCGCAGGCTCGCACCTGCCCACAACCCAGGTCACGC
Consensus       (101) CNCTCNGNCGGCCGNCGCNGGCTCGCTCCTCCCGACCACCCAGNNGACGC 151                                                 200
R.graminis      (149) AGCTCGAGATCGTGCAGGAGCTCCTCAGCGACCCCACCG--ACG-ACGTC
R.mucilaginosa  (146) AGCTCGACATCGTTGAGCGCATCTTGGCCGACGCCGGCGCGACGGACCAG
R.toruloides    (131) AGGTCGACATCGTCGACAAGATGCTCGCCGCGCCGACCGACTCG-ACG--
Consensus       (151) AGCTCGACATCGTNGACNAGATCCTCGCCGACCCCACCGNNACGNACGNN 201                                                 250
R.graminis      (196) GTCGAGCTCAGCGGGTACAGCCTCACCGTCCGTGACGTTGTCGGCGCCGC
R.mucilaginosa  (196) ATCAAACTCGATGGGTACACCCTCACGCTCGGCGACGTCGTCGGCGCTGC
R.toruloides    (178) CTCGAACTCGACGGCTACTCGCTCAACCTCGGAGACGTCGTCTCGGCCGC
Consensus       (201) NTCGAACTCGACGGGTACACCCTCACCCTCGGNGACGTCGTCGGCGCCGC 251                                                 300
R.graminis      (246) CCGCAAGGGGCGCAGGGTCCGCGTC-CAGAACGACGACGAGATCCGCGCA
R.mucilaginosa  (246) TCGCCGTGGCCGCTCCGTCAAGGTCGCAGACAGCCCGC-ACATCCGCGAG
R.toruloides    (228) GAGGAAGGGCAGGCCTGTCCGCGTCAAGGACAG-CGACGAGATCCGCTCA
Consensus       (251) NCGCAAGGGGCCGCNCNGTCCGCGTCNCAGACAGNCGACGAGATCCGCGCA 301                                                 350
R.graminis      (295) CGCGTCGACAAGAGCGTCGACTTCCTCAAGGCCCAGCTTCAGAACTCGGT
R.mucilaginosa  (295) AAGATCGATGCCAGTGTCGAGTTCCTCCGTACTCAGCTCGACAACAGTCT
R.toruloides    (277) AAGATTGACAAATCGGTCGAGTTCTTGCGCTCGCAACTCTCCATGAGCCT
Consensus       (301) AAGATCGACAANAGNGTCGAGTTCCTCCGNNCNCAGCTCNACAACAGNGT 351                                                 400
R.graminis      (345) CTACGGAGTCACCACGGGTTTCGGTGGCTCGGCCGACACGAGGACTGAGG
R.mucilaginosa  (345) CTACGGTGTCACGACTGGTTTCGGCGGCTCGGCCGACACCGGACTGAGG
R.toruloides    (327) CTACGGCGTCACGACTGGATTTGGCGGATCCGCAGACACCCGCACCGAGG
Consensus       (351) CTACGGNGTCACGACTGGTTTCGGCGGCTCGGCCGACACCCGGACTGAGG 401                                                 450
R.graminis      (395) ATGCAGTCAGCCTCCAGAAGGCGCTCATCGAGCACCAGCTCTGCGGCGTG
R.mucilaginosa  (395) ATGCGATCTCGCTCCAAAAGGCCCTGCTCGAGCACCAGCTCTGCGGTGTC
R.toruloides    (377) ACGCCATCTCGCTCCAGAAGGCTCTCCTCGAGCACCAGCTCTGCGGTGTT
Consensus       (401) ATGCNATCTCGCTCCAGAAGGCNCTCCTCGAGCACCAGCTCTGCGGTGTN
```

Figure 2A

```
                      451                                                500
R.graminis     (445) ACGCCGACGTCCGTCTCGTCCTTCAGCGTCGGACGCGGCCTCGAGAACAC
R.mucilaginosa (445) CTCCCCACCTCCATGGATGGCTTTGCGCTCGGTCGCGGCCTCGAGAACTC
R.toruloides   (427) CTCCCTTCGTCGTTCGACTCGTTCCGCCTCGGCCGCGGTCTCGAGAACTC
Consensus      (451) CTCCCNACGTCGNTCGANTCCTTCNGCCTCGGNCGCGGCCTCGAGAACTC 501                                                550
R.graminis     (495) GCTTCCGCTCGAGGTCGTCCGCGGCGCCATGGTCATCCGCGTCAACTCGC
R.mucilaginosa (495) GCTTCCGCTCGAAGTCGTCCGAGGCGCGATGACCATCCGTGTCAACTCGC
R.toruloides   (477) GCTTCCCCTCGAGGTTGTTCGCGGCGCCATGACAATCCGCGTCAACAGCT
Consensus      (501) GCTTCCGCTCGAGGTCGTCCGCGGCGCCATGACCATCCGCGTCAACTCGC 551                                                600
R.graminis     (545) TCACGCGTGGCCACTCGGCCGTCCGCCTCGTCGTCCTTGAGGCGCTCACC
R.mucilaginosa (545) TCACTCGCGGTCACTCGGCGGTCCGCATCGTCGTCCTCGAAGCCCTCACC
R.toruloides   (527) TGACCCGCGGCCACTCGGCTGTCCGCCTCGTCGTCCTCGAGGCGCTCACC
Consensus      (551) TCACNCGCGGCCACTCGGCNGTCCGCCTCGTCGTCCTCGAGGCGCTCACC 601                                                650
R.graminis     (595) AACTTCTTGAACCACCGCATCACGCCCATCGTCCCCCTCCGCGGCTCCAT
R.mucilaginosa (595) AACTTCCTCAACCACGGCATCACCCCGATCGTCCCGCTTCGAGGCACCAT
R.toruloides   (577) AACTTCCTCAACCACGGCATCACCCCCATCGTCCCCCTCCGCGGCACCAT
Consensus      (601) AACTTCCTCAACCACGGCATCACCCCCATCGTCCCCCTCCGCGGCACCAT 651                                                700
R.graminis     (645) CTCGGCCTCGGGCGACCTCAGCCCGCTCTCGTACATCGCCGGCGCCATCA
R.mucilaginosa (645) CTCGGCGTCGCGCGACCTTTCCCCCCTCTCTTACATCGCCGCCTCGATCA
R.toruloides   (627) CTCTGCGTCGGGCGACCTCTCTCCTCTCTCCTACATTGCAGCGGCCATCA
Consensus      (651) CTCGGCGTCGGGCGACCTCTCCCCNCTCTCNTACATCGCCGCCGCCATCA 701                                                750
R.graminis     (695) CCGGTCACCCCGACGTCAAGGTTCACGTTTTGCACGAGGGAACCGAGAAG
R.mucilaginosa (695) CCGGCCACCCGGACTCGAAGGTCCACGT-----CGACGGCA------AG
R.toruloides   (677) GCGGTCACCCGGACAGCAAGGTGCACGTCGTCCACGAGGGCAAGGAGAAG
Consensus      (701) CCGGTCACCCGGACNNCAAGGTNCACGTNNTNCACGAGGGCANNGAGAAG 751                                                800
R.graminis     (745) ATCATGTTTGCGCGCGAGGCCATCTCGCTCTTTGGTCTCGAGGCAGTCGT
R.mucilaginosa (733) ATCATGTCCGCCCAGGAGGCGATCGCGCTCAAGGGTCTTCAGCCCGTCGT
R.toruloides   (727) ATCCTGTACGCCCGCCAGGCGATCGCGCTCTTCAACCTCGAGCCCGTCGT
Consensus      (751) ATCATGTNCGCCCGCGAGGCGATCGCGCTCTTNGGTCTCGAGCCCGTCGT 801                                                850
R.graminis     (795) CCTCGGCCCGAAGGAGCGTCTCGGTCTGGTCAACGGAACGGCCGTCTCCG
R.mucilaginosa (783) CCTCGGTCCGAAGGAGCGTCTCGGTCTCGTCAACGGCACGGCCGTCTCCG
R.toruloides   (777) CCTCGGCCCGAAGGAAGCTCTCGGTCTCGTCAACGGCACCGCCGTCTCAG
Consensus      (801) CCTCGGCCCGAAGGACGTCTCGGTCTCGTCAACGGCACGGCCGTCTCCG 851                                                900
R.graminis     (845) CCTCGATGGCGACCCTCAGTCTGCACGACTCGCACATGCTCTCGCTCCTC
R.mucilaginosa (833) CCTCGATGGCGACGCTGGCCCTCACCGACGCACACGTCCTCTCGCTCCTC
R.toruloides   (827) CATCGATGGCCACCCTCGCTCTGCACGACGCACACATGCTCTCGCTCCTC
Consensus      (851) CCTCGATGGCGACCCTCGCTCTGCACGACGCACACATGCTCTCGCTCCTC
```

Figure 2B

```
                         901                                                950
R.graminis     (895) TCGCAGGCCTTGACGGCTCTCACGGTGGAGGCCATGGTCGGCCAGCACGG
R.mucilaginosa (883) GCACAGGCGCTCACTGCTCTTACTGTCGAGGCCATGGTCGGACACGCCGG
R.toruloides   (877) TCGCAGTCGCTCACCGGCCATGACGGTCGAAGCGATGGTCGGCCACGCCGG
Consensus      (901) TCGCAGGCGCTCACCGGCTCTNACGGTCGAGGCCATGGTCGGCCACGCCGG 951                                               1000
R.graminis     (945) CTCGTTCCCGCCGTTCATCCACGACGTCTGCCGCCCGCACCCCGGCCAGG
R.mucilaginosa (933) CTCGTTCCACCCATTCCTCCACGACGTCACGCGCCCTCACCCGACCCAGA
R.toruloides   (927) CTCGTTCCACCCCTTCCTTCACGACGTCACGCGCCCTCACCCGACGCAGA
Consensus      (951) CTCGTTCCACCCNTTCCTCCACGACGTCACGCGCCCTCACCCGACCCAGA 1001                                               1050
R.graminis     (995) TCGAGGTCGCGCGCAACATCCGCACGCTCCTTTCCGGCTCGTCGTTTGCC
R.mucilaginosa (983) TCGAGGTGGCGCGCAACATCCGGACTCTTCTCGAGGGCAGCAAGTACGCC
R.toruloides   (977) TCGAAGTCGCGGGAAACATCCGCAAGCTCCTCGAGGGAAGCCGCTTTGCT
Consensus     (1001) TCGAGGTCGCGCGCAACATCCGCACGCTCCTCGAGGGCAGCNNGTTTGCC 1051                                               1100
R.graminis    (1045) GTTGAGCACGACGAGGAGGTCAAGGTCAAGGACGACGAGGGCATTCTTCG
R.mucilaginosa(1033) GTCCACCACCAGACTGAAGTCAAGGTCAAGGACGACGAGGGCATCCTCAG
R.toruloides  (1027) GTCCACCATGAGGAGGAGGTCAAGGTCAAGGACGACGAGGGCATTCTCCG
Consensus     (1051) GTCCACCACGAGGAGGAGGTCAAGGTCAAGGACGACGAGGGCATTCTCCG 1101                                               1150
R.graminis    (1095) CCAGGACCGCTACCCGCTCCGCACGTCGCCTCAGTTCCTCGGCCCGCTCG
R.mucilaginosa(1083) GCAGGACCGGTACCCGCTCCGCTGCTCGCCGCAGTGGCTCGGTCCCCTTG
R.toruloides  (1077) CCAGGACCGCTACCCCTTGCCCACGTCTCCTCAGTGGCTCGGCCCGCTCG
Consensus     (1101) CCAGGACCGCTACCCGCTCCGCACGTCGCCTCAGTGGCTCGGCCCGCTCG 1151                                               1200
R.graminis    (1145) TGGAGGACATGATGCACGCCTACTCGACTCTCTCGCTCGAGAACA---AC
R.mucilaginosa(1133) TCAGCGACATGATTCACGCTCACGCTGTCCTCTCGCTCGAGGCTGGTCAG
R.toruloides  (1127) TCAGCGACCTCATTCACGCCCACGCCGTCCTCACCATCGAGGCCGGCCAG
Consensus     (1151) TCAGCGACATGATTCACGCCCACGCNGTCCTCTCGCTCGAGGCCGGNCAG 1201                                               1250
R.graminis    (1192) ACGACGACCGACAACCCGCTCCTCGACGTCGAGAACAAGCAGACCGCGCA
R.mucilaginosa(1183) TCGACCACCGACAACCCGCTGATCGACCTCGAGAACAAGATGACCCACCA
R.toruloides  (1177) TCCACCACCGACAACCCTCTCATCGACGTCGAGAACAAGACTTCGCACCA
Consensus     (1201) TCGACGACCGACAACCCGCTCATCGACGTCGAGAACAAGANGACCCACCA 1251                                               1300
R.graminis    (1242) CGGCGGCAACTTCCAGGCGTCCGCTGTCTCGATTTCGATGGAGAAGACCA
R.mucilaginosa(1233) TGGCGGAGCCTTCATCGCGAGCAGCGTCGGAAACACGATGGAGAAGACTC
R.toruloides  (1227) CGGCGGCAATTTCCACGCTGCCGCTGTGGCCAACACCATGGAGAAGACTC
Consensus     (1251) CGGCGGCAACTTCCAGGCGNCCGCTGTCGCNAACACGATGGAGAAGACTC 1301                                               1350
R.graminis    (1292) GGCTCGCACTCGCCCTCATCGGCAAGCTCAACTTCACGCAGTGCACCGAG
R.mucilaginosa(1283) GCCTCGCCGTCGCGCTGATGGGCAAGGTCAGCTTTACTCAGCTCACCGAG
R.toruloides  (1277) GCCTCGGGCTCGCCCACATCGGCAAGCTCAACTTCACGCAGCTCACCGAG
Consensus     (1301) GCCTCGCNCTCGCCCTGATCGGCAAGCTCAACTTCACGCAGCTCACCGAG
```

Figure 2C

```
                             1351                                        1400
R.graminis      (1342)  TTGCTCAACGCTGCCATGAACCGCGGCCTGCCTTCGTGCCTCGCTGCCGA
R.mucilaginosa  (1333)  ATGCTCAACGCCGGCATGAACCGGGCCCTTCCGTCCTGCCTCGCTGCCGA
R.toruloides    (1327)  ATGCTCAACGCCGGCATGAACCGCGGCCTCCCCTCCTGCCTCGCGGCCGA
Consensus       (1351)  ATGCTCAACGCCGGCATGAACCGCGGCCTNCCNTCCTGCCTCGCTGCCGA 1401                                        1450
R.graminis      (1392)  GGACCCGTCGCTCAACTATCACGGCAAGGGCTTGGACATTCACATCGCTG
R.mucilaginosa  (1383)  GGACCCTTCCCTCTCTTATCACTGCAAGGGTCTCGACATTGCTGCGGCCG
R.toruloides    (1377)  AGACCCCTCGCTCTCCTACCACTGCAAGGGCCTCGACATCGCCGCTGCGG
Consensus       (1401)  GGACCCNTCGCTCTCCTATCACTGCAAGGGCCTCGACATTGCCGCNGCNG 1451                                        1500
R.graminis      (1442)  CTTACGCTTCGGAGCTCGGCCACCTTGCCAACCCGGTCACTACCTTCGTC
R.mucilaginosa  (1433)  CCTACACTTCCGAGCTCGGTCACCTTGCCAACCCGGTTTCGACCCACGTC
R.toruloides    (1427)  CGTACACCTCGGAGTTGGGACACCTCGCCAACCCTGTCACGACGCATGTC
Consensus       (1451)  CNTACACTTCGGAGCTCGGNCACCTTGCCAACCCGGTNACGACCCACGTC 1501                                        1550
R.graminis      (1492)  CAGCCCGCAGAGATGGGCAACCAGGCCGTCAACTCGCTCGCTCTCATCTC
R.mucilaginosa  (1483)  CAGCCCGCCGAGATGGGCAACCAGGCCATCAACTCGCTCGCCCTCATCTC
R.toruloides    (1477)  CAGCCGGCTGAGATGGCGAACCAGGCGGTCAACTCGCTTGCGCTCATCTC
Consensus       (1501)  CAGCCGGCNGAGATGGGCAACCAGGCCGTCAACTCGCTCGCNCTCATCTC 1551                                        1600
R.graminis      (1542)  CGCGCGCCGCACTGCCGAGGCCAACGACGTCCTTTCTCTCCTTCTCGCCT
R.mucilaginosa  (1533)  GGCCCGCCGCACCGCCGAGGCGAACGACCTTCTCTCCTCCTCCTCGCCA
R.toruloides    (1527)  GGCTCGTCGCACGACCGAGTCCAACGACGTCCTTTCTCTCCTCCTCGCCA
Consensus       (1551)  GGCNCGCCGCACNGCCGAGGCCAACGACGTCCTTTCTCTCCTCCTCGCCA 1601                                        1650
R.graminis      (1592)  CGCACCTGTACTGCACGCTCCAGGCCGTCGACCTCCGCGCGATGGAGCTC
R.mucilaginosa  (1583)  CCCACCTCTACTGCGTCCTCCAGGCCGTCGACCTCCGCGCGATGGAGTTT
R.toruloides    (1577)  CCCACCTCTACTGCGTTCTCCAAGCCATCGACTTGCGCGCGATCGAGTTC
Consensus       (1601)  CCCACCTCTACTGCGTNCTCCAGGCCGTCGACCTCCGCGCGATGGAGTTC 1651                                        1700
R.graminis      (1642)  GACTTCAAGAAGCAGTTCGACCCGCTTCTCCCGACTCTCCTCCAGCAGCA
R.mucilaginosa  (1633)  GAGCACACCAAGGCGTTCGAGCCGATGGTCACTGAGCTGTTGAAGCAGCA
R.toruloides    (1627)  GAGTTCAAGAAGCAGTTCGGCCCAGCCATCGTCTCGCTCATCGACCAGCA
Consensus       (1651)  GAGTTCAAGAAGCAGTTCGACCCGNTNNTCNCNNCGCTCNTCNAGCAGCA 1701                                        1750
R.graminis      (1692)  CCTCGGCACTGGCCTCGACGTCA----------ACGCACTTGCGCTCG
R.mucilaginosa  (1683)  CTTTGGCGC-GCTCGCGACGGC-------------CGAAGTCGAGGACA
R.toruloides    (1677)  CTTTGGCTCCGCCATGACCGGCTCGAACCTGCGCGACGAGCTCGTCGAGA
Consensus       (1701)  CTTTGGCNCNGCCCTCGACGGCNNNNNNNNNNNNNACGAACTCGNGGACA 1751                                        1800
R.graminis      (1730)  AGGTCAAGAAGCGCGCTCAACAAGCGTCTCGAGCAGACGACGACGTACGAC
R.mucilaginosa  (1718)  AGGTCCGCAAGTCGATCTACAAGCGGTTGCAGCAGAACAACTCGTACGAC
R.toruloides    (1727)  AGGTGAACAAGACGCTCGCCAAGCGCCTCGAGCAGACCAACTCGTACGAC
Consensus       (1751)  AGGTCAACAAGNCGCTCNACAAGCGNCTCGAGCAGACCAACTCGTACGAC
```

Figure 2D

```
                           1801                                          1850
R.graminis     (1780) CTCGAGCCGCGCTGGCACGACGCCTTCTCGTACGCGACCGGCACCGTCGT
R.mucilaginosa (1768) CTCGAGCAGCGGTGGCACGACACGTTCTCGGTCGCGACCGGTGCCGTCGT
R.toruloides   (1777) CTCGTCCCGCGCTGGCACGACGCCTTCTCCTTCGCCGCCGGCACCGTCGT
Consensus      (1801) CTCGAGCCGCGCTGGCACGACGCCTTCTCGTTCGCGACCGGCACCGTCGT 1851                                          1900
R.graminis     (1830) CGAGCTCCTCTCGTCCTCGCCCTCTGCCA--ACGTCACCCTTACTGCCGT
R.mucilaginosa (1818) CGAG--------GCGCTCGCCG---GCCAGGAGGTCTCGCTCGCGAGCCT
R.toruloides   (1827) CGAG--------GTCCTCTCGTC--GACGT-CGCTCTCGCTCGCCGCCGT
Consensus      (1851) CGAGNNNNNNNNNGTCCTCGCCNNNNGCCANNAGGTCTCGCTCGCNGCCGT 1901                                          1950
R.graminis     (1878) CAACGCGTGGAAGGTTGCCTCGGCCGACAAGGCCATCTCGCTCACGCGCG
R.mucilaginosa (1857) CAACGCCTGGAAGGTCGCCTGCGCCGAGAAGGCTATCGCGCTCACGCGCT
R.toruloides   (1866) CAACGCCTGCAACGTCGCCGCCGCCGAGTCGGCCATCTCGCTCACCCGCC
Consensus      (1901) CAACGCCTGCAAGGTCGCCTCCGCCGAGAAGGCCATCTCGCTCACGCGCN 1951                                          2000
R.graminis     (1928) AGGTGCGCAACCGCTTCTGGCAGACGCCGTCTTCGCAGGCGCCGGCGCAC
R.mucilaginosa (1907) CCGTCCGCGACTCGTTCTGGGCGGCTCCGTCGTCGTCGTCGCCCGCGCTC
R.toruloides   (1916) AAGTCCGCGAGACCTTCTGGTCCGCCGCGTCGACCTCGTCGCCCGCGCTC
Consensus      (1951) ANGTCCGCGACNCCTTCTGGNCGGCNCCGTCGTCGTCGTCGCCCGCGCTC 2001                                          2050
R.graminis     (1978) GCATACCTCTCGCCGCGCACGCGCGTCCTGTACTCGTTCGTGCGCGAGGA
R.mucilaginosa (1957) AAGTACCTCTCCCCGCCGGACGCGCGTCCTGTATTCGTTCGTCCGGGAGGA
R.toruloides   (1966) TCGTACCTCTCGCCGCGCACTCAGATCCTCTACGCCTTCGTCCGCGAGGA
Consensus      (2001) NCGTACCTCTCGCCGCGCACGCGCGTCCTGTACTCGTTCGTCCGCGACGA 2051                                          2100
R.graminis     (2028) GCTCGGCGTGCAGGCGCGCCGCGGCGACGTGTTTCTCGGCGTGCAGCAGG
R.mucilaginosa (2007) GGTCGGCGTCAAGGCCCGCCGCGGCGATGTCTACCTCGGCAAGCAGGAGG
R.toruloides   (2016) GCTTGGCGTCAAGGCCCGCCGCGGAGACGTCTTCCTCGGCAAGCAAGAGG
Consensus      (2051) GCTCGGCGTCAAGGCCCGCCGCGGCGACGTCTTCCTCGGCAAGCAGGAGG 2101                                          2150
R.graminis     (2078) AGACGATCGGCAGCAACGTCTCGCGCATCTACGAGGCCATCAAGGACGGC
R.mucilaginosa (2057) TCACGATCGGCACCAACGTCAGCCGCATCTACGAGGCGATCAAGAGCGGT
R.toruloides   (2066) TGACGATCGGCTCGAACGTCTCCAAGATCTACGAGGCCATCAAGTCGGGC
Consensus      (2101) TGACGATCGGCACCAACGTCTCCCGCATCTACGAGGCCATCAAGNNCGGC 2151                                          2200
R.graminis     (2128) CGCATCAACCACGTCCTCGTCAAGATGCTCGCGTAACGCC-CGAGCAAGC
R.mucilaginosa (2107) TGCATCGCCCCCGTCCTCGTCAAGATGATGGCATAG--------------
R.toruloides   (2116) AGGATCAACAACGTCCTCCTCAAGATGCTCGCTTAGACACTCTTCCCACT
Consensus      (2151) NGCATCAACCACGTCCTCGTCAAGATGCTCGCNTAGNNCNCNNNCNANN 2201                                          2250
R.graminis     (2177) CTCGCCTAGACGCCCGCCTCACCCCAAGACCAGCTTTTCGACGTCGTGTC
R.mucilaginosa (2143) --------------------------------------------------
R.toruloides   (2166) CTCGCATCCCTTCCATACCCTATCCCGCCTGCACTCTTAGGACTCGCTTC
Consensus      (2201) CTCGCNTNNNNNCCNNNCNCNNNCCNNNNNNNNCTNTTNGNNNTCGNNTC
```

Figure 2E

```
                        2251                                                2300
R.graminis      (2227)  GTGCCAAGAACGGACTTTCCTCCATACACATGTCGCCTTACTCTCTCGCC
R.mucilaginosa  (2143)  --------------------------------------------------
R.toruloides    (2216)  TTGTCGGACTCGGATCTCGCATCGCTTCTTTCGTTCTTGGCTGCCTCTCT
Consensus       (2251)  NTGNCNNNNNCGGANNTNNCNNCNNNNNNNTNNNNCNTNNCTNNCTCNCN 2301                                                2350
R.graminis      (2277)  GTCATCACGTCTCTCAGTTCTTTCGTATCCCGCGTCTCTCGGTCGTCAGT
R.mucilaginosa  (2143)  --------------------------------------------------
R.toruloides    (2266)  AG-ACCGTGTCCGTATTACCTCGAGATTGTGAATACAAGCACTACCCATC
Consensus       (2301)  NNNANCNNGTCNNTNNNNNCTNNNGNNTNNNNNNNCNNNCNGTNNNCANN 2351                                                2400
R.graminis      (2327)  -ACACGTGTATAGAGCCTGGAATGGATTGCAACTCTTCGAGTTCAAAAAA
R.mucilaginosa  (2143)  --------------------------------------------------
R.toruloides    (2315)  CACGCATCCGATAAATCAGGGAGAGAATCTACGCTTGCGGGAGCTTCTTG
Consensus       (2351)  NACNCNTNNNNNNNANNCNGGNANNGANTNNANGNNTNCGNGNNCNNNNN 2401                                                2450
R.graminis      (2376)  AAAAAAAA------------------------------------------
R.mucilaginosa  (2143)  --------------------------------------------------
R.toruloides    (2365)  CGCATAAACTGTCGAGTGCGGGCGTTAGTGCGAAGTCAACGAAGGCGAGT
Consensus       (2401)  NNNANAAANNNNNNNNNNNNNNNNNNNNNNNNNNNNNNNNNNNNNNNNNN 2451       2475
R.graminis      (2384)  --- --------------------
R.mucilaginosa  (2143)  --- --------------------
R.toruloides    (2415)  GGCAGCGGCTCACTACCGCCTCGAG
Consensus       (2451)  NNNNNNNNNNNNNNNNNNNNNNNNN
```

Figure 2F

```
ATGGCCCCTTCCTTGGACTCGCTCGCCACCACGCTCGCCAACGGCTTTACCAACGGCTCGCACGCCGCTCCGA
CCAAGTCGGCTGCGGGCCCCACTTCGGCTCTCCGCCGCACGCCCGGCCTCGATGGCCACCCCGCGCACCAGTC
GCAGCTCGAGATCGTGCAGGAGCTCCTCAGCGACCCCACCGACGACGTCGTCCACCTCAGCGGGTACAGCCTC
ACCGTCCGTGACGTTGTCGGCGCCGCCCGCAAGGGGCGCAGGGTCCGCGTCCAGAACGACGACGAGATCCGCG
CACGCGTCGACAAGAGCGTCGACTTCCTCAAGGCCCAGCTTCAGAACTCCGTCTACGGAGTCACCACGGTGCG
TTCCGAGACGAGAGGCGGAAATCTCGGGATGCCGCAGCGCTGAACGCTGACACTCGCTTGGACGGCTGCCGCG
GTCTTGCAGGGTTTCGGTGGCTCGGCCGACACGAGGACTCAGGATGCAGTCAGCCTCCAGAAGGCGCTCATCG
AGCACCAGCTCTGCGGCGTGACGCCGACGTCCGTCTCGTCCTTCAGCGTCGGACGCGGCCTCGAGAACACGCT
TCCGCTCGAGGTCGTCCGCGGCGCCATGGTCATCCGCGTCAACTCGCTCACGCGTGGCCACTCGGCCGTCCGC
CTCGTCGTCCTTGAGGCGCTCACCAACTTCTTGAACCACCGCATCACGCCCATCGTCCCCCTCCGCGGCTCCA
TCTCGGCGTCGGGCGACCTCAGCCCGCTCTCGTACATCGCCGGCGCCATCACCGGTCACCCCGACGTCAAGGT
TCACGTTTTGCACGAGGGAACCGAGAAGATCATGTTTGCGCGCGAGGCCATCTCGCTCTTTGGTCTCGAGGCA
GTCGGTACGTCGCGAGTCCTGACTGCAGTGAGCTGTTCGAGAGTCTCCCAGTTTGCTGACTGCCCTTTGTTCA
TGCGATTGCAGTCCTCGGCCCGAAGGAGGGTCTCGGTCTGGTCAACGGAACGGCCGTCTCCGCCTCGATGGCG
ACCCTCAGTCTGCACGACTCGCACATGCTCTCGCTCCTCTCGCAGGCCTTGACGGCTCTCACGGTGGAGGCCA
TCGTCGGCCAGCAGGGCTCGTTCGCGCCGTTCATCCACGACGTCTGCCGCCCGCACCCCGGCCAGGTCGAGGT
CCCGCGCAACATCCGCACGCTCCTTTCCGGCTCGTCGTTTGCCGTTGAGCACGAGGAGGAGGTCAAGGTCAAG
GACGACGAGGGCATTCTTCGCCAGGACCGCTACCCGCTCCGCACGTCGCCTCAGGTTCGTCCCCTCTCTCTCC
CCTTCCCTCCGTCCGACCGGCGCGTCGAGACTTACGTTTTGCGTATCCAGTTCCTCGGCCCGCTCGTGGAGGA
CATGATGCACGCCTACTCGACTCTCTCGCTCGAGAACAACACGACGACCGACAACCCGCTCCTCGACGTCGAG
AACAAGCAGACCGCGCACGGCGGCAACTTCCAGGCGTCGGCTGTCTCCATTTCGATGGAGAAGACCAGGTGCG
TCTCTCGCTGCCTTCGTACTCCGATCTTGTGCTGAATGTTCTTCTCCTGCAGGCTCGCACTCGCCCTCATCGG
CAAGCTCAACTTCACGCAGTGCACCGAGTTCCTCAACGCTGCCATGAACCGCGGCCTGCCTTCGTGCCTCGCT
GCCGAGGACCCGTCGCTCAACTATCACGCCAAGGGCTTGGACATTCACATCGCTGCTTACGCTTCGGAGGTGA
GCCGTCGACGTTCTCCGCCGTCGCTCGTCCCCTTCAGCGCACCCAGGCTGACTTCCTTTCCGCTGTAGCTCG
GCCACCTTGCCAACCCGGTCACTACCTTCGTCCAGCCCGCAGAGATGGGCAACCAGGCCGTCAACTCGCTCGC
TCTCATCTCCGCGCCGCACTGCCGAGCCAACGACGTCCTTTCTCTCGTCGCGTCGTGTCGCAATGACTCC
CGACGCAATAGCGACTGACTGCGCGATCCTGAGCAGCTTCTCGCCTCGCACCTGTACTGCACGCTCCAGGCCG
TCGACCTCCGCGCGATGGAGCTCGACTTCAAGAAGCAGTTCGACCCGCTTCTCCGACTCTCCTCCAGCACCA
CCTCGGCACTGGCCTCGACGTCAACGCACTTGCCCTCGAGGTCAAGAACGCGCTCAACAAGCGTCTCGAGCAG
ACGACGACGTACGACCTCGAGCCGCGCTGGCACGACGCCTTCTCGTACGCGACCGGCACCGTCGTCGAGCTCC
TCTCGTCCTCGCCCTCTGCCAACGTCACCCTTACTGCCGTCAACGCGTGGAAGGTTGCCTCGGCCGAGAAGGC
CATCTCGCTCACGCGCGAGGTGCGCAACCCCTTCTGGCAGACGCCGTCTTCGCAGCCGCCGGCGCACGCATAC
CTCTCGCCGCCACGCGCGTCCTGTACTCGTTCGTGCGCGAGGAGCTCGGCGTCCAGGCGCGCCGCGGCGACG
TGTTCTCGGCGTGCAGCAGGAGACGATCGGGAGCAACGTCTCGCGCATCTACGAGGCCATCAAGGACGGCCG
CATCAACCACGTCCTCGTCAAGATGCTCGCGTAAGCCCGAGCAAGCCTCGCCTAGACGCCCGCCTCACCCCA
AGACCAGCTTTTCGACGTCGTGTCGTGCCAAGAACGGACTTTCCTCCATACACATGTCGTCTTACTCTCTCGC
CGTCATCACGTCTCTCAGTTCTTTCGTATCCCGCGTCTCT
```

FIGURE 3

```
ATGGCACCTTCCTTGGACTCGCTCGCCACCACGCTCGCCAACGGCTTTACCAACGGCTCGCACGCCGCTCCGA
CCAAGTCGGCTGCGGGCCCCACTTCGGCTCTCCGCCGCACGCCCGGCCTCGATGGCCACGCCGCGCACCAGTC
GCAGCTCGAGATCGTGCAGGAGCTCCTCAGCGACCCCACCGACGACGTCGTCGAGCTCAGCGGGTACAGCCTC
ACCGTCCGTGACGTTGTCGGCGCCGCCCGCAAGGGGCGCAGGCTCCGCGTCCAGAACGACGACGAGATCCGCG
CACGCGTCGACAAGAGCGTCGACTTCCTCAAGGCCCAGCTTCAGAACTCGGTCTACGGAGTCACCACGGTGCG
TTCCGAGACGAGAGGCGGAAATCTCGGGATGCCGCAGCGCTGAACGCTGACACTCGCTTGGACGGCTGCCGCG
GTCTTGCAGGGTTTCGGTGGCTCGGCCGACACGAGGACTGAGGATGCAGTCAGCCTCCAGAAGGCGCTCATCG
AGCACCAGCTCTGCGGCGTGACGCCGACGTCCGTCTCGTCCTTCAGCGTCGGACGCGGCCTCGAGAACACGCT
TCCGCTCGAGGTCGTCCGCGGCGCCATGGTCATCCGCGTCAACTCGCTCACGCGTGGCCACTCGGCCGTCCGC
CTCGTCGTCCTTGAGGCGCTCACCAACTTCTTGAACCACCGCATCACGCCCATCGTCCCCCTCCGCGGCTCCA
TCTCGGCGTCGGGCGACCTCAGCCCGCTCTCGTACATCGCCGGCGCCATCACCGGTCACCCCGACGTCAAGGT
TCACGTTTTGCACGAGGGAACCGACAAGATCATGTTTGCGCGCGAGGCCATCTCGCTCTTTGGTCTCGAGGCA
GTCGGTACGTCGCGAGTCCTGACTGCAGTGAGCTGTTCGAGAGTCTCCCAGTTTGCTGACTGCCCTTTGTTCA
TGCGATTGCAGTCCTCGGCCCGAAGGAGGGTCTCCGTCTGGTCAACGGAACGGCCGTCTCCGCCTCGATGGCG
ACCCTCAGTCTGCACGACTCGCACATGCTCTCGCTCCTCTCGCAGGCCTTGACGGCTCTCACGGTGGAGGCCA
TGGTCGGCCAGCAGGGCTCGTTCGCGCCCTTCATCCACGACGTCTGCCGCCCGCACCCCGGCCAGGTCGAGGT
CGCGCGCAACATCCGCACGCTCCTTTCCGGCTCGTCGTTTGCCGTTGAGCACGAGGAGGAGGTCAAGGTCAAG
GACGACGAGGGCATTCTTCGCCAGGACCGCTACCCGCTCCGCACGTCGCCTCAGGTTCGTCCCCTCTCTCTCC
CCTTCCCTCCGTCCGACCGGCGCGTCGAGACTTACGTTTTGCGTATCCAGTTCCTCGGCCCGCTCGTGGAGGA
CATGATCCACGCCTACTCGACTCTCTCGCTCGAGAACAACACGACGACCGACAATCCGCTCCTCGACGTCGAG
AACAAGCAGACCGCGCACGGCGGCAACTTCCAGGCGTCGGCTGTCTCGATTTCGATGGAGAAGACCAGGTGCG
TCTCTCGCTGCCTTCGTACTCCGATCTTGTGCTGAATGTTCTTCTCCTGCAGGCTCGCACTCGCCCTCATCGG
CAAGCTCAACTTCACGCAGTGCACCGAGTTGCTCAACGCTGCCATGAACCGCGGCCTGCCTTCGTGCCTCGCT
CCCGAGGACCCGTCGCTCAACTATCACGGCAAGGGCTTGGACATTCACATCGCTGCTTACGCTTCGGAGGTCA
GCCGTCGACGTTCTCCGCCGTCGCTCGTCCCCTTCAGCGCACCCAGGCTGACTTCCTTTCCCTCTGTAGCTCG
GCCACCTTGCCAACCCGGTCACTACCTTCGTCCAGCCCGCAGAGATGGGCAACCAGGCCGTCAACTCGCTCCG
TCTCATCTCCGCGCGCCGCACTGCCGAGGCCAACGACGTCCTTTCTCTCGTGCGTTCGTGTCGCAATGACTCC
CGACGCAATACCGACTGACTGCGCGATCCTGAGCAGCTTCTCGCCTCGCACCTGTACTGCACGCTCCAGGCCG
TCGACCTCCGCGCGATGGAGCTCGACTTCAAGAAGCAGTTCGACCCGCTTCTCCCGACTCTCCTCCAGCAGCA
CCTCGGCACTGGCCTCGACGTCAACGCACTTGCGCTCGAGGTCAAGAAGGCGCTCAACAAGCGTCTCGAGCAG
ACGACGACGTACGACCTCGAGCCGCGCTGGCACGACGCCTTCTCGTACCCCACCGGCACCGTCGTCGAGCTCC
TCTCGTCCTGCCCTCTGCCAACGTCACCCTTACTGCCGTCAACGCGTGGAACTTGCCTCGGCCGAGAAGGC
CATCTCGCTCACGCGCGAGGTGCGCAACCGCTTCTGGCAGACGCCGTCTTCGCAGGCGCCGGCGCACGCATAC
CTCTCGCCGCGCACGCCCGTCCTGTACTCGTTCGTGCGCGAGGAGCTCGGCGTGCAGGCGCGCCGCGGCGACG
TGTTTGTCGGCGTGCAGCAGGAGACCATCGGGAGCAACGTCTCGCGCATCTACGAGGCCATCAAGGACGGCCG
CATCAACCACGTCCTCGTCAACATGCTCGCGTAAGGCCCGAGCAAGCCTCGCCTAGACGCCCGCCTCACCCCA
AGACCAGCTTTTCGACGTCGTCTCGTGCCAAGAACGGACTTTCCTCCATACACATGTCGTCTTACTCTCTCGC
CGTCATCACGTCTCTCAGTTCTTTCGTATCCCGCGTCTCT
```

FIGURE 4

SEQUENCE LISTING

```
<160> NUMBER OF SEQ ID NOS: 30

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: synthetic
      primer OLI 61

<400> SEQUENCE: 1
gacggatcca ctatggcbcc btcsgtsgac tcgat                               35

<210> SEQ ID NO 2
<211> LENGTH: 33
<212> TYPE: DNA
<213> ORGANISM: Artificial Sequence
<220> FEATURE:
<221> NAME/KEY: modified_base
<222> LOCATION: (13)
<223> OTHER INFORMATION: n = (a or c or g or t/u) or (unknown or other)
<223> OTHER INFORMATION: Description of Artificial Sequence: Synthetic
      Primer OLI 63

<400> SEQUENCE: 2
gacgaattct tangccatca tcttsacsag gac                                 33

<210> SEQ ID NO 3
<211> LENGTH: 36
<212> TYPE: DNA
<213> ORGANISM: Artificial Sequence
<220> FEATURE:
<221> NAME/KEY: modified_base
<222> LOCATION: (24, 25, 29, 30, 34, 35)
<223> OTHER INFORMATION: n = i or inosine
<223> OTHER INFORMATION: Description of Artificial Sequence: Synthetic
      Primer AAP

<400> SEQUENCE: 3
ggccacgcgt cgactagtac gggnngggnn gggnng                              36

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer GSP2

<400> SEQUENCE: 4
cgcgaattca gaatgccctc gtcgtccttg acc                                 33
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic Primer AUAP

<400> SEQUENCE: 5
ggccacgcgt cgactagtac                                            20

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic Primer GSP4

<400> SEQUENCE: 6
ccggaattcc gacgagccgg aaaggagcgt gcg                              33

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic Primer AP

<400> SEQUENCE: 7
ggccacgcgt cgactagtac tttttttttt ttttttt                         37

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic Primer GSP5

<400> SEQUENCE: 8
ggtcaaggac gacgagggca ttct                                       24

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic Primer GSP6

<400> SEQUENCE: 9
ccgggatcca tgatgcacgc ctactcgact ctctcgct                        38

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic Primer OLI 77

<400> SEQUENCE: 10
atcgaattcc actctaaccc gtcactagca ctcgcg                          36

<210> SEQ ID NO 11

-continued

```
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer OLI 78

<400> SEQUENCE: 11
atcggatccc acgacacgac gtcgaaaagc tggtct                               36

<210> SEQ ID NO 12
<211> LENGTH: 2419
<212> TYPE: DNA
<213> ORGANISM: Rhodotorula graminis
<220> FEATURE:
<221> NAME/KEY: CDS
<222> LOCATION: (37)..(2196)
<221> NAME/KEY: modified_base
<222> LOCATION: (494)
<223> OTHER INFORMATION: Other information:  y = t or c
<221> NAME/KEY: unsure
<222> LOCATION: (493)..(495)
<223> OTHER INFORMATION: Other information:  Xaa = Val or Ala

<400> SEQUENCE: 12
```

| | | | | | | | | | | | | | | | | |
|---|---|---|---|---|---|---|---|---|---|---|---|---|---|---|---|---|
| ctcctgcctc | actctaaccc | gtcactagca | ctcgcg | atg | gcc | cct | tcc | ttg | gac | | | | | | | 54 |
| | | | | Met | Ala | Pro | Ser | Leu | Asp | | | | | | | |
| | | | | 1 | | | | 5 | | | | | | | | |

```
tcg ctc gcc acc acg ctc gcc aac ggc ttt acc aac ggc tcg cac gcc       102
Ser Leu Ala Thr Thr Leu Ala Asn Gly Phe Thr Asn Gly Ser His Ala
            10                  15                  20 gct ccg acc aag tcg gct gcg ggc ccc act tcg gct ctc cgc cgc acg       150
Ala Pro Thr Lys Ser Ala Ala Gly Pro Thr Ser Ala Leu Arg Arg Thr
        25                  30                  35 ccc ggc ctc gat ggc cac gcc gcg cac cag tcg cag ctc gag atc gtg       198
Pro Gly Leu Asp Gly His Ala Ala His Gln Ser Gln Leu Glu Ile Val
    40                  45                  50 cag gag ctc ctc agc gac ccc acc gac gac gtc gtc gag ctc agc ggg       246
Gln Glu Leu Leu Ser Asp Pro Thr Asp Asp Val Val Glu Leu Ser Gly
55                  60                  65                  70 tac agc ctc acc gtc cgt gac gtt gtc ggc gcc gcc cgc aag ggg cgc       294
Tyr Ser Leu Thr Val Arg Asp Val Val Gly Ala Ala Arg Lys Gly Arg
                75                  80                  85 agg gtc cgc gtc cag aac gac gac gag atc cgc gca cgc gtc gac aag       342
Arg Val Arg Val Gln Asn Asp Asp Glu Ile Arg Ala Arg Val Asp Lys
            90                  95                 100 agc gtc gac ttc ctc aag gcc cag ctt cag aac tcg gtc tac gga gtc       390
Ser Val Asp Phe Leu Lys Ala Gln Leu Gln Asn Ser Val Tyr Gly Val
        105                 110                 115 acc acg ggt ttc ggt ggc tcg gcc gac acg agg act gag gat gca gtc       438
Thr Thr Gly Phe Gly Gly Ser Ala Asp Thr Arg Thr Glu Asp Ala Val
    120                 125                 130 agc ctc cag aag gcg ctc atc gag cac cag ctc tgc ggc gtg acg ccg       486
Ser Leu Gln Lys Ala Leu Ile Glu His Gln Leu Cys Gly Val Thr Pro
135                 140                 145                 150 acg tcc gyc tcg tcc ttc agc gtc gga cgc ggc ctc gag aac acg ctt       534
Thr Ser Xaa Ser Ser Phe Ser Val Gly Arg Gly Leu Glu Asn Thr Leu
                155                 160                 165 ccg ctc gag gtc gtc cgc ggc gcc atg gtc atc cgc gtc aac tcg ctc       582
Pro Leu Glu Val Val Arg Gly Ala Met Val Ile Arg Val Asn Ser Leu
            170                 175                 180 acg cgt ggc cac tcg gcc gtc cgc ctc gtc gtc ctt gag gcg ctc acc       630
Thr Arg Gly His Ser Ala Val Arg Leu Val Val Leu Glu Ala Leu Thr
        185                 190                 195
```

```
aac ttc ttg aac cac cgc atc acg ccc atc gtc ccc ctc cgc ggc tcc      678
Asn Phe Leu Asn His Arg Ile Thr Pro Ile Val Pro Leu Arg Gly Ser
    200                 205                 210 atc tcg gcg tcg ggc gac ctc agc ccg ctc tcg tac atc gcc ggc gcc      726
Ile Ser Ala Ser Gly Asp Leu Ser Pro Leu Ser Tyr Ile Ala Gly Ala
215                 220                 225                 230 atc acc ggt cac ccc gac gtc aag gtt cac gtt ttg cac gag gga acc      774
Ile Thr Gly His Pro Asp Val Lys Val His Val Leu His Glu Gly Thr
                235                 240                 245 gag aag atc atg ttt gcg cgc gag gcc atc tcg ctc ttt ggt ctc gag      822
Glu Lys Ile Met Phe Ala Arg Glu Ala Ile Ser Leu Phe Gly Leu Glu
            250                 255                 260 gca gtc gtc ctc ggc ccg aag gag ggt ctc ggt ctg gtc aac gga acg      870
Ala Val Val Leu Gly Pro Lys Glu Gly Leu Gly Leu Val Asn Gly Thr
        265                 270                 275 gcc gtc tcc gcc tcg atg gcg acc ctc agt ctg cac gac tcg cac atg      918
Ala Val Ser Ala Ser Met Ala Thr Leu Ser Leu His Asp Ser His Met
280                 285                 290 ctc tcg ctc ctc tcg cag gcc ttg acg gct ctc acg gtg gag gcc atg      966
Leu Ser Leu Leu Ser Gln Ala Leu Thr Ala Leu Thr Val Glu Ala Met
295                 300                 305                 310 gtc ggc cag cag ggc tcg ttc gcg ccg ttc atc cac gac gtc tgc cgc     1014
Val Gly Gln Gln Gly Ser Phe Ala Pro Phe Ile His Asp Val Cys Arg
                315                 320                 325 ccg cac ccc ggc cag gtc gag gtc gcg cgc aac atc cgc acg ctc ctt     1062
Pro His Pro Gly Gln Val Glu Val Ala Arg Asn Ile Arg Thr Leu Leu
                330                 335                 340 tcc ggc tcg tcg ttt gcc gtt gag cac gag gag gag gtc aag gtc aag     1110
Ser Gly Ser Ser Phe Ala Val Glu His Glu Glu Glu Val Lys Val Lys
            345                 350                 355 gac gac gag ggc att ctt cgc cag gac cgc tac ccg ctc cgc acg tcg     1158
Asp Asp Glu Gly Ile Leu Arg Gln Asp Arg Tyr Pro Leu Arg Thr Ser
360                 365                 370 cct cag ttc ctc ggc ccg ctc gtg gag gac atg atg cac gcc tac tcg     1206
Pro Gln Phe Leu Gly Pro Leu Val Glu Asp Met Met His Ala Tyr Ser
375                 380                 385                 390 act ctc tcg ctc gag aac aac acg acg acc gac aac ccg ctc ctc gac     1254
Thr Leu Ser Leu Glu Asn Asn Thr Thr Thr Asp Asn Pro Leu Leu Asp
                395                 400                 405 gtc gag aac aag cag acc gcg cac ggc ggc aac ttc cag gcg tcg gct     1302
Val Glu Asn Lys Gln Thr Ala His Gly Gly Asn Phe Gln Ala Ser Ala
            410                 415                 420 gtc tcg att tcg atg gag aag acc agg ctc gca ctc gcc ctc atc ggc     1350
Val Ser Ile Ser Met Glu Lys Thr Arg Leu Ala Leu Ala Leu Ile Gly
        425                 430                 435 aag ctc aac ttc acg cag tgc acc gag ttg ctc aac gct gcc atg aac     1398
Lys Leu Asn Phe Thr Gln Cys Thr Glu Leu Leu Asn Ala Ala Met Asn
440                 445                 450 cgc ggc ctg cct tcg tgc ctc gct gcc gag gac ccg tcg ctc aac tat     1446
Arg Gly Leu Pro Ser Cys Leu Ala Ala Glu Asp Pro Ser Leu Asn Tyr
455                 460                 465                 470 cac ggc aag ggc ttg gac att cac atc gct gct tac gct tcg gag ctc     1494
His Gly Lys Gly Leu Asp Ile His Ile Ala Ala Tyr Ala Ser Glu Leu
                475                 480                 485 ggc cac ctt gcc aac ccg gtc act acc ttc gtc cag ccc gca gag atg     1542
Gly His Leu Ala Asn Pro Val Thr Thr Phe Val Gln Pro Ala Glu Met
            490                 495                 500 ggc aac cag gcc gtc aac tcg ctc gct ctc atc tcc gcg cgc cgc act     1590
Gly Asn Gln Ala Val Asn Ser Leu Ala Leu Ile Ser Ala Arg Arg Thr
```

```
                505                 510                 515
gcc gag gcc aac gac gtc ctt tct ctc ctt ctc gcc tcg cac ctg tac      1638
Ala Glu Ala Asn Asp Val Leu Ser Leu Leu Leu Ala Ser His Leu Tyr
    520                 525                 530 tgc acg ctc cag gcc gtc gac ctc cgc gcg atg gag ctc gac ttc aag      1686
Cys Thr Leu Gln Ala Val Asp Leu Arg Ala Met Glu Leu Asp Phe Lys
535                 540                 545                 550 aag cag ttc gac ccg ctt ctc ccg act ctc ctc cag cag cac ctc ggc      1734
Lys Gln Phe Asp Pro Leu Leu Pro Thr Leu Leu Gln Gln His Leu Gly
                555                 560                 565 act ggc ctc gac gtc aac gca ctt gcg ctc gag gtc aag aag gcg ctc      1782
Thr Gly Leu Asp Val Asn Ala Leu Ala Leu Glu Val Lys Lys Ala Leu
            570                 575                 580 aac aag cgt ctc gag cag acg acg acg tac gac ctc gag ccg cgc tgg      1830
Asn Lys Arg Leu Glu Gln Thr Thr Thr Tyr Asp Leu Glu Pro Arg Trp
        585                 590                 595 cac gac gcc ttc tcg tac gcg acc ggc acc gtc gtc gag ctc ctc tcg      1878
His Asp Ala Phe Ser Tyr Ala Thr Gly Thr Val Val Glu Leu Leu Ser
    600                 605                 610 tcc tcg ccc tct gcc aac gtc acc ctt act gcc gtc aac gcg tgg aag      1926
Ser Ser Pro Ser Ala Asn Val Thr Leu Thr Ala Val Asn Ala Trp Lys
615                 620                 625                 630 gtt gcc tcg gcc gag aag gcc atc tcg ctc acg cgc gag gtg cgc aac      1974
Val Ala Ser Ala Glu Lys Ala Ile Ser Leu Thr Arg Glu Val Arg Asn
                635                 640                 645 cgc ttc tgg cag acg ccg tct tcg cag gcg ccg gcg cac gca tac ctc      2022
Arg Phe Trp Gln Thr Pro Ser Ser Gln Ala Pro Ala His Ala Tyr Leu
            650                 655                 660 tcg ccg cgc acg cgc gtc ctg tac tcg ttc gtg cgc gag gag ctc ggc      2070
Ser Pro Arg Thr Arg Val Leu Tyr Ser Phe Val Arg Glu Glu Leu Gly
        665                 670                 675 gtg cag gcg cgc cgc ggc gac gtg ttt gtc ggc gtg cag cag gag acg      2118
Val Gln Ala Arg Arg Gly Asp Val Phe Val Gly Val Gln Gln Glu Thr
    680                 685                 690 atc ggg agc aac gtc tcg cgc atc tac gag gcc atc aag gac ggc cgc      2166
Ile Gly Ser Asn Val Ser Arg Ile Tyr Glu Ala Ile Lys Asp Gly Arg
695                 700                 705                 710 atc aac cac gtc ctc gtc aag atg ctc gcg taaggcccga gcaagcctcg        2216
Ile Asn His Val Leu Val Lys Met Leu Ala
                715                 720 cctagacgcc cgcctcaccc caagaccagc ttttcgacgt cgtgtcgtgc caagaacgga    2276
ctttcctcca tacacatgtc gccttactct ctcgccgtca tcacgtctct cagttctttc    2336
gtatcccgcg tctctcggtc gtcagtacac gtgtatagag cctggaatgg attgcaagtc    2396
ttcgagttca aaaaaaaaaa aaa                                            2419

<210> SEQ ID NO 13
<211> LENGTH: 720
<212> TYPE: PRT
<213> ORGANISM: Rhodotorula graminis
<220> FEATURE:
<221> NAME/KEY: unsure
<222> LOCATION: (153)
<223> OTHER INFORMATION: Other information:  Xaa = Val or Ala

<400> SEQUENCE: 13

Met Ala Pro Ser Leu Asp Ser Leu Ala Thr Thr Leu Ala Asn Gly Phe
 1               5                  10                  15

Thr Asn Gly Ser His Ala Ala Pro Thr Lys Ser Ala Ala Gly Pro Thr
             20                  25                  30
```

```
Ser Ala Leu Arg Arg Thr Pro Gly Leu Asp Gly His Ala Ala His Gln
        35                  40                  45

Ser Gln Leu Glu Ile Val Gln Glu Leu Leu Ser Asp Pro Thr Asp Asp
    50                  55                  60

Val Val Glu Leu Ser Gly Tyr Ser Leu Thr Val Arg Asp Val Val Gly
 65                  70                  75                  80

Ala Ala Arg Lys Gly Arg Arg Val Arg Val Gln Asn Asp Asp Glu Ile
                85                  90                  95

Arg Ala Arg Val Asp Lys Ser Val Asp Phe Leu Lys Ala Gln Leu Gln
            100                 105                 110

Asn Ser Val Tyr Gly Val Thr Thr Gly Phe Gly Gly Ser Ala Asp Thr
        115                 120                 125

Arg Thr Glu Asp Ala Val Ser Leu Gln Lys Ala Leu Ile Glu His Gln
    130                 135                 140

Leu Cys Gly Val Thr Pro Thr Ser Xaa Ser Ser Phe Ser Val Gly Arg
145                 150                 155                 160

Gly Leu Glu Asn Thr Leu Pro Leu Glu Val Val Arg Gly Ala Met Val
                165                 170                 175

Ile Arg Val Asn Ser Leu Thr Arg Gly His Ser Ala Val Arg Leu Val
            180                 185                 190

Val Leu Glu Ala Leu Thr Asn Phe Leu Asn His Arg Ile Thr Pro Ile
        195                 200                 205

Val Pro Leu Arg Gly Ser Ile Ser Ala Ser Gly Asp Leu Ser Pro Leu
    210                 215                 220

Ser Tyr Ile Ala Gly Ala Ile Thr Gly His Pro Asp Val Lys Val His
225                 230                 235                 240

Val Leu His Glu Gly Thr Glu Lys Ile Met Phe Ala Arg Glu Ala Ile
                245                 250                 255

Ser Leu Phe Gly Leu Glu Ala Val Val Leu Gly Pro Lys Glu Gly Leu
            260                 265                 270

Gly Leu Val Asn Gly Thr Ala Val Ser Ala Ser Met Ala Thr Leu Ser
        275                 280                 285

Leu His Asp Ser His Met Leu Ser Leu Leu Ser Gln Ala Leu Thr Ala
    290                 295                 300

Leu Thr Val Glu Ala Met Val Gly Gln Gln Gly Ser Phe Ala Pro Phe
305                 310                 315                 320

Ile His Asp Val Cys Arg Pro His Pro Gly Gln Val Glu Val Ala Arg
                325                 330                 335

Asn Ile Arg Thr Leu Leu Ser Gly Ser Ser Phe Ala Val Glu His Glu
            340                 345                 350

Glu Glu Val Lys Val Lys Asp Asp Glu Gly Ile Leu Arg Gln Asp Arg
        355                 360                 365

Tyr Pro Leu Arg Thr Ser Pro Gln Phe Leu Gly Pro Leu Val Glu Asp
    370                 375                 380

Met Met His Ala Tyr Ser Thr Leu Ser Leu Glu Asn Asn Thr Thr Thr
385                 390                 395                 400

Asp Asn Pro Leu Leu Asp Val Glu Asn Lys Gln Thr Ala His Gly Gly
                405                 410                 415

Asn Phe Gln Ala Ser Ala Val Ser Ile Ser Met Glu Lys Thr Arg Leu
            420                 425                 430

Ala Leu Ala Leu Ile Gly Lys Leu Asn Phe Thr Gln Cys Thr Glu Leu
        435                 440                 445
```

```
Leu Asn Ala Ala Met Asn Arg Gly Leu Pro Ser Cys Leu Ala Glu
    450                 455                 460

Asp Pro Ser Leu Asn Tyr His Gly Lys Gly Leu Asp Ile His Ile Ala
465                 470                 475                 480

Ala Tyr Ala Ser Glu Leu Gly His Leu Ala Asn Pro Val Thr Thr Phe
                485                 490                 495

Val Gln Pro Ala Glu Met Gly Asn Gln Ala Val Asn Ser Leu Ala Leu
            500                 505                 510

Ile Ser Ala Arg Arg Thr Ala Glu Ala Asn Asp Val Leu Ser Leu Leu
        515                 520                 525

Leu Ala Ser His Leu Tyr Cys Thr Leu Gln Ala Val Asp Leu Arg Ala
    530                 535                 540

Met Glu Leu Asp Phe Lys Lys Gln Phe Asp Pro Leu Leu Pro Thr Leu
545                 550                 555                 560

Leu Gln Gln His Leu Gly Thr Gly Leu Asp Val Asn Ala Leu Ala Leu
                565                 570                 575

Glu Val Lys Lys Ala Leu Asn Lys Arg Leu Glu Gln Thr Thr Thr Tyr
            580                 585                 590

Asp Leu Glu Pro Arg Trp His Asp Ala Phe Ser Tyr Ala Thr Gly Thr
        595                 600                 605

Val Val Glu Leu Leu Ser Ser Ser Pro Ser Ala Asn Val Thr Leu Thr
    610                 615                 620

Ala Val Asn Ala Trp Lys Val Ala Ser Ala Glu Lys Ala Ile Ser Leu
625                 630                 635                 640

Thr Arg Glu Val Arg Asn Arg Phe Trp Gln Thr Pro Ser Ser Gln Ala
                645                 650                 655

Pro Ala His Ala Tyr Leu Ser Pro Arg Thr Arg Val Leu Tyr Ser Phe
            660                 665                 670

Val Arg Glu Glu Leu Gly Val Gln Ala Arg Arg Gly Asp Val Phe Val
        675                 680                 685

Gly Val Gln Gln Glu Thr Ile Gly Ser Asn Val Ser Arg Ile Tyr Glu
    690                 695                 700

Ala Ile Lys Asp Gly Arg Ile Asn His Val Leu Val Lys Met Leu Ala
705                 710                 715                 720

<210> SEQ ID NO 14
<211> LENGTH: 2311
<212> TYPE: DNA
<213> ORGANISM: Amanita muscaria
<220> FEATURE:
<221> NAME/KEY: CDS
<222> LOCATION: (18)..(2237)

<400> SEQUENCE: 14
gtcgctcgca aatctaa atg ggt ctc gat aac tcc aag aac act gcc aaa           50
                   Met Gly Leu Asp Asn Ser Lys Asn Thr Ala Lys
                    1               5                  10 ttt ttt gac cta cca aaa gcc gtc cat ggt atg aat ggt aca acc ccc          98
Phe Phe Asp Leu Pro Lys Ala Val His Gly Met Asn Gly Thr Thr Pro
            15                  20                  25 gtc aat ggt ttt aaa gcg aca gcg ctt tcc aag gcc tcc cga aca atg         146
Val Asn Gly Phe Lys Ala Thr Ala Leu Ser Lys Ala Ser Arg Thr Met
        30                  35                  40 acc aag act agc gca ctc tcg caa ttc tta gaa gcg tac cgt gaa ctc         194
Thr Lys Thr Ser Ala Leu Ser Gln Phe Leu Glu Ala Tyr Arg Glu Leu
    45                  50                  55 gag ggc tac aag aat ggt aga gcc atc aag gtt gac ggt caa acg tta         242
Glu Gly Tyr Lys Asn Gly Arg Ala Ile Lys Val Asp Gly Gln Thr Leu
```

-continued

| | | |
|---|---|---|
| Glu Gly Tyr Lys Asn Gly Arg Ala Ile Lys Val Asp Gly Gln Thr Leu<br>60                       65                     70                  75 | |
| tct att gca gcc gtc gct gca gct gct cgc tac aat gcg gcc gtt gag<br>Ser Ile Ala Ala Val Ala Ala Ala Ala Arg Tyr Asn Ala Ala Val Glu<br>                     80                     85                     90 | 290 |
| ttg gac gaa tcc cca ctt gtt aag gag cgc gtg agg aaa agt cag ctt<br>Leu Asp Glu Ser Pro Leu Val Lys Glu Arg Val Arg Lys Ser Gln Leu<br>                     95                    100                  105 | 338 |
| gct atc gca aac aaa gta tcg acc ggt gcc agc gta tac gga ctg tca<br>Ala Ile Ala Asn Lys Val Ser Thr Gly Ala Ser Val Tyr Gly Leu Ser<br>                  110                    115                  120 | 386 |
| act ggt ttc ggt ggc agt gct gat aca cgg acg gac aaa ccg atg ttg<br>Thr Gly Phe Gly Gly Ser Ala Asp Thr Arg Thr Asp Lys Pro Met Leu<br>125                       130                    135 | 434 |
| ttg ggg ttt gcc ctt ttg caa cac caa cat gta ggg ata ctg ccc acc<br>Leu Gly Phe Ala Leu Leu Gln His Gln His Val Gly Ile Leu Pro Thr<br>140                       145                    150                  155 | 482 |
| tcg act gag cct ttg gac gtc cta cct ctc caa gat gca aat aac aca<br>Ser Thr Glu Pro Leu Asp Val Leu Pro Leu Gln Asp Ala Asn Asn Thr<br>                  160                    165                  170 | 530 |
| agc atg cca gag gcg tgg att cgc ggg gcc att ttg atc cgt atg aat<br>Ser Met Pro Glu Ala Trp Ile Arg Gly Ala Ile Leu Ile Arg Met Asn<br>175                       180                    185 | 578 |
| tcg cta att cgt ggc cac tct gga atc aga tgg gag ttg atc gaa aag<br>Ser Leu Ile Arg Gly His Ser Gly Ile Arg Trp Glu Leu Ile Glu Lys<br>                  190                    195                  200 | 626 |
| atg aga gaa cta ctc gcg gcc aat gta ata cct gtc gtt ccc ctg aga<br>Met Arg Glu Leu Leu Ala Ala Asn Val Ile Pro Val Val Pro Leu Arg<br>205                       210                    215 | 674 |
| ggc agc atc tcc tca tcc gga gat ctg tct ccc cta tcc tat atc gca<br>Gly Ser Ile Ser Ser Ser Gly Asp Leu Ser Pro Leu Ser Tyr Ile Ala<br>220                       225                    230                  235 | 722 |
| ggc acg att att ggc aac cca tca atc aag gta tat cac ggt cca tca<br>Gly Thr Ile Ile Gly Asn Pro Ser Ile Lys Val Tyr His Gly Pro Ser<br>                  240                    245                  250 | 770 |
| aag tcc gga att cgc caa att gga tcc tcg aag gat gtc ttg gct ctg<br>Lys Ser Gly Ile Arg Gln Ile Gly Ser Ser Lys Asp Val Leu Ala Leu<br>                  255                    260                  265 | 818 |
| cat aat atc gaa cct ttc cca ctg gaa tcg aaa gaa cct ctt ggt att<br>His Asn Ile Glu Pro Phe Pro Leu Glu Ser Lys Glu Pro Leu Gly Ile<br>                  270                    275                  280 | 866 |
| ttg aat ggg acc gca ttc tcg gca tct gtg gca gct tta gcc cta aac<br>Leu Asn Gly Thr Ala Phe Ser Ala Ser Val Ala Ala Leu Ala Leu Asn<br>285                       290                    295 | 914 |
| gaa gct atc cat ctt gtc ttg ttg gct caa gtg tgc acg gct atg ggg<br>Glu Ala Ile His Leu Val Leu Leu Ala Gln Val Cys Thr Ala Met Gly<br>300                       305                    310                  315 | 962 |
| acc gag gca ttg ata ggc act cgc gct tct cat gca ccg ttc att cat<br>Thr Glu Ala Leu Ile Gly Thr Arg Ala Ser His Ala Pro Phe Ile His<br>                  320                    325                  330 | 1010 |
| gcc acc gca cga cca cat ccc ggt caa gta gaa tgt gct gag aac att<br>Ala Thr Ala Arg Pro His Pro Gly Gln Val Glu Cys Ala Glu Asn Ile<br>335                       340                    345 | 1058 |
| tgg aat ttg ctc gat ggg agt aaa ttg gct cag tta gaa gag cac gaa<br>Trp Asn Leu Leu Asp Gly Ser Lys Leu Ala Gln Leu Glu Glu His Glu<br>                  350                    355                  360 | 1106 |
| gtt cgc cta gaa gac gat aaa tac acc ctt cgg cag gac cgt tat cca<br>Val Arg Leu Glu Asp Asp Lys Tyr Thr Leu Arg Gln Asp Arg Tyr Pro<br>365                       370                    375 | 1154 |

-continued

| | |
|---|---|
| ctc cga act tcg cct caa ttc ctt ggg cct cag att gaa gac ata atc<br>Leu Arg Thr Ser Pro Gln Phe Leu Gly Pro Gln Ile Glu Asp Ile Ile<br>380                       385                           390                       395 | 1202 |
| tcc gct ttc cag act gta acg cag gag tgt aat tac tta cca gct act<br>Ser Ala Phe Gln Thr Val Thr Gln Glu Cys Asn Tyr Leu Pro Ala Thr<br>                   400                         405                     410 | 1250 |
| gac aat cca ctg att gat ggg gag act ggc gaa tct cac cac ggt ggc<br>Asp Asn Pro Leu Ile Asp Gly Glu Thr Gly Glu Ser His His Gly Gly<br>               415                       420                         425 | 1298 |
| aat ttc caa gcg atg gct gta act aat gca atg gag aag acg cga ctt<br>Asn Phe Gln Ala Met Ala Val Thr Asn Ala Met Glu Lys Thr Arg Leu<br>        430                       435                       440 | 1346 |
| gct tta cat cac gtt ggc aaa tta cta ttt tcc cag agc act gaa tta<br>Ala Leu His His Val Gly Lys Leu Leu Phe Ser Gln Ser Thr Glu Leu<br>445                       450                       455 | 1394 |
| gtc aat cct gcg atg aac cgc ggt ctg ccg cct tca gta gct gcc aca<br>Val Asn Pro Ala Met Asn Arg Gly Leu Pro Pro Ser Val Ala Ala Thr<br>460                       465                       470                     475 | 1442 |
| gat cca tct ctc aac tac cac gcc aaa gga cta gac ata gca act gcg<br>Asp Pro Ser Leu Asn Tyr His Ala Lys Gly Leu Asp Ile Ala Thr Ala<br>                   480                       485                       490 | 1490 |
| gcc tac gta gcc gaa gcg act cct ggc ccc act cac att cag tcg gca<br>Ala Tyr Val Ala Glu Ala Thr Pro Gly Pro Thr His Ile Gln Ser Ala<br>                   495                       500                     505 | 1538 |
| gaa atg cac aac caa gct gtt aac tcc ctg gcg ttg att tct gct cgg<br>Glu Met His Asn Gln Ala Val Asn Ser Leu Ala Leu Ile Ser Ala Arg<br>        510                       515                       520 | 1586 |
| gct acc atc aca tcg ttg gaa gtg cta aca tct ctg atc gcg tct tac<br>Ala Thr Ile Thr Ser Leu Glu Val Leu Thr Ser Leu Ile Ala Ser Tyr<br>525                       530                       535 | 1634 |
| ttg tat att cta tgc caa gct ctc gac ctc cgt gcc ctt cag cgc gag<br>Leu Tyr Ile Leu Cys Gln Ala Leu Asp Leu Arg Ala Leu Gln Arg Glu<br>540                       545                       550                     555 | 1682 |
| ttc ttg ccc ggt cta gac atc atc att cgt gag gag tta aga tcg tca<br>Phe Leu Pro Gly Leu Asp Ile Ile Ile Arg Glu Glu Leu Arg Ser Ser<br>                   560                       565                       570 | 1730 |
| ttt gga tct ttc ctg tca tca gaa cag atg gag aaa ttg caa caa aat<br>Phe Gly Ser Phe Leu Ser Ser Glu Gln Met Glu Lys Leu Gln Gln Asn<br>               575                       580                     585 | 1778 |
| cta act agt gca ttt gaa gat cat ctt gac aag acc acg aca atg gat<br>Leu Thr Ser Ala Phe Glu Asp His Leu Asp Lys Thr Thr Thr Met Asp<br>        590                       595                       600 | 1826 |
| aat act gat cga atg act acg atg gct gct aca tca tca tca gtt cta<br>Asn Thr Asp Arg Met Thr Thr Met Ala Ala Thr Ser Ser Ser Val Leu<br>605                       610                       615 | 1874 |
| ctt caa ttc ttt act gat tct ggc gcg tct gtt cct ccc tcg tct tgc<br>Leu Gln Phe Phe Thr Asp Ser Gly Ala Ser Val Pro Pro Ser Ser Cys<br>620                       625                       630                     635 | 1922 |
| gat ctt ctc tcc agt gtc tcg tcc ttc caa tct tct gtg gcg aca cgg<br>Asp Leu Leu Ser Ser Val Ser Ser Phe Gln Ser Ser Val Ala Thr Arg<br>                   640                       645                     650 | 1970 |
| tct tca gtt ctc atg gat gac cta cgg aaa gaa tat att ttt gga gac<br>Ser Ser Val Leu Met Asp Asp Leu Arg Lys Glu Tyr Ile Phe Gly Asp<br>               655                       660                     665 | 2018 |
| cgt ggc ccc acg ccc gca agc caa tac atc gga aag aca cgg cca gta<br>Arg Gly Pro Thr Pro Ala Ser Gln Tyr Ile Gly Lys Thr Arg Pro Val<br>        670                       675                       680 | 2066 |
| tac caa ttc att aga aca act ata ggc gtt cgt aag cat ggt tct gag<br>Tyr Gln Phe Ile Arg Thr Thr Ile Gly Val Arg Lys His Gly Ser Glu<br>685                       690                       695 | 2114 |

```
aac tac aac aag ttt tat aat ggg ctg ggt gtc gaa gac gtt acc atc        2162
Asn Tyr Asn Lys Phe Tyr Asn Gly Leu Gly Val Glu Asp Val Thr Ile
700                 705                 710                 715 ggt caa aat ata tca cgc ata tac gag tca atc cgg gac ggc aaa atg        2210
Gly Gln Asn Ile Ser Arg Ile Tyr Glu Ser Ile Arg Asp Gly Lys Met
            720                 725                 730 caa tcc att att gtc tcg ttg ttt gat taggtcttga aagcttgtat              2257
Gln Ser Ile Ile Val Ser Leu Phe Asp
            735                 740 cttattaata accatacact tcctcgaggt ctaaaaaaaa aaaaaaaaaa aaaa            2311

<210> SEQ ID NO 15
<211> LENGTH: 740
<212> TYPE: PRT
<213> ORGANISM: Amanita muscaria

<400> SEQUENCE: 15

Met Gly Leu Asp Asn Ser Lys Asn Thr Ala Lys Phe Phe Asp Leu Pro
 1               5                  10                  15

Lys Ala Val His Gly Met Asn Gly Thr Thr Pro Val Asn Gly Phe Lys
            20                  25                  30

Ala Thr Ala Leu Ser Lys Ala Ser Arg Thr Met Thr Lys Thr Ser Ala
        35                  40                  45

Leu Ser Gln Phe Leu Glu Ala Tyr Arg Glu Leu Glu Gly Tyr Lys Asn
    50                  55                  60

Gly Arg Ala Ile Lys Val Asp Gly Gln Thr Leu Ser Ile Ala Ala Val
65                  70                  75                  80

Ala Ala Ala Ala Arg Tyr Asn Ala Ala Val Glu Leu Asp Glu Ser Pro
                85                  90                  95

Leu Val Lys Glu Arg Val Arg Lys Ser Gln Leu Ala Ile Ala Asn Lys
            100                 105                 110

Val Ser Thr Gly Ala Ser Val Tyr Gly Leu Ser Thr Gly Phe Gly Gly
        115                 120                 125

Ser Ala Asp Thr Arg Thr Asp Lys Pro Met Leu Leu Gly Phe Ala Leu
    130                 135                 140

Leu Gln His Gln His Val Gly Ile Leu Pro Thr Ser Thr Glu Pro Leu
145                 150                 155                 160

Asp Val Leu Pro Leu Gln Asp Ala Asn Asn Thr Ser Met Pro Glu Ala
                165                 170                 175

Trp Ile Arg Gly Ala Ile Leu Ile Arg Met Asn Ser Leu Ile Arg Gly
            180                 185                 190

His Ser Gly Ile Arg Trp Glu Leu Ile Glu Lys Met Arg Glu Leu Leu
        195                 200                 205

Ala Ala Asn Val Ile Pro Val Pro Leu Arg Gly Ser Ile Ser Ser
    210                 215                 220

Ser Gly Asp Leu Ser Pro Leu Ser Tyr Ile Ala Gly Thr Ile Ile Gly
225                 230                 235                 240

Asn Pro Ser Ile Lys Val Tyr His Gly Pro Ser Lys Ser Gly Ile Arg
                245                 250                 255

Gln Ile Gly Ser Ser Lys Asp Val Leu Ala Leu His Asn Ile Glu Pro
            260                 265                 270

Phe Pro Leu Glu Ser Lys Glu Pro Leu Gly Ile Leu Asn Gly Thr Ala
        275                 280                 285

Phe Ser Ala Ser Val Ala Ala Leu Ala Leu Asn Glu Ala Ile His Leu
    290                 295                 300
```

-continued

```
Val Leu Leu Ala Gln Val Cys Thr Ala Met Gly Thr Glu Ala Leu Ile
305                 310                 315                 320

Gly Thr Arg Ala Ser His Ala Pro Phe Ile His Ala Thr Ala Arg Pro
                325                 330                 335

His Pro Gly Gln Val Glu Cys Ala Glu Asn Ile Trp Asn Leu Leu Asp
                340                 345                 350

Gly Ser Lys Leu Ala Gln Leu Glu Glu His Glu Val Arg Leu Glu Asp
            355                 360                 365

Asp Lys Tyr Thr Leu Arg Gln Asp Arg Tyr Pro Leu Arg Thr Ser Pro
        370                 375                 380

Gln Phe Leu Gly Pro Gln Ile Glu Asp Ile Ile Ser Ala Phe Gln Thr
385                 390                 395                 400

Val Thr Gln Glu Cys Asn Tyr Leu Pro Ala Thr Asp Asn Pro Leu Ile
                405                 410                 415

Asp Gly Glu Thr Gly Glu Ser His His Gly Gly Asn Phe Gln Ala Met
            420                 425                 430

Ala Val Thr Asn Ala Met Glu Lys Thr Arg Leu Ala Leu His His Val
        435                 440                 445

Gly Lys Leu Leu Phe Ser Gln Ser Thr Glu Leu Val Asn Pro Ala Met
    450                 455                 460

Asn Arg Gly Leu Pro Pro Ser Val Ala Ala Thr Asp Pro Ser Leu Asn
465                 470                 475                 480

Tyr His Ala Lys Gly Leu Asp Ile Ala Thr Ala Ala Tyr Val Ala Glu
                485                 490                 495

Ala Thr Pro Gly Pro Thr His Ile Gln Ser Ala Glu Met His Asn Gln
            500                 505                 510

Ala Val Asn Ser Leu Ala Leu Ile Ser Ala Arg Ala Thr Ile Thr Ser
        515                 520                 525

Leu Glu Val Leu Thr Ser Leu Ile Ala Ser Tyr Leu Tyr Ile Leu Cys
    530                 535                 540

Gln Ala Leu Asp Leu Arg Ala Leu Gln Arg Glu Phe Leu Pro Gly Leu
545                 550                 555                 560

Asp Ile Ile Ile Arg Glu Glu Leu Arg Ser Ser Phe Gly Ser Phe Leu
                565                 570                 575

Ser Ser Glu Gln Met Glu Lys Leu Gln Gln Asn Leu Thr Ser Ala Phe
            580                 585                 590

Glu Asp His Leu Asp Lys Thr Thr Thr Met Asp Asn Thr Asp Arg Met
        595                 600                 605

Thr Thr Met Ala Ala Thr Ser Ser Ser Val Leu Leu Gln Phe Phe Thr
    610                 615                 620

Asp Ser Gly Ala Ser Val Pro Pro Ser Ser Cys Asp Leu Leu Ser Ser
625                 630                 635                 640

Val Ser Ser Phe Gln Ser Ser Val Ala Thr Arg Ser Ser Val Leu Met
                645                 650                 655

Asp Asp Leu Arg Lys Glu Tyr Ile Phe Gly Asp Arg Gly Pro Thr Pro
            660                 665                 670

Ala Ser Gln Tyr Ile Gly Lys Thr Arg Pro Val Tyr Gln Phe Ile Arg
        675                 680                 685

Thr Thr Ile Gly Val Arg Lys His Gly Ser Glu Asn Tyr Asn Lys Phe
    690                 695                 700

Tyr Asn Gly Leu Gly Val Glu Asp Val Thr Ile Gly Gln Asn Ile Ser
705                 710                 715                 720
```

-continued

```
Arg Ile Tyr Glu Ser Ile Arg Asp Gly Lys Met Gln Ser Ile Ile Val
            725                 730                 735
Ser Leu Phe Asp
        740

<210> SEQ ID NO 16
<211> LENGTH: 2787
<212> TYPE: DNA
<213> ORGANISM: Rhodotorula mucilaginosa
<220> FEATURE:
<221> NAME/KEY: CDS
<222> LOCATION: (646)..(2784)

<400> SEQUENCE: 16
ctgcagaatc gccgcgacgt gacctagacc tctcttttcg ccctatcgcc ctctcgcaca      60
tatgtcctgt gccgcctttc tgtccctcct ggactgtatc atactctgtg gccccttgcc     120
tcggcttgtt cctctcctct atagacatgg gtactgatca cttcgtttgt tgttctcgtt     180
ttctcttgca agtacgaccc atcctttttt ctcgcgatcg acttcaatat cggtgcgctt     240
gcactacgtc tcttcgccag tgcacagtat gacgggaggg gacacgactg gcggcgaaag     300
cggagtcgtc gttgccggtc ccgagagacg ggaacacttt cttccgcctt ccagaggccg     360
tactccggtg atttgacatc gcactatgct tggtggggcg cccgaactcg gagcttgcga     420
tgtgcctgaa gcagagctcg gcaggcgaca tggcgactcc gccacattcg ggtcaaagcc     480
gaagtggggc ctcggacgtt ccgaacgtcg tcttgccgcc gccgcgttgc gtccgccgtc     540
gactttgtcc tcgtgtgctc acgcctcctt ctttctctct tctgctttcc tcacttcact     600
ctgcaagtcc cgcctcgcat ccacccaacc cgagcagctc tcaag atg gcc ccc tcc    657
                                                  Met Ala Pro Ser
                                                    1 gtc gac tcg atc gcg act tcg gtt gcc aac tcc ctc tcg aac ggg ttg     705
Val Asp Ser Ile Ala Thr Ser Val Ala Asn Ser Leu Ser Asn Gly Leu
  5                  10                  15                  20 cac gcc gcc gcc gcc gcc aac ggt ggc gac gtc cac aag aag acg gcc     753
His Ala Ala Ala Ala Ala Asn Gly Gly Asp Val His Lys Lys Thr Ala
              25                  30                  35 ggt gct ggc tcc ctc ctc ccg acc acc gag acg acc cag ctc gac atc     801
Gly Ala Gly Ser Leu Leu Pro Thr Thr Glu Thr Thr Gln Leu Asp Ile
          40                  45                  50 gtt gag cgc atc ttg gcc gac gcc ggc gcg acg gac cag atc aaa ctc     849
Val Glu Arg Ile Leu Ala Asp Ala Gly Ala Thr Asp Gln Ile Lys Leu
      55                  60                  65 gat ggg tac acc ctc acg ctc ggc gac gtc gtc ggc gct gct cgc cgt     897
Asp Gly Tyr Thr Leu Thr Leu Gly Asp Val Val Gly Ala Ala Arg Arg
  70                  75                  80 ggc cgc tcc gtc aag gtc gca gac agc ccg cac atc cgc gag aag atc     945
Gly Arg Ser Val Lys Val Ala Asp Ser Pro His Ile Arg Glu Lys Ile
 85                  90                  95                 100 gat gcc agt gtc gag ttc ctc cgt act cag ctc gac aac agt gtc tac     993
Asp Ala Ser Val Glu Phe Leu Arg Thr Gln Leu Asp Asn Ser Val Tyr
             105                 110                 115 ggt gtc acg act ggt ttc ggc ggc tcg gcc gac acc cgg act gag gat    1041
Gly Val Thr Thr Gly Phe Gly Gly Ser Ala Asp Thr Arg Thr Glu Asp
         120                 125                 130 gcg atc tcg ctc caa aag gcc ctg ctc gag cac cag ctc tgc ggt gtc    1089
Ala Ile Ser Leu Gln Lys Ala Leu Leu Glu His Gln Leu Cys Gly Val
     135                 140                 145 ctc ccc acc tcg atg gat ggc ttt gcg ctc ggt cgc ggc ctc gag aac    1137
Leu Pro Thr Ser Met Asp Gly Phe Ala Leu Gly Arg Gly Leu Glu Asn
```

```
                    150                 155                 160
tcg ctt ccg ctc gaa gtc gtc cga ggc gcg atg acc atc cgt gtc aac    1185
Ser Leu Pro Leu Glu Val Val Arg Gly Ala Met Thr Ile Arg Val Asn
165                 170                 175                 180 tcg ctc act cgc ggt cac tcg gcg gtc cgc atc gtc gtc ctc gaa gcc    1233
Ser Leu Thr Arg Gly His Ser Ala Val Arg Ile Val Val Leu Glu Ala
                    185                 190                 195 ctc acc aac ttc ctc aac cac ggc atc acc ccg atc gtc ccg ctt cga    1281
Leu Thr Asn Phe Leu Asn His Gly Ile Thr Pro Ile Val Pro Leu Arg
                200                 205                 210 ggc acc atc tcg gcg tcg ggc gac ctt tcc ccc ctc tct tac atc gcc    1329
Gly Thr Ile Ser Ala Ser Gly Asp Leu Ser Pro Leu Ser Tyr Ile Ala
            215                 220                 225 gcc tcg atc acc ggc cac ccg gac tcg aag gtc cac gtc gac ggc aag    1377
Ala Ser Ile Thr Gly His Pro Asp Ser Lys Val His Val Asp Gly Lys
        230                 235                 240 atc atg tcc gcc cag gag gcg atc gcg ctc aag ggt ctt cag ccc gtc    1425
Ile Met Ser Ala Gln Glu Ala Ile Ala Leu Lys Gly Leu Gln Pro Val
245                 250                 255                 260 gtc ctc ggt ccg aag gag ggt ctc ggt ctc gtc aac ggc acg gcc gtc    1473
Val Leu Gly Pro Lys Glu Gly Leu Gly Leu Val Asn Gly Thr Ala Val
                    265                 270                 275 tcc gcc tcg atg gcg acg ctg gcc ctc acc gac gca cac gtc ctc tcg    1521
Ser Ala Ser Met Ala Thr Leu Ala Leu Thr Asp Ala His Val Leu Ser
                280                 285                 290 ctc ctc gca cag gcg ctc act gct ctt act gtc gag gcc atg gtc gga    1569
Leu Leu Ala Gln Ala Leu Thr Ala Leu Thr Val Glu Ala Met Val Gly
            295                 300                 305 cac gcc ggc tcg ttc cac cca ttc ctc cac gac gtc acg cgc cct cac    1617
His Ala Gly Ser Phe His Pro Phe Leu His Asp Val Thr Arg Pro His
        310                 315                 320 ccg acc cag atc gag gtg gcg cgc aac atc cgg act ctt ctc gag ggc    1665
Pro Thr Gln Ile Glu Val Ala Arg Asn Ile Arg Thr Leu Leu Glu Gly
325                 330                 335                 340 agc aag tac gcc gtc cac cac gag act gaa gtc aag gtc aag gac gac    1713
Ser Lys Tyr Ala Val His His Glu Thr Glu Val Lys Val Lys Asp Asp
                    345                 350                 355 gag ggc atc ctc agg cag gac cgg tac ccg ctc cgc tgc tcg ccg cag    1761
Glu Gly Ile Leu Arg Gln Asp Arg Tyr Pro Leu Arg Cys Ser Pro Gln
                360                 365                 370 tgg ctc ggt ccc ctt gtc agc gac atg att cac gct cac gct gtc ctc    1809
Trp Leu Gly Pro Leu Val Ser Asp Met Ile His Ala His Ala Val Leu
            375                 380                 385 tcg ctc gag gct ggt cag tcg acc acc gac aac ccg ctg atc gac ctc    1857
Ser Leu Glu Ala Gly Gln Ser Thr Thr Asp Asn Pro Leu Ile Asp Leu
        390                 395                 400 gag aac aag atg acc cac cat ggc gga gcc ttc atg gcg agc agc gtc    1905
Glu Asn Lys Met Thr His His Gly Gly Ala Phe Met Ala Ser Ser Val
405                 410                 415                 420 gga aac acg atg gag aag act cgc ctc gcc gtc gcg ctg atg ggc aag    1953
Gly Asn Thr Met Glu Lys Thr Arg Leu Ala Val Ala Leu Met Gly Lys
                    425                 430                 435 gtc agc ttt act cag ctc acc gag atg ctc aac gcc ggc atg aac cgg    2001
Val Ser Phe Thr Gln Leu Thr Glu Met Leu Asn Ala Gly Met Asn Arg
                440                 445                 450 gcc ctt ccg tcc tgc ctc gct gcc gag gac cct tcc ctc tct tat cac    2049
Ala Leu Pro Ser Cys Leu Ala Ala Glu Asp Pro Ser Leu Ser Tyr His
            455                 460                 465 tgc aag ggt ctc gac att gct gcg gcc gcc tac act tcc gag ctc ggt    2097
```

-continued

| | | | | | | | | | | | | |
|---|---|---|---|---|---|---|---|---|---|---|---|---|
|Cys|Lys|Gly|Leu|Asp|Ile|Ala|Ala|Ala|Tyr|Thr|Ser|Glu|Leu|Gly|
| |470| | | |475| | | |480| | | |

```
cac ctt gcc aac ccg gtt tcg acc cac gtc cag ccg gcc gag atg ggc      2145
His Leu Ala Asn Pro Val Ser Thr His Val Gln Pro Ala Glu Met Gly
485                 490                 495                 500 aac cag gcc atc aac tcg ctc gcc ctc atc tcg gcc cgc cgc acc gcc      2193
Asn Gln Ala Ile Asn Ser Leu Ala Leu Ile Ser Ala Arg Arg Thr Ala
                505                 510                 515 gag gcg aac gac gtt ctc tcc ctc ctc gcc acc cac ctc tac tgc          2241
Glu Ala Asn Asp Val Leu Ser Leu Leu Leu Ala Thr His Leu Tyr Cys
            520                 525                 530 gtc ctc cag gcc gtc gac ctc cgc gcg atg gag ttt gag cac acc aag      2289
Val Leu Gln Ala Val Asp Leu Arg Ala Met Glu Phe Glu His Thr Lys
        535                 540                 545 gcg ttc gag ccg atg gtc act gag ctg ttg aag cag cac ttt ggc gcg      2337
Ala Phe Glu Pro Met Val Thr Glu Leu Leu Lys Gln His Phe Gly Ala
    550                 555                 560 ctc gcg acg gcc gaa gtc gag gac aag gtc cgc aag tcg atc tac aag      2385
Leu Ala Thr Ala Glu Val Glu Asp Lys Val Arg Lys Ser Ile Tyr Lys
565                 570                 575                 580 cgg ttg cag cag aac aac tcg tac gac ctc gag cag cgg tgg cac gac      2433
Arg Leu Gln Gln Asn Asn Ser Tyr Asp Leu Glu Gln Arg Trp His Asp
                585                 590                 595 acg ttc tcg gtc gcg acc ggt gcc gtc gtc gag gcg ctc gcc ggc cag      2481
Thr Phe Ser Val Ala Thr Gly Ala Val Val Glu Ala Leu Ala Gly Gln
            600                 605                 610 gag gtc tcg ctc gcg agc ctc aac gcc tgg aag gtc gcc tgc gcc gag      2529
Glu Val Ser Leu Ala Ser Leu Asn Ala Trp Lys Val Ala Cys Ala Glu
        615                 620                 625 aag gct atc gcg ctc acg cgc tcc gtc cgc gac tcg ttc tgg gcg gct      2577
Lys Ala Ile Ala Leu Thr Arg Ser Val Arg Asp Ser Phe Trp Ala Ala
    630                 635                 640 ccg tcg tcg tcg ccc gcg ctc aag tac ctc tcc ccg cgg acg cgc          2625
Pro Ser Ser Ser Ser Pro Ala Leu Lys Tyr Leu Ser Pro Arg Thr Arg
645                 650                 655                 660 gtc ctg tat tcg ttc gtc cgg gag gag gtc ggc gtc aag gcc cgc cgc      2673
Val Leu Tyr Ser Phe Val Arg Glu Glu Val Gly Val Lys Ala Arg Arg
                665                 670                 675 ggc gat gtc tac ctc ggc aag cag gag gtc acg atc ggc acc aac gtc      2721
Gly Asp Val Tyr Leu Gly Lys Gln Glu Val Thr Ile Gly Thr Asn Val
            680                 685                 690 agc cgc atc tac gag gcg atc aag agc ggt tgc atc gcc ccc gtc ctc      2769
Ser Arg Ile Tyr Glu Ala Ile Lys Ser Gly Cys Ile Ala Pro Val Leu
        695                 700                 705 gtc aag atg atg gca tag                                              2787
Val Lys Met Met Ala
    710

<210> SEQ ID NO 17
<211> LENGTH: 713
<212> TYPE: PRT
<213> ORGANISM: Rhodotorula mucilaginosa

<400> SEQUENCE: 17

Met Ala Pro Ser Val Asp Ser Ile Ala Thr Ser Val Ala Asn Ser Leu
1               5                   10                  15

Ser Asn Gly Leu His Ala Ala Ala Ala Asn Gly Gly Asp Val His
            20                  25                  30

Lys Lys Thr Ala Gly Ala Gly Ser Leu Leu Pro Thr Thr Glu Thr Thr
        35                  40                  45
```

-continued

```
Gln Leu Asp Ile Val Glu Arg Ile Leu Ala Asp Ala Gly Ala Thr Asp
 50                  55                  60

Gln Ile Lys Leu Asp Gly Tyr Thr Leu Thr Leu Gly Asp Val Val Gly
 65                  70                  75                  80

Ala Ala Arg Arg Gly Arg Ser Val Lys Val Ala Asp Ser Pro His Ile
                 85                  90                  95

Arg Glu Lys Ile Asp Ala Ser Val Glu Phe Leu Arg Thr Gln Leu Asp
            100                 105                 110

Asn Ser Val Tyr Gly Val Thr Thr Gly Phe Gly Gly Ser Ala Asp Thr
            115                 120                 125

Arg Thr Glu Asp Ala Ile Ser Leu Gln Lys Ala Leu Leu Glu His Gln
130                 135                 140

Leu Cys Gly Val Leu Pro Thr Ser Met Asp Gly Phe Ala Leu Gly Arg
145                 150                 155                 160

Gly Leu Glu Asn Ser Leu Pro Leu Glu Val Val Arg Gly Ala Met Thr
                165                 170                 175

Ile Arg Val Asn Ser Leu Thr Arg Gly His Ser Ala Val Arg Ile Val
            180                 185                 190

Val Leu Glu Ala Leu Thr Asn Phe Leu Asn His Gly Ile Thr Pro Ile
            195                 200                 205

Val Pro Leu Arg Gly Thr Ile Ser Ala Ser Gly Asp Leu Ser Pro Leu
210                 215                 220

Ser Tyr Ile Ala Ala Ser Ile Thr Gly His Pro Asp Ser Lys Val His
225                 230                 235                 240

Val Asp Gly Lys Ile Met Ser Ala Gln Glu Ala Ile Ala Leu Lys Gly
                245                 250                 255

Leu Gln Pro Val Val Leu Gly Pro Lys Glu Gly Leu Gly Leu Val Asn
            260                 265                 270

Gly Thr Ala Val Ser Ala Ser Met Ala Thr Leu Ala Leu Thr Asp Ala
            275                 280                 285

His Val Leu Ser Leu Leu Ala Gln Ala Leu Thr Ala Leu Thr Val Glu
290                 295                 300

Ala Met Val Gly His Ala Gly Ser Phe His Pro Phe Leu His Asp Val
305                 310                 315                 320

Thr Arg Pro His Pro Thr Gln Ile Glu Val Ala Arg Asn Ile Arg Thr
                325                 330                 335

Leu Leu Glu Gly Ser Lys Tyr Ala Val His His Glu Thr Glu Val Lys
            340                 345                 350

Val Lys Asp Asp Glu Gly Ile Leu Arg Gln Asp Arg Tyr Pro Leu Arg
            355                 360                 365

Cys Ser Pro Gln Trp Leu Gly Pro Leu Val Ser Asp Met Ile His Ala
370                 375                 380

His Ala Val Leu Ser Leu Glu Ala Gly Gln Ser Thr Thr Asp Asn Pro
385                 390                 395                 400

Leu Ile Asp Leu Glu Asn Lys Met Thr His His Gly Gly Ala Phe Met
                405                 410                 415

Ala Ser Ser Val Gly Asn Thr Met Glu Lys Thr Arg Leu Ala Val Ala
            420                 425                 430

Leu Met Gly Lys Val Ser Phe Thr Gln Leu Thr Glu Met Leu Asn Ala
            435                 440                 445

Gly Met Asn Arg Ala Leu Pro Ser Cys Leu Ala Ala Glu Asp Pro Ser
450                 455                 460
```

```
Leu Ser Tyr His Cys Lys Gly Leu Asp Ile Ala Ala Ala Tyr Thr
465                 470                 475                 480

Ser Glu Leu Gly His Leu Ala Asn Pro Val Ser Thr His Val Gln Pro
            485                 490                 495

Ala Glu Met Gly Asn Gln Ala Ile Asn Ser Leu Ala Leu Ile Ser Ala
            500                 505                 510

Arg Arg Thr Ala Glu Ala Asn Asp Val Leu Ser Leu Leu Ala Thr
515                 520                 525

His Leu Tyr Cys Val Leu Gln Ala Val Asp Leu Arg Ala Met Glu Phe
    530                 535                 540

Glu His Thr Lys Ala Phe Glu Pro Met Val Thr Glu Leu Leu Lys Gln
545                 550                 555                 560

His Phe Gly Ala Leu Ala Thr Ala Glu Val Glu Asp Lys Val Arg Lys
                565                 570                 575

Ser Ile Tyr Lys Arg Leu Gln Gln Asn Asn Ser Tyr Asp Leu Glu Gln
            580                 585                 590

Arg Trp His Asp Thr Phe Ser Val Ala Thr Gly Ala Val Val Glu Ala
    595                 600                 605

Leu Ala Gly Gln Glu Val Ser Leu Ala Ser Leu Asn Ala Trp Lys Val
610                 615                 620

Ala Cys Ala Glu Lys Ala Ile Ala Leu Thr Arg Ser Val Arg Asp Ser
625                 630                 635                 640

Phe Trp Ala Ala Pro Ser Ser Ser Pro Ala Leu Lys Tyr Leu Ser
                645                 650                 655

Pro Arg Thr Arg Val Leu Tyr Ser Phe Val Arg Glu Val Gly Val
            660                 665                 670

Lys Ala Arg Arg Gly Asp Val Tyr Leu Gly Lys Gln Glu Val Thr Ile
            675                 680                 685

Gly Thr Asn Val Ser Arg Ile Tyr Glu Ala Ile Lys Ser Gly Cys Ile
690                 695                 700

Ala Pro Val Leu Val Lys Met Met Ala
705                 710

<210> SEQ ID NO 18
<211> LENGTH: 2439
<212> TYPE: DNA
<213> ORGANISM: Rhodotorula toruloides
<220> FEATURE:
<221> NAME/KEY: CDS
<222> LOCATION: (1)..(2148)

<400> SEQUENCE: 18 atg gca ccc tcg ctc gac tcg atc tcg cac tcg ttc gca aac ggc gtc      48
Met Ala Pro Ser Leu Asp Ser Ile Ser His Ser Phe Ala Asn Gly Val
1               5                   10                  15 gca tcc gca aag cag gct gtc aat ggc gcc tcg acc aac ctc gca gtc      96
Ala Ser Ala Lys Gln Ala Val Asn Gly Ala Ser Thr Asn Leu Ala Val
                20                  25                  30 gca ggc tcg cac ctg ccc aca acc cag gtc acg cag gtc gac atc gtc     144
Ala Gly Ser His Leu Pro Thr Thr Gln Val Thr Gln Val Asp Ile Val
            35                  40                  45 gag aag atg ctc gcc gcg ccg acc gac tcg acg ctc gaa ctc gac ggc     192
Glu Lys Met Leu Ala Ala Pro Thr Asp Ser Thr Leu Glu Leu Asp Gly
        50                  55                  60 tac tcg ctc aac ctc gga gac gtc gtc tcg gcc gcg agg aag ggc agg     240
Tyr Ser Leu Asn Leu Gly Asp Val Val Ser Ala Ala Arg Lys Gly Arg
65                  70                  75                  80
```

```
cct gtc cgc gtc aag gac agc gac gag atc cgc tca aag att gac aaa      288
Pro Val Arg Val Lys Asp Ser Asp Glu Ile Arg Ser Lys Ile Asp Lys
             85                  90                  95 tcg gtc gag ttc ttg cgc tcc caa ctc tcc atg agc gtc tac ggc gtc      336
Ser Val Glu Phe Leu Arg Ser Gln Leu Ser Met Ser Val Tyr Gly Val
                100                 105                 110 acg act gga ttt ggc gga tcc gca gac acc cgc acc gag gac gcc atc      384
Thr Thr Gly Phe Gly Gly Ser Ala Asp Thr Arg Thr Glu Asp Ala Ile
            115                 120                 125 tcg ctc cag aag gct ctc ctc gag cac cag ctc tgc ggt gtt ctc cct      432
Ser Leu Gln Lys Ala Leu Leu Glu His Gln Leu Cys Gly Val Leu Pro
    130                 135                 140 tcg tcg ttc gac tcg ttc cgc ctc ggc cgc ggt ctc gag aac tcg ctt      480
Ser Ser Phe Asp Ser Phe Arg Leu Gly Arg Gly Leu Glu Asn Ser Leu
145                 150                 155                 160 ccc ctc gag gtt gtt cgc ggc gcc atg aca atc cgc gtc aac agc ttg      528
Pro Leu Glu Val Val Arg Gly Ala Met Thr Ile Arg Val Asn Ser Leu
                165                 170                 175 acc cgc ggc cac tcg gct gtc cgc ctc gtc gtc ctc gag gcg ctc acc      576
Thr Arg Gly His Ser Ala Val Arg Leu Val Val Leu Glu Ala Leu Thr
            180                 185                 190 aac ttc ctc aac cac ggc atc acc ccc atc gtc ccc ctc cgc ggc acc      624
Asn Phe Leu Asn His Gly Ile Thr Pro Ile Val Pro Leu Arg Gly Thr
        195                 200                 205 atc tct gcg tcg ggc gac ctc tct cct ctc tcc tac att gca gcg gcc      672
Ile Ser Ala Ser Gly Asp Leu Ser Pro Leu Ser Tyr Ile Ala Ala Ala
    210                 215                 220 atc agc ggt cac ccg gac agc aag gtg cac gtc gtc cac gag ggc aag      720
Ile Ser Gly His Pro Asp Ser Lys Val His Val Val His Glu Gly Lys
225                 230                 235                 240 gag aag atc ctg tac gcc cgc gag gcg atg gcg ctc ttc aac ctc gag      768
Glu Lys Ile Leu Tyr Ala Arg Glu Ala Met Ala Leu Phe Asn Leu Glu
                245                 250                 255 ccc gtc gtc ctc ggc ccg aag gaa ggt ctc ggt ctc gtc aac ggc acc      816
Pro Val Val Leu Gly Pro Lys Glu Gly Leu Gly Leu Val Asn Gly Thr
            260                 265                 270 gcc gtc tca gca tcg atg gcc acc ctc gct ctg cac gac gca cac atg      864
Ala Val Ser Ala Ser Met Ala Thr Leu Ala Leu His Asp Ala His Met
        275                 280                 285 ctc tcg ctc ctc tcg cag tcg ctc acg gcc atg acg gtc gaa gcg atg      912
Leu Ser Leu Leu Ser Gln Ser Leu Thr Ala Met Thr Val Glu Ala Met
    290                 295                 300 gtc ggc cac gcc ggc tcg ttc cac ccc ttc ctt cac gac gtc acg cgc      960
Val Gly His Ala Gly Ser Phe His Pro Phe Leu His Asp Val Thr Arg
305                 310                 315                 320 cct cac ccg acg cag atc gaa gtc gcg gga aac atc cgc aag ctc ctc     1008
Pro His Pro Thr Gln Ile Glu Val Ala Gly Asn Ile Arg Lys Leu Leu
                325                 330                 335 gag gga agc cgc ttt gct gtc cac cat gag gag gag gtc aag gtc aag     1056
Glu Gly Ser Arg Phe Ala Val His His Glu Glu Glu Val Lys Val Lys
            340                 345                 350 gac gac gag ggc att ctc cgc cag gac cgc tac ccc ttg cgc acg tct     1104
Asp Asp Glu Gly Ile Leu Arg Gln Asp Arg Tyr Pro Leu Arg Thr Ser
        355                 360                 365 cct cag tgg ctc ggc ccg ctc gtc agc gac ctc att cac gcc cac gcc     1152
Pro Gln Trp Leu Gly Pro Leu Val Ser Asp Leu Ile His Ala His Ala
    370                 375                 380 gtc ctc acc atc gag gcc ggc cag tcg acg acc gac aac cct ctc atc     1200
Val Leu Thr Ile Glu Ala Gly Gln Ser Thr Thr Asp Asn Pro Leu Ile
385                 390                 395                 400
```

-continued

| | |
|---|---|
| gac gtc gag aac aag act tcg cac cac ggc ggc aat ttc cag gct gcc<br>Asp Val Glu Asn Lys Thr Ser His His Gly Gly Asn Phe Gln Ala Ala<br>              405              410              415 | 1248 |
| gct gtg gcc aac acc atg gag aag act cgc ctc ggg ctc gcc cag atc<br>Ala Val Ala Asn Thr Met Glu Lys Thr Arg Leu Gly Leu Ala Gln Ile<br>       420               425              430 | 1296 |
| ggc aag ctc aac ttc acg cag ctc acc gag atg ctc aac gcc ggc atg<br>Gly Lys Leu Asn Phe Thr Gln Leu Thr Glu Met Leu Asn Ala Gly Met<br>              435              440              445 | 1344 |
| aac cgc ggc ctc ccc tcc tgc ctc gcg gcc gaa gac ccc tcg ctc tcc<br>Asn Arg Gly Leu Pro Ser Cys Leu Ala Ala Glu Asp Pro Ser Leu Ser<br>450              455              460 | 1392 |
| tac cac tgc aag ggc ctc gac atc gcc gct gcg gcg tac acc tcg gag<br>Tyr His Cys Lys Gly Leu Asp Ile Ala Ala Ala Ala Tyr Thr Ser Glu<br>465              470              475              480 | 1440 |
| ttg gga cac ctc gcc aac cct gtg acg acg cat gtc cag ccg gct gag<br>Leu Gly His Leu Ala Asn Pro Val Thr Thr His Val Gln Pro Ala Glu<br>              485              490              495 | 1488 |
| atg gcg aac cag gcg gtc aac tcg ctt gcg ctc atc tcg gct cgt cgc<br>Met Ala Asn Gln Ala Val Asn Ser Leu Ala Leu Ile Ser Ala Arg Arg<br>       500               505              510 | 1536 |
| acg acc gag tcc aac gac gtc ctt tct ctc ctc ctc gcc acc cac ctc<br>Thr Thr Glu Ser Asn Asp Val Leu Ser Leu Leu Leu Ala Thr His Leu<br>              515              520              525 | 1584 |
| tac tgc gtt ctc caa gcc atc gac ttg cgc gcg atc gag ttc gag ttc<br>Tyr Cys Val Leu Gln Ala Ile Asp Leu Arg Ala Ile Glu Phe Glu Phe<br>       530               535              540 | 1632 |
| aag aag cag ttc ggc cca gcc atc gtc tcg ctc atc gac cag cac ttt<br>Lys Lys Gln Phe Gly Pro Ala Ile Val Ser Leu Ile Asp Gln His Phe<br>545              550              555              560 | 1680 |
| ggc tcc gcc atg acc ggc tcg aac ctg cgc gac gag ctc gtc gag aag<br>Gly Ser Ala Met Thr Gly Ser Asn Leu Arg Asp Glu Leu Val Glu Lys<br>              565              570              575 | 1728 |
| gtg aac aag acg ctc gcc aag cgc ctc gag cag acc aac tcg tac gac<br>Val Asn Lys Thr Leu Ala Lys Arg Leu Glu Gln Thr Asn Ser Tyr Asp<br>       580               585              590 | 1776 |
| ctc gtc ccg cgc tgg cac gac gcc ttc tcc ttc gcc gcc ggc acc gtc<br>Leu Val Pro Arg Trp His Asp Ala Phe Ser Phe Ala Ala Gly Thr Val<br>              595              600              605 | 1824 |
| gtc gag gtc ctc tcg tcg acg tcg ctc tcg ctc gcc gcc gtc aac gcc<br>Val Glu Val Leu Ser Ser Thr Ser Leu Ser Leu Ala Ala Val Asn Ala<br>       610               615              620 | 1872 |
| tgg aag gtc gcc gcc gcc gag tcg gcc atc tcg ctc acc cgc caa gtc<br>Trp Lys Val Ala Ala Ala Glu Ser Ala Ile Ser Leu Thr Arg Gln Val<br>625              630              635              640 | 1920 |
| cgc gag acc ttc tgg tcc gcc gcg tcg acc tcg tcg ccc gcg ctc tcg<br>Arg Glu Thr Phe Trp Ser Ala Ala Ser Thr Ser Ser Pro Ala Leu Ser<br>              645              650              655 | 1968 |
| tac ctc tcg ccg cgc act cag atc ctc tac gcc ttc gtc cgc gag gag<br>Tyr Leu Ser Pro Arg Thr Gln Ile Leu Tyr Ala Phe Val Arg Glu Glu<br>       660               665              670 | 2016 |
| ctt ggc gtc aag gcc cgc cgc gga gac gtc ttc ctc ggc aag caa gag<br>Leu Gly Val Lys Ala Arg Arg Gly Asp Val Phe Leu Gly Lys Gln Glu<br>              675              680              685 | 2064 |
| gtg acg atc ggc tcg aac gtc tcc aag atc tac gag gcc atc aag tcg<br>Val Thr Ile Gly Ser Asn Val Ser Lys Ile Tyr Glu Ala Ile Lys Ser<br>690              695              700 | 2112 |
| ggc agg atc aac aac gtc ctc ctc aag atg ctc gct tagacactct<br>Gly Arg Ile Asn Asn Val Leu Leu Lys Met Leu Ala | 2158 |

-continued

```
                705                 710                 715
tcccactctc gcatcccttc cataccctat cccgcctgca ctcttaggac tcgcttcttg      2218
tcggactcgg atctcgcatc gcttctttcg ttcttggctg cctctctaga ccgtgtccgt      2278
attacctcga gattgtgaat acaagcagta cccatccacg catccgataa atcagggaga     2338
gaatctacgc ttgcgggagc ttcttgcgca taaactgtcg agtgcgggcg ttagtgcgaa      2398
gtcaacgaag gcgagtggca gcggctcact accgcctcga g                         2439
```

<210> SEQ ID NO 19
<211> LENGTH: 716
<212> TYPE: PRT
<213> ORGANISM: Rhodotorula toruloides

<400> SEQUENCE: 19

```
Met Ala Pro Ser Leu Asp Ser Ile Ser His Ser Phe Ala Asn Gly Val
 1               5                  10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320
```

```
Pro His Pro Thr Gln Ile Glu Val Ala Gly Asn Ile Arg Lys Leu Leu
            325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
            435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
            515                 520                 525

Tyr Cys Val Leu Gln Ala Ile Asp Leu Arg Ala Ile Glu Phe Glu Phe
            530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
            565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
    595                 600                 605

Val Glu Val Leu Ser Ser Thr Ser Leu Ser Leu Ala Ala Val Asn Ala
610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
            645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 20
<211> LENGTH: 2475
```

<212> TYPE: DNA
<213> ORGANISM: Artificial Sequence
<220> FEATURE:
<221> NAME/KEY: misc_difference
<222> LOCATION: (13) .. (2475)
<223> OTHER INFORMATION: n = A or C or G or T; "n" indicates no
      consensus at that position
<223> OTHER INFORMATION: Description of Artificial Sequence: Consensus
      Sequence of SEQ ID NOs: 12, 16, and 18

<400> SEQUENCE: 20

| | | | | | |
|---|---|---|---|---|---|
| atggccccct | ccntcgactc | gatcgcgacc | tcgntcgcca | acggcntcnc | naacggntng | 60 |
| cacgccgnnc | cgncnnngnc | gncacgggc | gccacgtcca | cnctcngncg | gccgncgcng | 120 |
| gctcgctcct | cccgaccacc | cagnngacgc | agctcgacat | cgtngagnag | atcctcgccg | 180 |
| accccaccgn | nacgnacgnn | ntcgaactcg | acgggtacac | cctcaccctc | ggngacgtcg | 240 |
| tcggcgccgc | ncgcaagggc | cgcncgtcc | gcgtcncaga | cagncgacga | gatccgcgca | 300 |
| aagatcgaca | anagngtcga | gttcctccgn | ncncagctcn | acaacagngt | ctacggngtc | 360 |
| acgactggtt | tcggcggctc | ggccgacacc | cggactgagg | atgcnatctc | gctccagaag | 420 |
| gcnctcctcg | agcaccagct | ctgcggtgtn | ctcccnacgt | cgntcgantc | cttcngcctc | 480 |
| ggncgcggcc | tcgagaactc | gcttccgctc | gaggtcgtcc | gcggcgccat | gaccatccgc | 540 |
| gtcaactcgc | tcacncgcgg | ccactcggcn | gtccgcctcg | tcgtcctcga | ggcgctcacc | 600 |
| aacttcctca | accacggcat | cacccccatc | gtcccctcc | gcggcaccat | ctcggcgtcg | 660 |
| ggcgacctct | cccnctctc | ntacatcgcc | gccgccatca | ccggtcaccc | ggacnncaag | 720 |
| gtncacgtnn | tncacgaggg | canngagaag | atcatgtncg | cccgcgaggc | gatcgcgctc | 780 |
| ttnggtctcg | agcccgtcgt | cctcggcccg | aaggagggtc | tcggtctcgt | caacggcacg | 840 |
| gccgtctccg | cctcgatggc | gaccctcgct | ctgcacgacg | cacacatgct | ctcgctcctc | 900 |
| tcgcaggcgc | tcacggctct | nacggtcgag | gccatggtcg | gccacgccgg | ctcgttccac | 960 |
| ccnttcctcc | acgacgtcac | gcgccctcac | ccgacccaga | tcgaggtcgc | gcgcaacatc | 1020 |
| cgcacgctcc | tcgagggcag | cnngtttgcc | gtccaccacg | aggaggaggt | caaggtcaag | 1080 |
| gacgacgagg | gcattctccg | ccaggaccgc | tacccgctcc | gcacgtcgcc | tcagtggctc | 1140 |
| ggcccgctcg | tcagcgacat | gattcacgcc | cacgcngtcc | tctcgctcga | ggccggncag | 1200 |
| tcgacgaccg | acaacccgct | catcgacgtc | gagaacaaga | ngacccacca | cggcggcaac | 1260 |
| ttccaggcgn | ccgctgtcgc | naacacgatg | gagaagactc | gcctcgcnct | cgccctgatc | 1320 |
| ggcaagctca | acttcacgca | gctcaccgag | atgctcaacg | ccggcatgaa | ccgcggcctn | 1380 |
| ccntcctgcc | tcgctgccga | ggacccntcg | ctctcctatc | actgcaaggg | cctcgacatt | 1440 |
| gccgcngcng | cntacacttc | ggagctcggn | caccttgcca | acccggtnac | gacccacgtc | 1500 |
| cagccggcng | agatgggcaa | ccaggccgtc | aactcgctcg | cnctcatctc | ggcncgccgc | 1560 |
| acngccgagg | ccaacgacgt | cctttctctc | ctcctcgcca | cccacctcta | ctgcgtnctc | 1620 |
| caggccgtcg | acctccgcgc | gatggagttc | gagttcaaga | agcagttcga | cccgntnntc | 1680 |
| ncnncgctcn | tcnagcagca | ctttggcncn | gccctcgacg | gcnnnnnnnn | nnnnnacgaa | 1740 |
| ctcgnggaca | aggtcaacaa | gncgctcnac | aagcgnctcg | agcagaccaa | ctcgtacgac | 1800 |
| ctcgagccgc | gctggcacga | cgccttctcg | ttcgcgaccg | gcaccgtcgt | cgagnnnnnn | 1860 |
| nngtcctcgc | cnnnngccan | naggtctcgc | tcgcngccgt | caacgcctgg | aaggtcgcct | 1920 |
| ccgccgagaa | ggccatctcg | ctcacgcgcn | angtccgcga | cnccttctgg | ncggcnccgt | 1980 |
| cgtcgtcgtc | gcccgcgctc | ncgtacctct | cgccgcgcac | gcgcgtcctg | tactcgttcg | 2040 |

-continued

```
tccgcgagga gctcggcgtc aaggcccgcc gcggcgacgt cttcctcggc aagcaggagg    2100
tgacgatcgg caccaacgtc tcccgcatct acgaggccat caagnncggc ngcatcaacc    2160
acgtcctcgt caagatgctc gcntagnnnc ncnnncnann ctcgcntnnn nnccnnncnc    2220
nnnccnnnnn nnnctnttng nnntcgnntc ntgncnnnnn cgganntnnc nncnnnnnnn    2280
tnnnncntnn ctnnctcncn nnnancnngt cnntnnnnnc tnnngnntnn nnnnncnnc     2340 ngtnnncann nacncntnnn nnnanncngg nanngantnn angnntcgn gnncnnnnnn     2400 nnnanaaann nnnnnnnnnn nnnnnnnnnn nnnnnnnnnn nnnnnnnnnn nnnnnnnnnn    2460
nnnnnnnnnn nnnnn                                                     2475
```

<210> SEQ ID NO 21
<211> LENGTH: 726
<212> TYPE: PRT
<213> ORGANISM: Artificial Sequence
<220> FEATURE:
<221> NAME/KEY: SITE
<222> LOCATION: (12)..(719)
<223> OTHER INFORMATION: "Xaa"means any amino acid;"Xaa"means no
    consensus at that position
<223> OTHER INFORMATION: Description of Artificial Sequence: Consensus
    of SEQ ID NOs: 13, 17, and 19

<400> SEQUENCE: 21

```
Met Ala Pro Ser Leu Asp Ser Ile Ala Thr Ser Xaa Ala Asn Gly Xaa
 1               5                  10                  15

Xaa Asn Gly Xaa His Ala Ala Xaa Xaa Ala Ser Xaa Xaa Xaa Xaa Xaa
            20                  25                  30

Xaa Xaa Xaa Xaa Ala Xaa Ala Gly Ser Xaa Leu Pro Thr Thr Xaa Xaa
        35                  40                  45

Thr Gln Leu Asp Ile Val Glu Xaa Xaa Leu Ala Asp Pro Xaa Thr Asp
    50                  55                  60

Asp Xaa Xaa Glu Leu Asp Gly Tyr Ser Leu Thr Leu Gly Asp Val Val
65                  70                  75                  80

Gly Ala Ala Arg Lys Gly Arg Xaa Val Arg Val Xaa Asp Ser Asp Glu
                85                  90                  95

Ile Arg Xaa Lys Ile Asp Lys Ser Val Glu Phe Leu Arg Xaa Gln Leu
            100                 105                 110

Xaa Asn Ser Val Tyr Gly Val Thr Thr Gly Phe Gly Gly Ser Ala Asp
        115                 120                 125

Thr Arg Thr Glu Asp Ala Ile Ser Leu Gln Lys Ala Leu Leu Glu His
    130                 135                 140

Gln Leu Cys Gly Val Leu Pro Thr Ser Xaa Asp Ser Phe Xaa Leu Gly
145                 150                 155                 160

Arg Gly Leu Glu Asn Ser Leu Pro Leu Glu Val Val Arg Gly Ala Met
                165                 170                 175

Thr Ile Arg Val Asn Ser Leu Thr Arg Gly His Ser Ala Val Arg Leu
            180                 185                 190

Val Val Leu Glu Ala Leu Thr Asn Phe Leu Asn His Gly Ile Thr Pro
        195                 200                 205

Ile Val Pro Leu Arg Gly Thr Ile Ser Ala Ser Gly Asp Leu Ser Pro
    210                 215                 220

Leu Ser Tyr Ile Ala Ala Ala Ile Thr Gly His Pro Asp Ser Lys Val
225                 230                 235                 240

His Val Xaa His Glu Gly Xaa Glu Lys Ile Met Xaa Ala Arg Glu Ala
                245                 250                 255
```

```
Ile Ala Leu Phe Gly Leu Glu Pro Val Val Leu Gly Pro Lys Glu Gly
            260                 265                 270

Leu Gly Leu Val Asn Gly Thr Ala Val Ser Ala Ser Met Ala Thr Leu
            275                 280                 285

Ala Leu His Asp Ala His Met Leu Ser Leu Ser Gln Ala Leu Thr
            290                 295                 300

Ala Leu Thr Val Glu Ala Met Val Gly His Ala Gly Ser Phe His Pro
305                 310                 315                 320

Phe Leu His Asp Val Thr Arg Pro His Pro Thr Gln Ile Glu Val Ala
                325                 330                 335

Arg Asn Ile Arg Thr Leu Leu Glu Gly Ser Xaa Phe Ala Val His His
                340                 345                 350

Glu Glu Glu Val Lys Val Lys Asp Glu Gly Ile Leu Arg Gln Asp
            355                 360                 365

Arg Tyr Pro Leu Arg Thr Ser Pro Gln Trp Leu Gly Pro Leu Val Ser
            370                 375                 380

Asp Met Ile His Ala His Ala Val Leu Ser Leu Glu Ala Gly Gln Ser
385                 390                 395                 400

Thr Thr Asp Asn Pro Leu Ile Asp Val Glu Asn Lys Xaa Thr His His
                405                 410                 415

Gly Gly Asn Phe Gln Ala Ser Ala Val Xaa Asn Thr Met Glu Lys Thr
                420                 425                 430

Arg Leu Ala Leu Ala Leu Ile Gly Lys Leu Asn Phe Thr Gln Leu Thr
            435                 440                 445

Glu Met Leu Asn Ala Gly Met Asn Arg Gly Leu Pro Ser Cys Leu Ala
            450                 455                 460

Ala Glu Asp Pro Ser Leu Ser Tyr His Cys Lys Gly Leu Asp Ile Ala
465                 470                 475                 480

Ala Ala Ala Tyr Thr Ser Glu Leu Gly His Leu Ala Asn Pro Val Thr
                485                 490                 495

Thr His Val Gln Pro Ala Glu Met Gly Asn Gln Ala Val Asn Ser Leu
            500                 505                 510

Ala Leu Ile Ser Ala Arg Arg Thr Ala Glu Ala Asn Asp Val Leu Ser
            515                 520                 525

Leu Leu Leu Ala Thr His Leu Tyr Cys Val Leu Gln Ala Val Asp Leu
            530                 535                 540

Arg Ala Met Glu Phe Glu Phe Lys Lys Gln Phe Xaa Pro Xaa Xaa Xaa
545                 550                 555                 560

Xaa Leu Leu Xaa Gln His Phe Gly Xaa Xaa Thr Xaa Xaa Xaa Xaa
            565                 570                 575

Xaa Xaa Glu Leu Xaa Xaa Lys Val Xaa Lys Xaa Leu Xaa Lys Arg Leu
            580                 585                 590

Glu Gln Thr Asn Ser Tyr Asp Leu Glu Pro Arg Trp His Asp Ala Phe
            595                 600                 605

Ser Xaa Ala Thr Gly Thr Val Val Glu Xaa Leu Ser Ser Xaa Xaa
            610                 615                 620

Xaa Xaa Val Ser Leu Ala Ala Val Asn Ala Trp Lys Val Ala Xaa Ala
625                 630                 635                 640

Glu Lys Ala Ile Ser Leu Thr Arg Xaa Val Arg Xaa Xaa Phe Trp Xaa
                645                 650                 655

Ala Pro Ser Ser Ser Pro Ala Leu Xaa Tyr Leu Ser Pro Arg Thr
                660                 665                 670
```

Arg Val Leu Tyr Ser Phe Val Arg Glu Glu Leu Gly Val Lys Ala Arg
            675                 680                 685

Arg Gly Asp Val Phe Leu Gly Lys Gln Glu Val Thr Ile Gly Ser Asn
        690                 695                 700

Val Ser Arg Ile Tyr Glu Ala Ile Lys Ser Gly Arg Ile Asn Xaa Val
705                 710                 715                 720

Leu Val Lys Met Leu Ala
                725

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic
      Primer OLI 74

<400> SEQUENCE: 22
atccatatgg ctccttcttt ggattctctt gctactacgc tcgccaacgg ctttacc      57

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      Primer OLI 75

<400> SEQUENCE: 23
atcgcggccg catgcggatc ctcattacgc gagcatcttg acgaggacgt ggttgatgcg   60

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer OLI 105

<400> SEQUENCE: 24
agtgaattca tggcccctte cttggactcg ctcgcca                            37

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer OLI 80

<400> SEQUENCE: 25
atcgcatgct cattacgcga gcatcttgac gaggacgtgg ttgatgcg                48

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: oli 89

<400> SEQUENCE: 26
taaaagatct ccaccatggc cccttccttg gactcgctc                          39

<210> SEQ ID NO 27
<211> LENGTH: 36

```
<212> TYPE: DNA
<213> ORGANISM: Artificial Sequence
<220> FEATURE:
<223> OTHER INFORMATION: Description of Artificial Sequence: oli 90

<400> SEQUENCE: 27
caagcggccg cagagacgcg ggatacgaaa gaactg                              36

<210> SEQ ID NO 28
<211> LENGTH: 2741
<212> TYPE: DNA
<213> ORGANISM: Rhodotorula graminis
<220> FEATURE:
<221> NAME/KEY: modified_base
<222> LOCATION: (6)
<223> OTHER INFORMATION: Description of modified_base: m = a or c
<221> NAME/KEY: exon
<222> LOCATION: (2008)..(2586)
<223> OTHER INFORMATION:
<221> NAME/KEY: exon
<222> LOCATION: (1822)..(1947)
<223> OTHER INFORMATION:
<221> NAME/KEY: exon
<222> LOCATION: (1587)..(1748)
<223> OTHER INFORMATION:
<221> NAME/KEY: exon
<222> LOCATION: (1365)..(1529)
<223> OTHER INFORMATION:
<221> NAME/KEY: exon
<222> LOCATION: (961)..(1295)
<223> OTHER INFORMATION:
<221> NAME/KEY: exon
<222> LOCATION: (449)..(880)
<223> OTHER INFORMATION:
<221> NAME/KEY: exon
<222> LOCATION: (1)..(361)
<223> OTHER INFORMATION:
<221> NAME/KEY: terminator
<222> LOCATION: (2587)..(2589)
<223> OTHER INFORMATION:
<221> NAME/KEY: Intron
<222> LOCATION: (1948)..(2007)
<223> OTHER INFORMATION:
<221> NAME/KEY: Intron
<222> LOCATION: (1749)..(1821)
<223> OTHER INFORMATION:
<221> NAME/KEY: Intron
<222> LOCATION: (1530)..(1586)
<223> OTHER INFORMATION:
<221> NAME/KEY: Intron
<222> LOCATION: (1296)..(1364)
<223> OTHER INFORMATION:
<221> NAME/KEY: Intron
<222> LOCATION: (881)..(960)
<223> OTHER INFORMATION:
<221> NAME/KEY: Intron
<222> LOCATION: (362)..(448)
<223> OTHER INFORMATION:

<400> SEQUENCE: 28 atg gcm cct tcc ttg gac tcg ctc gcc acc acg ctc gcc aac ggc ttt      48
Met Ala Pro Ser Leu Asp Ser Leu Ala Thr Thr Leu Ala Asn Gly Phe
1               5                   10                  15 acc aac ggc tcg cac gcc gct ccg acc aag tcg gct gcg ggc ccc act      96
Thr Asn Gly Ser His Ala Ala Pro Thr Lys Ser Ala Ala Gly Pro Thr
            20                  25                  30 tcg gct ctc cgc cgc acg ccc ggc ctc gat ggc cac gcc gcg cac cag     144
Ser Ala Leu Arg Arg Thr Pro Gly Leu Asp Gly His Ala Ala His Gln
        35                  40                  45 tcg cag ctc gag atc gtg cag gag ctc ctc agc gac ccc acc gac gac     192
Ser Gln Leu Glu Ile Val Gln Glu Leu Leu Ser Asp Pro Thr Asp Asp
    50                  55                  60
```

-continued

```
gtc gtc gag ctc agc ggg tac agc ctc acc gtc cgt gac gtt gtc ggc    240
Val Val Glu Leu Ser Gly Tyr Ser Leu Thr Val Arg Asp Val Val Gly
 65                  70                  75                  80 gcc gcc cgc aag ggg cgc agg gtc cgc gtc cag aac gac gac gag atc    288
Ala Ala Arg Lys Gly Arg Arg Val Arg Val Gln Asn Asp Asp Glu Ile
                 85                  90                  95 cgc gca cgc gtc gac aag agc gtc gac ttc ctc aag gcc cag ctt cag    336
Arg Ala Arg Val Asp Lys Ser Val Asp Phe Leu Lys Ala Gln Leu Gln
            100                 105                 110 aac tcg gtc tac gga gtc acc acg g tgcgttccga gacgagaggc            381
Asn Ser Val Tyr Gly Val Thr Thr
        115                 120 ggaaatctcg ggatgccgca gcgctgaacg ctgacactcg cttggacggc tgccgcggtc   441 ttgcagg gt ttc ggt ggc tcg gcc gac acg agg act gag gat gca gtc     489
        Gly Phe Gly Gly Ser Ala Asp Thr Arg Thr Glu Asp Ala Val
                        125                 130 agc ctc cag aag gcg ctc atc gag cac cag ctc tgc ggc gtg acg ccg    537
Ser Leu Gln Lys Ala Leu Ile Glu His Gln Leu Cys Gly Val Thr Pro
135                 140                 145                 150 acg tcc gtc tcg tcc ttc agc gtc gga cgc ggc ctc gag aac acg ctt    585
Thr Ser Val Ser Ser Phe Ser Val Gly Arg Gly Leu Glu Asn Thr Leu
                155                 160                 165 ccg ctc gag gtc gtc cgc ggc gcc atg gtc atc cgc gtc aac tcg ctc    633
Pro Leu Glu Val Val Arg Gly Ala Met Val Ile Arg Val Asn Ser Leu
            170                 175                 180 acg cgt ggc cac tcg gcc gtc cgc ctc gtc gtc ctt gag gcg ctc acc    681
Thr Arg Gly His Ser Ala Val Arg Leu Val Val Leu Glu Ala Leu Thr
        185                 190                 195 aac ttc ttg aac cac cgc atc acg ccc atc gtc ccc ctc cgc ggc tcc    729
Asn Phe Leu Asn His Arg Ile Thr Pro Ile Val Pro Leu Arg Gly Ser
200                 205                 210 atc tcg gcg tcg ggc gac ctc agc ccg ctc tcg tac atc gcc ggc gcc    777
Ile Ser Ala Ser Gly Asp Leu Ser Pro Leu Ser Tyr Ile Ala Gly Ala
215                 220                 225                 230 atc acc ggt cac ccc gac gtc aag gtt cac gtt ttg cac gag gga acc    825
Ile Thr Gly His Pro Asp Val Lys Val His Val Leu His Glu Gly Thr
                235                 240                 245 gag aag atc atg ttt gcg cgc gag gcc atc tcg ctc ttt ggt ctc gag    873
Glu Lys Ile Met Phe Ala Arg Glu Ala Ile Ser Leu Phe Gly Leu Glu
            250                 255                 260 gca gtc g gtacgtcgcg agtcctgact gcagtgagct gttcgagagt ctcccagttt   930
Ala Val gctgactgcc ctttgttcat gcgattgcag tc ctc ggc ccg aag gag ggt ctc    983
                                   Val Leu Gly Pro Lys Glu Gly Leu
                                                           270 ggt ctg gtc aac gga acg gcc gtc tcc gcc tcg atg gcg acc ctc agt    1031
Gly Leu Val Asn Gly Thr Ala Val Ser Ala Ser Met Ala Thr Leu Ser
        275                 280                 285 ctg cac gac tcg cac atg ctc tcg ctc ctc tcg cag gcc ttg acg gct    1079
Leu His Asp Ser His Met Leu Ser Leu Leu Ser Gln Ala Leu Thr Ala
        290                 295                 300 ctc acg gtg gag gcc atg gtc ggc cag cag ggc tcg ttc gcg ccg ttc    1127
Leu Thr Val Glu Ala Met Val Gly Gln Gln Gly Ser Phe Ala Pro Phe
305                 310                 315                 320 atc cac gac gtc tgc cgc ccg cac ccc ggc cag gtc gag gtc gcg cgc    1175
Ile His Asp Val Cys Arg Pro His Pro Gly Gln Val Glu Val Ala Arg
                325                 330                 335 aac atc cgc acg ctc ctt tcc ggc tcg tcg ttt gcc gtt gag cac gag    1223
Asn Ile Arg Thr Leu Leu Ser Gly Ser Ser Phe Ala Val Glu His Glu
```

|  |  |
|---|---|
| gag gag gtc aag gtc aag gac gac gag ggc att ctt cgc cag gac cgc<br>Glu Glu Val Lys Val Lys Asp Asp Glu Gly Ile Leu Arg Gln Asp Arg<br>355                      360                     365 | 1271 |
| tac ccg ctc cgc acg tcg cct cag gttcgtcccc tctctctccc cttccctccg<br>Tyr Pro Leu Arg Thr Ser Pro Gln<br>370                      375 | 1325 |
| tccgaccggc gcgtcgagac ttacgttttg cgtatccag ttc ctc ggc ccg ctc<br>                                                        Phe Leu Gly Pro Leu<br>                                                                      380 | 1379 |
| gtg gag gac atg atg cac gcc tac tcg act ctc tcg ctc gag aac aac<br>Val Glu Asp Met Met His Ala Tyr Ser Thr Leu Ser Leu Glu Asn Asn<br>                 385                      390                     395 | 1427 |
| acg acg acc gac aac ccg ctc ctc gac gtc gag aac aag cag acc gcg<br>Thr Thr Thr Asp Asn Pro Leu Leu Asp Val Glu Asn Lys Gln Thr Ala<br>            400                      405                      410 | 1475 |
| cac ggc ggc aac ttc cag gcg tcg gct gtc tcg att tcg atg gag aag<br>His Gly Gly Asn Phe Gln Ala Ser Ala Val Ser Ile Ser Met Glu Lys<br>    415                      420                      425 | 1523 |
| acc agg tgcgtctctc gctgccttcg tactccgatc ttgtgctgaa tgttcttctc<br>Thr Arg<br>430 | 1579 |
| ctgcagg ctc gca ctc gcc ctc atc ggc aag ctc aac ttc acg cag tgc<br>        Leu Ala Leu Ala Leu Ile Gly Lys Leu Asn Phe Thr Gln Cys<br>                                   435                      440                      445 | 1628 |
| acc gag ttg ctc aac gct gcc atg aac cgc ggc ctg cct tcg tgc ctc<br>Thr Glu Leu Leu Asn Ala Ala Met Asn Arg Gly Leu Pro Ser Cys Leu<br>              450                      455                      460 | 1676 |
| gct gcc gag gac ccg tcg ctc aac tat cac ggc aag ggc ttg gac att<br>Ala Ala Glu Asp Pro Ser Leu Asn Tyr His Gly Lys Gly Leu Asp Ile<br>        465                      470                      475 | 1724 |
| cac atc gct gct tac gct tcg gag gtgagccgtc gacgttctcc gccgtcgctc<br>His Ile Ala Ala Tyr Ala Ser Glu<br>        480                      485 | 1778 |
| gtccccttca gcgcacccag gctgacttcc tttccctctg tag ctc ggc cac ctt<br>                                                                       Leu Gly His Leu | 1833 |
| gcc aac ccg gtc act acc ttc gtc cag ccc gca gag atg ggc aac cag<br>Ala Asn Pro Val Thr Thr Phe Val Gln Pro Ala Glu Met Gly Asn Gln<br>490                      495                      500                      505 | 1881 |
| gcc gtc aac tcg ctc gct ctc atc tcc gcg cgc cgc act gcc gag gcc<br>Ala Val Asn Ser Leu Ala Leu Ile Ser Ala Arg Arg Thr Ala Glu Ala<br>              510                      515                      520 | 1929 |
| aac gac gtc ctt tct ctc gtgcgttcgt gtcgcaatga gtcccgacgc<br>Asn Asp Val Leu Ser Leu<br>              525 | 1977 |
| aatagcgact gactgcgcga tcctgagcag ctt ctc gcc tcg cac ctg tac tgc<br>                                                       Leu Leu Ala Ser His Leu Tyr Cys<br>                                                               530                      535 | 2031 |
| acg ctc cag gcc gtc gac ctc cgc gcg atg gag ctc gac ttc aag aag<br>Thr Leu Gln Ala Val Asp Leu Arg Ala Met Glu Leu Asp Phe Lys Lys<br>              540                      545                      550 | 2079 |
| cag ttc gac ccg ctt ctc ccg act ctc ctc cag cag cac ctc ggc act<br>Gln Phe Asp Pro Leu Leu Pro Thr Leu Leu Gln Gln His Leu Gly Thr<br>        555                      560                      565 | 2127 |
| ggc ctc gac gtc aac gca ctt gcg ctc gag gtc aag aag gcg ctc aac<br>Gly Leu Asp Val Asn Ala Leu Ala Leu Glu Val Lys Lys Ala Leu Asn<br>    570                      575                      580 | 2175 |
| aag cgt ctc gag cag acg acg acg tac gac ctc gag ccg cgc tgg cac | 2223 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Lys | Arg | Leu | Glu | Gln | Thr | Thr | Thr | Tyr | Asp | Leu | Glu | Pro | Arg | Trp | His |     |
|     | 585 |     |     |     |     | 590 |     |     |     |     | 595 |     |     |     |     |     |

```
gac gcc ttc tcg tac gcg acc ggc acc gtc gtc gag ctc ctc tcg tcc         2271
Asp Ala Phe Ser Tyr Ala Thr Gly Thr Val Val Glu Leu Leu Ser Ser
600                 605                 610                 615 tcg ccc tct gcc aac gtc acc ctt act gcc gtc aac gcg tgg aag gtt         2319
Ser Pro Ser Ala Asn Val Thr Leu Thr Ala Val Asn Ala Trp Lys Val
            620                 625                 630 gcc tcg gcc gag aag gcc atc tcg ctc acg cgc gag gtg cgc aac cgc         2367
Ala Ser Ala Glu Lys Ala Ile Ser Leu Thr Arg Glu Val Arg Asn Arg
                635                 640                 645 ttc tgg cag acg ccg tct tcg cag gcg ccg gcg cac gca tac ctc tcg         2415
Phe Trp Gln Thr Pro Ser Ser Gln Ala Pro Ala His Ala Tyr Leu Ser
            650                 655                 660 ccg cgc acg cgc gtc ctg tac tcg ttc gtg cgc gag gag ctc ggc gtg         2463
Pro Arg Thr Arg Val Leu Tyr Ser Phe Val Arg Glu Glu Leu Gly Val
665                 670                 675 cag gcg cgc cgc ggc gac gtg ttt gtc ggc gtg cag cag gag acg atc         2511
Gln Ala Arg Arg Gly Asp Val Phe Val Gly Val Gln Gln Glu Thr Ile
680                 685                 690                 695 ggg agc aac gtc tcg cgc atc tac gag gcc atc aag gac ggc cgc atc         2559
Gly Ser Asn Val Ser Arg Ile Tyr Glu Ala Ile Lys Asp Gly Arg Ile
                700                 705                 710 aac cac gtc ctc gtc aag atg ctc gcg taaggcccga gcaagcctcg               2606
Asn His Val Leu Val Lys Met Leu Ala
            715                 720 cctagacgcc cgcctcaccc caagaccagc ttttcgacgt cgtgtcgtgc caagaacgga       2666
cttccctcca tacacatgtc gtcttactct ctcgccgtca tcacgtctct cagttctttc       2726
gtatcccgcg tctct                                                        2741
```

<210> SEQ ID NO 29
<211> LENGTH: 2163
<212> TYPE: DNA
<213> ORGANISM: Artificial Sequence
<220> FEATURE:
<223> OTHER INFORMATION: Description of Artificial Sequence:   Preferred
      theoretical sequence based in part on SEQ ID NO:20
<221> NAME/KEY: CDS
<222> LOCATION: (1)..(2163)
<223> OTHER INFORMATION:

<400> SEQUENCE: 29

```
atg gcc ccc tcc btc gac tcg atc gcg acc tcg btc gcc aac ggc btc          48
Met Ala Pro Ser Xaa Asp Ser Ile Ala Thr Ser Xaa Ala Asn Gly Xaa
1               5                   10                  15 dcv aac ggv thg cac gcc gct ccg hcc aag ycg scw acg ggc gcc acg          96
Xaa Asn Xaa Xaa His Ala Ala Pro Xaa Lys Xaa Xaa Thr Gly Ala Thr
                20                  25                  30 tcc ach ctc mgm cgg ccg bcc dgg ctc gct cct ccc gcc acc cag vhg         144
Ser Xaa Leu Xaa Arg Pro Xaa Xaa Leu Ala Pro Pro Ala Thr Gln Xaa
            35                  40                  45 acg cag ctc gac atc gtb gag vag atc ctc gcc gac ccc acc gac gac         192
Thr Gln Leu Asp Ile Xaa Glu Xaa Ile Leu Ala Asp Pro Thr Asp Asp
50                  55                  60 gws vtc gaa ctc gac ggg tac acc ctc acc ctc ggh gac gtc gtc ggc         240
Xaa Xaa Glu Leu Asp Gly Tyr Thr Leu Thr Leu Xaa Asp Val Val Gly
65                  70                  75                  80 gcc gcb cgc aag ggc cgc hcb gtc cgc gtc cag aca gmc gac gag atc         288
Ala Ala Arg Lys Gly Arg Xaa Val Arg Val Gln Thr Xaa Asp Glu Ile
                85                  90                  95
```

-continued

| | |
|---|---|
| cgc gca aag atc gac aav agb gtc gag ttc ctc cgb dcb cag ctc bac<br>Arg Ala Lys Ile Asp Xaa Xaa Val Glu Phe Leu Arg Xaa Gln Leu Xaa<br>              100                    105                    110 | 336 |
| aac agb gtc tac ggh gtc acg act ggt ttc ggc ggc tcg gcc gac acc<br>Asn Xaa Val Tyr Xaa Val Thr Thr Gly Phe Gly Gly Ser Ala Asp Thr<br>       115                    120                    125 | 384 |
| cgg act gag gat gcv atc tcg ctc cag aag gcb ctc ctc gag cac cag<br>Arg Thr Glu Asp Ala Ile Ser Leu Gln Lys Ala Leu Leu Glu His Gln<br>130                    135                    140 | 432 |
| ctc tgc ggt gtb ctc ccb acg tcg dtc gab tcc ttc vgc ctc ggh cgc<br>Leu Cys Gly Xaa Leu Xaa Thr Ser Xaa Xaa Ser Phe Xaa Leu Xaa Arg<br>145                    150                    155                    160 | 480 |
| ggc ctc gag aac tcg ctt ccg ctc gag gtc gtc cgc ggc gcc atg acc<br>Gly Leu Glu Asn Ser Leu Pro Leu Glu Val Val Arg Gly Ala Met Thr<br>                  165                    170                    175 | 528 |
| atc cgc gtc aac tcg ctc acb cgc ggc cac tcg gcb gtc cgc ctc gtc<br>Ile Arg Val Asn Ser Leu Xaa Arg Gly His Ser Ala Val Arg Leu Val<br>                  180                    185                    190 | 576 |
| gtc ctc gag gcg ctc acc aac ttc ctc aac cac ggc atc acc ccc atc<br>Val Leu Glu Ala Leu Thr Asn Phe Leu Asn His Gly Ile Thr Pro Ile<br>          195                    200                    205 | 624 |
| gtc ccc ctc cgc ggc acc atc tcg gcg tcg ggc gac ctc tcc ccb ctc<br>Val Pro Leu Arg Gly Thr Ile Ser Ala Ser Gly Asp Leu Ser Xaa Leu<br>210                    215                    220 | 672 |
| tcb tac atc gcc gcc gcc atc acc ggt cac ccg gac dbc aag gtb cac<br>Xaa Tyr Ile Ala Ala Ala Ile Thr Gly His Pro Asp Xaa Lys Xaa His<br>225                    230                    235                    240 | 720 |
| gty kts cac gag ggc ams gag aag atc atg thc gcc cgc gag gcg atc<br>Xaa Xaa His Glu Gly Xaa Glu Lys Ile Met Xaa Ala Arg Glu Ala Ile<br>                  245                    250                    255 | 768 |
| gcg ctc ttb ggt ctc gag ccc gtc gtc ctc ggc ccg aag gag ggt ctc<br>Ala Leu Xaa Gly Leu Glu Pro Val Val Leu Gly Pro Lys Glu Gly Leu<br>                  260                    265                    270 | 816 |
| ggt ctc gtc aac ggc acg gcc gtc tcc gcc tcg atg gcg acc ctc gct<br>Gly Leu Val Asn Gly Thr Ala Val Ser Ala Ser Met Ala Thr Leu Ala<br>       275                    280                    285 | 864 |
| ctg cac gac gca cac atg ctc tcg ctc ctc tcg cag gcg ctc acg gct<br>Leu His Asp Ala His Met Leu Ser Leu Leu Ser Gln Ala Leu Thr Ala<br>290                    295                    300 | 912 |
| ctb acg gtc gag gcc atg gtc ggc cac gcc ggc tcg ttc cac ccv ttc<br>Xaa Thr Val Glu Ala Met Val Gly His Ala Gly Ser Phe His Xaa Phe<br>305                    310                    315                    320 | 960 |
| ctc cac gac gtc acg cgc cct cac ccg acc cag atc gag gtc gcg cgc<br>Leu His Asp Val Thr Arg Pro His Pro Thr Gln Ile Glu Val Ala Arg<br>                  325                    330                    335 | 1008 |
| aac atc cgc acg ctc ctc gag ggc agc hvg ttt gcc gtc cac cac gag<br>Asn Ile Arg Thr Leu Leu Glu Gly Ser Xaa Phe Ala Val His His Glu<br>              340                    345                    350 | 1056 |
| gag gag gtc aag gtc aag gac gac gag ggc att ctc cgc cag gac cgc<br>Glu Glu Val Lys Val Lys Asp Asp Glu Gly Ile Leu Arg Gln Asp Arg<br>       355                    360                    365 | 1104 |
| tac ccg ctc cgc acg tcg cct cag tgg ctc ggc ccg ctc gtc agc gac<br>Tyr Pro Leu Arg Thr Ser Pro Gln Trp Leu Gly Pro Leu Val Ser Asp<br>370                    375                    380 | 1152 |
| atg att cac gcc cac gcb gtc ctc tcg ctc gag gcc gag tcg acg acc<br>Met Ile His Ala His Ala Val Leu Ser Leu Glu Ala Glu Ser Thr Thr<br>385                    390                    395                    400 | 1200 |
| gac aac ccg ctc atc gac gtc gag aac aag ahg acc cac cac ggc ggc<br>Asp Asn Pro Leu Ile Asp Val Glu Asn Lys Xaa Thr His His Gly Gly<br>                  405                    410                    415 | 1248 |

```
                                                    -continued aac ttc cag gcg dcc gct gtc gcv aac acg atg gag aag act cgc ctc    1296
Asn Phe Gln Ala Xaa Ala Val Ala Asn Thr Met Glu Lys Thr Arg Leu
            420                 425                 430 gcv ctc gcc ctg atc ggc aag ctc aac ttc acg cag ctc acc gag atg    1344
Ala Leu Ala Leu Ile Gly Lys Leu Asn Phe Thr Gln Leu Thr Glu Met
                435                 440                 445 ctc aac gcc ggc atg aac cgc ggc ctb ccb tcc tgc ctc gct gcc gag    1392
Leu Asn Ala Gly Met Asn Arg Gly Xaa Xaa Ser Cys Leu Ala Ala Glu
        450                 455                 460 gac ccb tcg ctc tcc tat cac tgc aag ggc ctc gac att gcc gcb gcb    1440
Asp Xaa Ser Leu Ser Tyr His Cys Lys Gly Leu Asp Ile Ala Ala Ala
465                 470                 475                 480 gcb tac act tcg gag ctc ggh cac ctt gcc aac ccg gtb acg acc cac    1488
Ala Tyr Thr Ser Glu Leu Xaa His Leu Ala Asn Pro Xaa Thr Thr His
                485                 490                 495 gtc cag ccg gch gag atg ggc aac cag gcc gtc aac tcg ctc gcb ctc    1536
Val Gln Pro Arg Glu Met Gly Asn Gln Ala Val Asn Ser Leu Ala Leu
            500                 505                 510 atc tcg gcb cgc cgc acb gcc gag gcc aac gac gtc ctt tct ctc ctc    1584
Ile Ser Ala Arg Arg Xaa Ala Glu Ala Asn Asp Val Leu Ser Leu Leu
        515                 520                 525 ctc gcc acc cac ctc tac tgc gtb ctc cag gcc gtc gac ctc cgc gcg    1632
Leu Ala Thr His Leu Tyr Cys Xaa Leu Gln Ala Val Asp Leu Arg Ala
530                 535                 540 atg gag ttc gag ttc aag aag cag ttc gac ccg vtb vtc vcb dcg ctc    1680
Met Glu Phe Glu Phe Lys Lys Gln Phe Asp Pro Xaa Xaa Xaa Xaa Leu
545                 550                 555                 560 htc vag cag cac ttt ggc dcy gcc ctc gac ggc wac gaa ctc ghg gac    1728
Xaa Xaa Gln His Phe Gly Xaa Ala Leu Asp Gly Xaa Glu Leu Xaa Asp
                565                 570                 575 aag gtc aac aag dcg ctc dac aag cgb ctc gag cag acc aac tcg tac    1776
Lys Val Asn Lys Xaa Leu Xaa Lys Arg Leu Glu Gln Thr Asn Ser Tyr
            580                 585                 590 gac ctc gag ccg cgc tgg cac gac gcc ttc tcg ttc gcg acc ggc acc    1824
Asp Leu Glu Pro Arg Trp His Asp Ala Phe Ser Phe Ala Thr Gly Thr
        595                 600                 605 gtc gtc gag ctc ctc tcg tcc tcg ccb yct gcc aag gtc tcg ctc gcb    1872
Val Val Glu Leu Leu Ser Ser Ser Xaa Xaa Ala Lys Val Ser Leu Ala
    610                 615                 620 gcc gtc aac gcc tgg aag gtc gcc tcc gcc gag aag gcc atc tcg ctc    1920
Ala Val Asn Ala Trp Lys Val Ala Ser Ala Glu Lys Ala Ile Ser Leu
625                 630                 635                 640 acg cgc bav gtc cgc gac hcc ttc tgg bcg gcb ccg tcg tcg tcg tcg    1968
Thr Arg Xaa Val Arg Asp Xaa Phe Trp Xaa Ala Pro Ser Ser Ser Ser
                645                 650                 655 ccc gcg ctc dcg tac ctc tcg ccg cgc acg cgc gtc ctg tac tcg ttc    2016
Pro Ala Leu Xaa Tyr Leu Ser Pro Arg Thr Arg Val Leu Tyr Ser Phe
            660                 665                 670 gtc cgc gag gag ctc ggc gtc aag gcc cgc cgc ggc gac gtc ttc ctc    2064
Val Arg Glu Glu Leu Gly Val Lys Ala Arg Arg Gly Asp Val Phe Leu
        675                 680                 685 ggc aag cag gag gtg acg atc ggc acc aac gtc tcc cgc atc tac gag    2112
Gly Lys Gln Glu Val Thr Ile Gly Thr Asn Val Ser Arg Ile Tyr Glu
    690                 695                 700 gcc atc aag dvc ggc hgc atc aac cac gtc ctc gtc aag atg ctc gcd    2160
Ala Ile Lys Xaa Gly Xaa Ile Asn His Val Leu Val Lys Met Leu Ala
705                 710                 715                 720 tag                                                                2163
```

```
<210> SEQ ID NO 30
<211> LENGTH: 720
<212> TYPE: PRT
<213> ORGANISM: Artificial Sequence
<220> FEATURE:
<223> OTHER INFORMATION: Description of Artificial Sequence:   Preferred
      theoretical sequence based in part on SEQ ID NO:20
<221> NAME/KEY: misc_feature
<222> LOCATION: (5)..(5)
<223> OTHER INFORMATION: The 'Xaa' at location 5 stands for Val, Leu, or
      Phe.
<221> NAME/KEY: misc_feature
<222> LOCATION: (12)..(12)
<223> OTHER INFORMATION: The 'Xaa' at location 12 stands for Val, Leu,
      or Phe.
<221> NAME/KEY: misc_feature
<222> LOCATION: (16)..(16)
<223> OTHER INFORMATION: The 'Xaa' at location 16 stands for Val, Leu,
      or Phe.
<221> NAME/KEY: misc_feature
<222> LOCATION: (17)..(17)
<223> OTHER INFORMATION: The 'Xaa' at location 17 stands for Thr, Ala,
      or Ser.
<221> NAME/KEY: misc_feature
<222> LOCATION: (19)..(19)
<223> OTHER INFORMATION: The 'Xaa' at location 19 stands for Gly.
<221> NAME/KEY: misc_feature
<222> LOCATION: (20)..(20)
<223> OTHER INFORMATION: The 'Xaa' at location 20 stands for a stop
      codon, Ser, or Leu.
<221> NAME/KEY: misc_feature
<222> LOCATION: (25)..(25)
<223> OTHER INFORMATION: The 'Xaa' at location 25 stands for Thr, Pro,
      or Ser.
<221> NAME/KEY: misc_feature
<222> LOCATION: (27)..(27)
<223> OTHER INFORMATION: The 'Xaa' at location 27 stands for Pro, or
      Ser.
<221> NAME/KEY: misc_feature
<222> LOCATION: (28)..(28)
<223> OTHER INFORMATION: The 'Xaa' at location 28 stands for Ala, or
      Pro.
<221> NAME/KEY: misc_feature
<222> LOCATION: (34)..(34)
<223> OTHER INFORMATION: The 'Xaa' at location 34 stands for Thr.
<221> NAME/KEY: misc_feature
<222> LOCATION: (36)..(36)
<223> OTHER INFORMATION: The 'Xaa' at location 36 stands for Arg, or
      Ser.
<221> NAME/KEY: misc_feature
<222> LOCATION: (39)..(39)
<223> OTHER INFORMATION: The 'Xaa' at location 39 stands for Ala, Pro,
      or Ser.
<221> NAME/KEY: misc_feature
<222> LOCATION: (40)..(40)
<223> OTHER INFORMATION: The 'Xaa' at location 40 stands for Arg, Gly,
      or Trp.
<221> NAME/KEY: misc_feature
<222> LOCATION: (48)..(48)
<223> OTHER INFORMATION: The 'Xaa' at location 48 stands for Lys, Thr,
      Met, Glu, Ala,   Val, Gln, Pro, or Leu.
<221> NAME/KEY: misc_feature
<222> LOCATION: (54)..(54)
<223> OTHER INFORMATION: The 'Xaa' at location 54 stands for Val.
<221> NAME/KEY: misc_feature
<222> LOCATION: (56)..(56)
<223> OTHER INFORMATION: The 'Xaa' at location 56 stands for Lys, Glu,
      or Gln.
<221> NAME/KEY: misc_feature
<222> LOCATION: (65)..(65)
<223> OTHER INFORMATION: The 'Xaa' at location 65 stands for Glu, Asp,
      or Val.
<221> NAME/KEY: misc_feature
<222> LOCATION: (66)..(66)
<223> OTHER INFORMATION: The 'Xaa' at location 66 stands for Ile, Val,
      or Leu.
<221> NAME/KEY: misc_feature
<222> LOCATION: (76)..(76)
```

```
-continued

<223> OTHER INFORMATION: The 'Xaa' at location 76 stands for Gly.
<221> NAME/KEY: misc_feature
<222> LOCATION: (87)..(87)
<223> OTHER INFORMATION: The 'Xaa' at location 87 stands for Thr, Pro,
      or Ser.
<221> NAME/KEY: misc_feature
<222> LOCATION: (93)..(93)
<223> OTHER INFORMATION: The 'Xaa' at location 93 stands for Asp, or
      Ala.
<221> NAME/KEY: misc_feature
<222> LOCATION: (102)..(102)
<223> OTHER INFORMATION: The 'Xaa' at location 102 stands for Lys, or
      Asn.
<221> NAME/KEY: misc_feature
<222> LOCATION: (103)..(103)
<223> OTHER INFORMATION: The 'Xaa' at location 103 stands for Arg, or
      Ser.
<221> NAME/KEY: misc_feature
<222> LOCATION: (109)..(109)
<223> OTHER INFORMATION: The 'Xaa' at location 109 stands for Thr, Ala,
      or Ser.
<221> NAME/KEY: misc_feature
<222> LOCATION: (112)..(112)
<223> OTHER INFORMATION: The 'Xaa' at location 112 stands for Asp, His,
      or Tyr.
<221> NAME/KEY: misc_feature
<222> LOCATION: (114)..(114)
<223> OTHER INFORMATION: The 'Xaa' at location 114 stands for Arg, or
      Ser.
<221> NAME/KEY: misc_feature
<222> LOCATION: (117)..(117)
<223> OTHER INFORMATION: The 'Xaa' at location 117 stands for Gly.
<221> NAME/KEY: misc_feature
<222> LOCATION: (148)..(148)
<223> OTHER INFORMATION: The 'Xaa' at location 148 stands for Val.
<221> NAME/KEY: misc_feature
<222> LOCATION: (150)..(150)
<223> OTHER INFORMATION: The 'Xaa' at location 150 stands for Pro.
<221> NAME/KEY: misc_feature
<222> LOCATION: (153)..(153)
<223> OTHER INFORMATION: The 'Xaa' at location 153 stands for Ile, Val,
      or Phe.
<221> NAME/KEY: misc_feature
<222> LOCATION: (154)..(154)
<223> OTHER INFORMATION: The 'Xaa' at location 154 stands for Glu, or
      Asp.
<221> NAME/KEY: misc_feature
<222> LOCATION: (157)..(157)
<223> OTHER INFORMATION: The 'Xaa' at location 157 stands for Ser, Gly,
      or Arg.
<221> NAME/KEY: misc_feature
<222> LOCATION: (159)..(159)
<223> OTHER INFORMATION: The 'Xaa' at location 159 stands for Gly.
<221> NAME/KEY: misc_feature
<222> LOCATION: (183)..(183)
<223> OTHER INFORMATION: The 'Xaa' at location 183 stands for Thr.
<221> NAME/KEY: misc_feature
<222> LOCATION: (223)..(223)
<223> OTHER INFORMATION: The 'Xaa' at location 223 stands for Pro.
<221> NAME/KEY: misc_feature
<222> LOCATION: (225)..(225)
<223> OTHER INFORMATION: The 'Xaa' at location 225 stands for Ser.
<221> NAME/KEY: misc_feature
<222> LOCATION: (237)..(237)
<223> OTHER INFORMATION: The 'Xaa' at location 237 stands for Ser, Thr,
      Ile, Gly, Ala, Val, Cys, or Phe.
<221> NAME/KEY: misc_feature
<222> LOCATION: (239)..(239)
<223> OTHER INFORMATION: The 'Xaa' at location 239 stands for Val.
<221> NAME/KEY: misc_feature
<222> LOCATION: (241)..(241)
<223> OTHER INFORMATION: The 'Xaa' at location 241 stands for Val.
<221> NAME/KEY: misc_feature
<222> LOCATION: (242)..(242)
<223> OTHER INFORMATION: The 'Xaa' at location 242 stands for Val, Leu,
      or Phe.
<221> NAME/KEY: misc_feature
<222> LOCATION: (246)..(246)
<223> OTHER INFORMATION: The 'Xaa' at location 246 stands for Lys, Asn,
```

```
            or Thr.
<221>   NAME/KEY: misc_feature
<222>   LOCATION: (251)..(251)
<223>   OTHER INFORMATION: The 'Xaa' at location 251 stands for Tyr, Ser,
        or Phe.
<221>   NAME/KEY: misc_feature
<222>   LOCATION: (259)..(259)
<223>   OTHER INFORMATION: The 'Xaa' at location 259 stands for Leu, or
        Phe.
<221>   NAME/KEY: misc_feature
<222>   LOCATION: (305)..(305)
<223>   OTHER INFORMATION: The 'Xaa' at location 305 stands for Leu.
<221>   NAME/KEY: misc_feature
<222>   LOCATION: (319)..(319)
<223>   OTHER INFORMATION: The 'Xaa' at location 319 stands for Pro.
<221>   NAME/KEY: misc_feature
<222>   LOCATION: (346)..(346)
<223>   OTHER INFORMATION: The 'Xaa' at location 346 stands for Lys, Arg,
        Thr, Gln, Pro, a stop codon, Trp, or Ser.
<221>   NAME/KEY: misc_feature
<222>   LOCATION: (411)..(411)
<223>   OTHER INFORMATION: The 'Xaa' at location 411 stands for Lys, Thr,
        or Met.
<221>   NAME/KEY: misc_feature
<222>   LOCATION: (421)..(421)
<223>   OTHER INFORMATION: The 'Xaa' at location 421 stands for Thr, Ala,
        or Ser.
<221>   NAME/KEY: misc_feature
<222>   LOCATION: (457)..(457)
<223>   OTHER INFORMATION: The 'Xaa' at location 457 stands for Leu.
<221>   NAME/KEY: misc_feature
<222>   LOCATION: (458)..(458)
<223>   OTHER INFORMATION: The 'Xaa' at location 458 stands for Pro.
<221>   NAME/KEY: misc_feature
<222>   LOCATION: (466)..(466)
<223>   OTHER INFORMATION: The 'Xaa' at location 466 stands for Pro.
<221>   NAME/KEY: misc_feature
<222>   LOCATION: (487)..(487)
<223>   OTHER INFORMATION: The 'Xaa' at location 487 stands for Gly.
<221>   NAME/KEY: misc_feature
<222>   LOCATION: (493)..(493)
<223>   OTHER INFORMATION: The 'Xaa' at location 493 stands for Val.
<221>   NAME/KEY: misc_feature
<222>   LOCATION: (518)..(518)
<223>   OTHER INFORMATION: The 'Xaa' at location 518 stands for Thr.
<221>   NAME/KEY: misc_feature
<222>   LOCATION: (536)..(536)
<223>   OTHER INFORMATION: The 'Xaa' at location 536 stands for Val.
<221>   NAME/KEY: misc_feature
<222>   LOCATION: (556)..(556)
<223>   OTHER INFORMATION: The 'Xaa' at location 556 stands for Met, Ile,
        Val, or Leu.
<221>   NAME/KEY: misc_feature
<222>   LOCATION: (557)..(557)
<223>   OTHER INFORMATION: The 'Xaa' at location 557 stands for Ile, Val,
        or Leu.
<221>   NAME/KEY: misc_feature
<222>   LOCATION: (558)..(558)
<223>   OTHER INFORMATION: The 'Xaa' at location 558 stands for Thr, Ala,
        or Pro.
<221>   NAME/KEY: misc_feature
<222>   LOCATION: (559)..(559)
<223>   OTHER INFORMATION: The 'Xaa' at location 559 stands for Thr, Ala,
        or Ser.
<221>   NAME/KEY: misc_feature
<222>   LOCATION: (561)..(561)
<223>   OTHER INFORMATION: The 'Xaa' at location 561 stands for Ile, Leu,
        or Phe.
<221>   NAME/KEY: misc_feature
<222>   LOCATION: (562)..(562)
<223>   OTHER INFORMATION: The 'Xaa' at location 562 stands for Lys, Glu,
        or Gln.
<221>   NAME/KEY: misc_feature
<222>   LOCATION: (567)..(567)
<223>   OTHER INFORMATION: The 'Xaa' at location 567 stands for Thr, Ala,
        or Ser.
<221>   NAME/KEY: misc_feature
<222>   LOCATION: (572)..(572)
<223>   OTHER INFORMATION: The 'Xaa' at location 572 stands for Asn, or
```

Tyr.
<221> NAME/KEY: misc_feature
<222> LOCATION: (575)..(575)
<223> OTHER INFORMATION: The 'Xaa' at location 575 stands for Glu, Ala, or Val.
<221> NAME/KEY: misc_feature
<222> LOCATION: (581)..(581)
<223> OTHER INFORMATION: The 'Xaa' at location 581 stands for Thr, Ala, or Ser.
<221> NAME/KEY: misc_feature
<222> LOCATION: (583)..(583)
<223> OTHER INFORMATION: The 'Xaa' at location 583 stands for Asn, Asp, or Tyr.
<221> NAME/KEY: misc_feature
<222> LOCATION: (617)..(617)
<223> OTHER INFORMATION: The 'Xaa' at location 617 stands for Pro.
<221> NAME/KEY: misc_feature
<222> LOCATION: (618)..(618)
<223> OTHER INFORMATION: The 'Xaa' at location 618 stands for Pro, or Ser.
<221> NAME/KEY: misc_feature
<222> LOCATION: (643)..(643)
<223> OTHER INFORMATION: The 'Xaa' at location 643 stands for Glu, Asp, Gln, His, a stop codon, or Tyr.
<221> NAME/KEY: misc_feature
<222> LOCATION: (647)..(647)
<223> OTHER INFORMATION: The 'Xaa' at location 647 stands for Thr, Pro, or Ser.
<221> NAME/KEY: misc_feature
<222> LOCATION: (650)..(650)
<223> OTHER INFORMATION: The 'Xaa' at location 650 stands for Ala, Pro, or Ser.
<221> NAME/KEY: misc_feature
<222> LOCATION: (660)..(660)
<223> OTHER INFORMATION: The 'Xaa' at location 660 stands for Thr, Ala, or Ser.
<221> NAME/KEY: misc_feature
<222> LOCATION: (708)..(708)
<223> OTHER INFORMATION: The 'Xaa' at location 708 stands for Asn, Ser, Thr, Asp, Gly, Ala, Tyr, or Cys.
<221> NAME/KEY: misc_feature
<222> LOCATION: (710)..(710)
<223> OTHER INFORMATION: The 'Xaa' at location 710 stands for Ser, Arg, or Cys.

<400> SEQUENCE: 30

Met Ala Pro Ser Xaa Asp Ser Ile Ala Thr Ser Xaa Ala Asn Gly Xaa
1               5                   10                  15

Xaa Asn Xaa Xaa His Ala Ala Pro Xaa Lys Xaa Xaa Thr Gly Ala Thr
            20                  25                  30

Ser Xaa Leu Xaa Arg Pro Xaa Xaa Leu Ala Pro Pro Ala Thr Gln Xaa
        35                  40                  45

Thr Gln Leu Asp Ile Xaa Glu Xaa Ile Leu Ala Asp Pro Thr Asp Asp
    50                  55                  60

Xaa Xaa Glu Leu Asp Gly Tyr Thr Leu Thr Leu Xaa Asp Val Val Gly
65                  70                  75                  80

Ala Ala Arg Lys Gly Arg Xaa Val Arg Val Gln Thr Xaa Asp Glu Ile
                85                  90                  95

Arg Ala Lys Ile Asp Xaa Xaa Val Glu Phe Leu Arg Xaa Gln Leu Xaa
                100                 105                 110

Asn Xaa Val Tyr Xaa Val Thr Thr Gly Phe Gly Gly Ser Ala Asp Thr
        115                 120                 125

Arg Thr Glu Asp Ala Ile Ser Leu Gln Lys Ala Leu Leu Glu His Gln
    130                 135                 140

Leu Cys Gly Xaa Leu Xaa Thr Ser Xaa Xaa Ser Phe Xaa Leu Xaa Arg
145                 150                 155                 160

Gly Leu Glu Asn Ser Leu Pro Leu Glu Val Val Arg Gly Ala Met Thr
                165                 170                 175

-continued

```
Ile Arg Val Asn Ser Leu Xaa Arg Gly His Ser Ala Val Arg Leu Val
            180                 185                 190

Val Leu Glu Ala Leu Thr Asn Phe Leu Asn His Gly Ile Thr Pro Ile
            195                 200                 205

Val Pro Leu Arg Gly Thr Ile Ser Ala Ser Gly Asp Leu Ser Xaa Leu
            210                 215                 220

Xaa Tyr Ile Ala Ala Ala Ile Thr Gly His Pro Asp Xaa Lys Xaa His
225                 230                 235                 240

Xaa Xaa His Glu Gly Xaa Glu Lys Ile Met Xaa Ala Arg Glu Ala Ile
                245                 250                 255

Ala Leu Xaa Gly Leu Glu Pro Val Val Leu Gly Pro Lys Glu Gly Leu
            260                 265                 270

Gly Leu Val Asn Gly Thr Ala Val Ser Ala Ser Met Ala Thr Leu Ala
            275                 280                 285

Leu His Asp Ala His Met Leu Ser Leu Leu Ser Gln Ala Leu Thr Ala
            290                 295                 300

Xaa Thr Val Glu Ala Met Val Gly His Ala Gly Ser Phe His Xaa Phe
305                 310                 315                 320

Leu His Asp Val Thr Arg Pro His Pro Thr Gln Ile Glu Val Ala Arg
                325                 330                 335

Asn Ile Arg Thr Leu Leu Glu Gly Ser Xaa Phe Ala Val His His Glu
            340                 345                 350

Glu Glu Val Lys Val Lys Asp Asp Glu Gly Ile Leu Arg Gln Asp Arg
            355                 360                 365

Tyr Pro Leu Arg Thr Ser Pro Gln Trp Leu Gly Pro Leu Val Ser Asp
370                 375                 380

Met Ile His Ala His Ala Val Leu Ser Leu Glu Ala Glu Ser Thr Thr
385                 390                 395                 400

Asp Asn Pro Leu Ile Asp Val Glu Asn Lys Xaa Thr His His Gly Gly
            405                 410                 415

Asn Phe Gln Ala Xaa Ala Val Ala Asn Thr Met Glu Lys Thr Arg Leu
            420                 425                 430

Ala Leu Ala Leu Ile Gly Lys Leu Asn Phe Thr Gln Leu Thr Glu Met
            435                 440                 445

Leu Asn Ala Gly Met Asn Arg Gly Xaa Xaa Ser Cys Leu Ala Ala Glu
            450                 455                 460

Asp Xaa Ser Leu Ser Tyr His Cys Lys Gly Leu Asp Ile Ala Ala Ala
465                 470                 475                 480

Ala Tyr Thr Ser Glu Leu Xaa His Leu Ala Asn Pro Xaa Thr Thr His
                485                 490                 495

Val Gln Pro Arg Glu Met Gly Asn Gln Ala Val Asn Ser Leu Ala Leu
            500                 505                 510

Ile Ser Ala Arg Arg Xaa Ala Glu Ala Asn Asp Val Leu Ser Leu Leu
            515                 520                 525

Leu Ala Thr His Leu Tyr Cys Xaa Leu Gln Ala Val Asp Leu Arg Ala
            530                 535                 540

Met Glu Phe Glu Phe Lys Lys Gln Phe Asp Pro Xaa Xaa Xaa Xaa Leu
545                 550                 555                 560

Xaa Xaa Gln His Phe Gly Xaa Ala Leu Asp Gly Xaa Glu Leu Xaa Asp
                565                 570                 575

Lys Val Asn Lys Xaa Leu Xaa Lys Arg Leu Glu Gln Thr Asn Ser Tyr
            580                 585                 590
```

-continued

```
Asp Leu Glu Pro Arg Trp His Asp Ala Phe Ser Phe Ala Thr Gly Thr
    595                 600                 605
Val Val Glu Leu Leu Ser Ser Ser Xaa Xaa Ala Lys Val Ser Leu Ala
    610                 615                 620
Ala Val Asn Ala Trp Lys Val Ala Ser Ala Glu Lys Ala Ile Ser Leu
625             630                 635                 640
Thr Arg Xaa Val Arg Asp Xaa Phe Trp Xaa Ala Pro Ser Ser Ser Ser
            645                 650                 655
Pro Ala Leu Xaa Tyr Leu Ser Pro Arg Thr Arg Val Leu Tyr Ser Phe
            660                 665                 670
Val Arg Glu Glu Leu Gly Val Lys Ala Arg Arg Gly Asp Val Phe Leu
    675                 680                 685
Gly Lys Gln Glu Val Thr Ile Gly Thr Asn Val Ser Arg Ile Tyr Glu
    690                 695                 700
Ala Ile Lys Xaa Gly Xaa Ile Asn His Val Leu Val Lys Met Leu Ala
705             710                 715                 720
```

PHENYLALAININE AMMONIA LYASE POLYPEPTIDE AND POLYNUCLEOTIDE SEQUENCES AND METHODS OF OBTAINING AND USING SAME

CROSS REFERENCE TO RELATED APPLICATIONS

This application is a continuation-in-part of U.S. patent application Ser. No. 09/624,693, filed Jul. 24, 2000, now U.S. Pat. No. 6,355,468, and is a continuation-in-part application of PCT International Application PCT/US01/23270, having an international filing date of July 24, 2001.

TECHNICAL FIELD OF THE INVENTION

The present invention relates inter alia to a *Rhodotorula* phenylalanine lyase polypeptide, to polynucleotides encoding the polypeptide, and to methods of obtaining and using these products.

BACKGROUND OF THE INVENTION

Phenylalanine ammonia lyase (PAL; EC 4.3.1.5.) is an enzyme that is found in several plants, yeast, and *Streptomyces*. PAL catalyzes the nonoxidative deamination of L-phenylalanine to trans-cinnamic acid. The enzyme has a potential role in the treatment and diagnosis of phenylketonuria (Ambrus et al., *Science*, 201, 837–839 (1978)) and cancer, and is commercially useful for the manufacture of L-phenylalanine from ammonia and t-cinnamate.

Many references describe PAL-producing yeast strains that are useful in fermentation cultures for producing phenylalanine. *Rhodotorula glutinis* can be employed to obtain PAL activity in the presence of inducer, but the activity reaches a maximum after about six hours of induction and then diminishes thereafter. PAL similarly is rapidly degraded in the absence of the inducer during fermentation and has a half-life of approximately 2–5 hours during fermentations of most *Rhodotorula rubra* strains.

U.S. Pat. No. 4,598,047 describes mutant strains of *Rhodotorula rubra* (GX 5902, GX 5903, GX 5904 specifically) that are useful for PAL production. *Rhodotorula graminis* wild-type strain KGX 39 (also known as GX 5007) is a soil isolate that similarly has PAL activity (Durham et al., *J. Bact.*, 160, 771–777 (1984)). KGX 39 has several advantages over other production strains of *Rhodotorula rubra*. It grows 15–20% faster and requires less yeast extract, has no L-methionine requirement during induction, and its PAL half-life during fermentation is about 8 to 9 hours. *R. graminis* KGX 39, however, is undesirable as a production strain due to low PAL titers obtained during fermentation.

An over-producing PAL mutant also has been obtained by mutagenesis of strain KGX 39, as described in U.S. Pat. No. 4,757,015. This mutagenized strain (deposited as ATCC 20804) has high PAL specific activity and titer, high PAL specific productivity, high stability, and lower fermentation times to maximum PAL concentration than any of the previously-available PAL-producing yeast strains.

The use of yeast-derived PAL to produce a variety of optically-active unnatural amino acids having phenylalanine-like structures as chiral synthons for synthesis recently has been described (see, U.S. Pat. No. 5,981,239, incorporated by reference in its entirety herein). According to this reference, the stereospecific introduction of ammonia is accomplished with use of microorganism cells (i.e., cells of the yeast strain *Rhodotorula graminis* ATCC 20804) as the biocatalyst for the stereospecific conversion. Phenylalanine ammonia lyase from *R. graminis* ATCC 20804 was found to demonstrate broad substrate specificity for introduction of a molecule of ammonia stereoselectively onto the double bond of a 3-substituted acrylic acid. This newly discovered activity of *R. graminis* PAL should prove useful commercially.

In particular, phenylalanine and its derivatives also have been used as essential building blocks in the construction of various types of biologically active molecules. For instance, protease inhibitors employed in the treatment of human immunodeficiency virus and human cytomegalovirus infections contain a phenylalanine-like architecture as their pharmacophores. Presently there is a need for a general process of preparing a variety of optically active unnatural amino acids (i.e., amino acids that are not found in nature) having phenylalanine-like structures as chiral synthons for synthesis of these drug candidates. Based on the broad substrate specificity of *R. graminis*, it would be useful to obtain the polypeptide and nucleic acid sequences of its PAL, e.g., amongst other things, for optimization of its enzymatic activities in these synthesis reactions.

Accordingly, while polynucleotides encoding phenylalanine ammonia lyase have been isolated from the yeasts *Rhodosporidium toruloides* (PCT WO 88/02824) and *Rhodotorula rubra* (Filpula et al., *Nucleic Acids Research*, 16, 11381 (1988), it would be useful to obtain the polynucleotide sequence of still other species. There is a need for strains that can be employed for the production of phenylalanine, phenylalanine analogs, and other optically active unnatural amino acids having phenylalanine-like structures. The present invention thus is directed, amongst other things, to methods, vectors, sequences, and compositions to meet that need. These and other objects and advantages of the present invention, as well as additional inventive features, will be apparent from the description of the invention provided herein. The description and examples are provided to enhance the understanding of the invention, but are not intended to in any way limit the scope of the invention.

BRIEF SUMMARY OF THE INVENTION

The present invention provides a *Rhodotorula* phenylalanine lyase polypeptide, polynucleotides encoding the polypeptide, and methods of obtaining and using these products.

BRIEF DESCRIPTION OF THE FIGURES

FIGS. 1A–1B are the alignment of PAL polypeptide sequences of *R. graminis* strain ATCC 20804 (SEQ ID NO:13), *R. toruloides* (SEQ ID NO:19), and *R. mucilaginosa* (SEQ ID NO:17), and the consensus of these sequences (SEQ ID NO:21), as described in Example 3. Gaps in the sequence are denoted with a hyphen, "X" (i.e., "Xaa" in the three-letter code) means there is no consensus between the sequences at that amino acid residue.

FIGS. 2A–2F are the alignment of PAL polynucleotide sequences (cDNA sequences) of *R. graminis* (SEQ ID NO:12, residues 37–2419), *R. toruloides* (SEQ ID NO:18), and *R. rubra/mucilaginosa*) (SEQ ID NO: 16, residues 646–2787), and the consensus of these sequences (SEQ ID NO:20). Gaps in this figure are denoted with a hyphen, "N" means there is no consensus between the sequences at that nucleic acid residue.

FIG. 3 is the PAL genomic DNA sequence of ATCC 20804 (SEQ ID NO:28) with introns underlined.

FIG. 4 is the PAL genomic DNA sequence of KGX 39 (SEQ ID NO:28) with introns underlined.

DESCRIPTION OF THE PREFERRED EMBODIMENTS

The present invention provides, amongst other things, novel purified and isolated yeast PAL sequences, particularly those of the yeast *Rhodotorula,* and especially those of the yeast *Rhodotorula gramin* is.

Of course, the sequences of the invention optionally can be present either in their polypeptide/protein form (e.g., in the "polypeptide sequence"), or, in the form of their encoding nucleic acids (e.g., either as purified nucleic acid species, and/or in certain of the vectors). As used herein, lower case "pal" refers to a nucleic acid sequence whereas upper case "PAL" refers to an amino acid sequence.

PAL Polypeptides

The present invention provides, inter alia, novel purified and isolated yeast PAL polypeptides.

The conventional abbreviations for amino acids comprising proteins and peptides are used herein as generally accepted in the peptide art and as recommended by the IUPAC-IUB Commission on Biochemical Nomenclature (See, *European J. Biochem.,* 138, 9–37 (1984)). Similarly, protein and peptide sequences are written according to the standard convention wherein the N-terminal amino acid is on the left and the C-terminal amino acid is on the right (with corresponding nucleic acid sequences being written in a 5' to 3' direction). The term "peptide" as used herein refers to any length molecular chain of amino acids linked by peptide bonds. As used herein, "protein" refers to the full length (i.e., complete) protein. The term "peptide" encompasses the term "polypeptide", which, as used herein, refers more specifically to a linear polymer of more than 3 amino acids, and which can either be a complete protein (i.e., having both amino and carboxy terminuses), or an incomplete protein (i.e., lacking either an amino or carboxy terminus). The polypeptides of the invention desirably can be modified such as is known in the art.

The proteins of the present invention preferably comprise an amino end and a carboxyl end. However, polypeptides having a modified amino- and/or carboxy-terminus are desirable since proteins and peptides with modified termini are expected to have longer in vivo half-lives since endopeptidases have reduced activity with respect to proteins and peptides with modified termini. The polypeptides can comprise D- or L-peptides, or a mixture of the D- and L-amino acid forms. Polypeptides (particularly proteins) comprising L-amino acids are preferred. However, the D-form of the amino acids are also desirable since proteins and polypeptides comprising D-amino acids are expected to have a greater retention of their biological activity in vivo given that the D-amino acids are not recognized by naturally occurring proteases.

The invention thus also provides purified and isolated yeast PAL polypeptides. An exemplary PAL polypeptide has an amino acid sequence defined in SEQ ID NO:13. PAL polypeptides of the invention preferably are isolated from natural cell sources, or chemically synthesized, or desirably are produced by recombinant procedures involving host cells of the invention. PAL polypeptides of the invention preferably are full-length polypeptides, or variant polypeptides such as fragments, truncates, deletion mutants, and other variants thereof that retain specific PAL biological activity. As used herein, "biologically active" refers to a PAL polypeptide having at least one of the structural, regulatory or biochemical functions of the naturally occurring PAL protein. Specifically, a PAL protein of the present invention has the ability to manufacture phenylalanine, phenylalanine analogs, and other optically active unnatural amino acids having phenylalanine-like structures, when provided with the appropriate substrates.

The polypeptide and polypeptide fragments of the present invention preferably are prepared by methods known in the art. Such methods include, but are not limited to, isolating these products directly from cells, isolating or synthesizing DNA encoding these products and using the DNA to produce recombinant products, synthesizing the products chemically from individual amino acids, and production of fragments by chemical cleavage of existing products.

The PAL polypeptides can be isolated from a biological sample, such as a solubilized cell fraction, by any standard method known in the art. Some suitable methods include precipitation and liquid chromatographic protocols such as ion exchange, hydrophobic interaction, and gel filtration, as well as immunoaffixity purification. See, for example, Deutscher (Ed.), *Methods Enzymol (Guide to Protein Chemistry, Section VII),* 182:309 (1990) and Scopes, *Protein Purification,* Springer-Verlag, New York (1987). Also, purified material desirably is obtained by separating the protein on preparative SDS-PAGE gels, slicing out the band of interest, and electroeluting the protein from the polyacrylamide matrix by methods known in the art. The detergent SDS is removed from the protein by known methods, such as by dialysis or the use of a suitable column, such as the Extracti-Gel column from Pierce.

The PAL polypeptides of the invention also can be chemically synthesized, wholly or in part, by methods known in the art. In particular, chemical synthesis may prove useful for production of only portions of a PAL polypeptide (i.e., PAL fragments), particularly those fragments less than about 200 amino acids in length. Suitable methods for synthesizing the protein are described by Stuart and Young, *Solid Phase Peptide Synthesis,* 2d ed., Pierce Chemical Co. (1984), and Bodanszky, *Principles of Peptide Synthesis,* (Springer-Verlag, Heidelberg: 1984)). For example, peptides can be synthesized by solid phase techniques, cleaved from the resin, and purified by preparative high performance liquid chromatography (HPLC). See, e.g., Roberge et al., *Science,* 269:202–204 (1995). In particular, the peptides can be synthesized using the procedure of solid-phase synthesis (see, e.g., Merrifield, *J. Am. Chem. Soc.,* 85, 2149–54 (1963); Barany et al., *Int. J Peptide Protein Res.,* 30, 705-739 (1987); and U.S. Pat. No. 5,424,398), and modifications thereof. If desired, this can be done using an automated peptide synthesizer (e.g., Perkin Elmer ABI 431A Peptide Synthesizer, or other appropriate synthesizer) according to the instructions of the manufacturer. Removal of the t-butyloxycarbonyl (t-BOC) or 9-fluorenylmethyloxycarbonyl (Fmoc) amino acid blocking groups and separation of the peptide from the resin can be accomplished by, for example, acid treatment at reduced temperature. The peptide-containing mixture can then be extracted, for instance, with dimethyl ether, to remove non-peptide organic compounds, and the synthesized peptides can be extracted from the resin powder (e.g., with about 25% w/v acetic acid). Following the synthesis of the peptide, further purification (e.g., using high performance liquid chromatography (HPLC)) optionally can be done in order to eliminate any incomplete peptides or free amino acids. Amino acid analysis and/or sequencing (e.g., the Edman degradation procedure) can be performed on the synthesized polypeptides to validate the composition of the synthetic peptides.

As described in greater detail below (section on polypeptide expression systems), recombinant PAL protein also may be produced in and isolated from a host cell transformed with an expression vector containing a pal nucleotide sequence and grown in culture. A PAL-encoding polynucleotide of the invention can be introduced by any means into either a prokaryotic or eukaryotic cell in a manner that permits directed expression of a PAL polypeptide. In such methods, the host cells are grown in a suitable culture medium and the desired polypeptide products are isolated from the cells or from the medium in which the cells are grown. Isolation of the polypeptides can be accomplished by any appropriate means such as is known in the art.

The invention includes polypeptides comprising amino acid sequences that are substantially homologous to the sequences of PAL polypeptides described herein. For example, the invention includes polypeptides whose corresponding amino acid sequences have at least 80%, preferably at least 90%, more preferably at least 91%, 92%, 93%, 94%, or 95% identity, and still more preferably at least 98% identity (or, also desirably, similarity) with the polypeptide sequence defined in SEQ ID NO:13.

Percent sequence "identity" with respect to a preferred polypeptide of the invention can be defined as the percentage of amino acid residues in a candidate sequence that are identical to amino acid residues in the reference PAL sequence after aligning the sequences and introducing gaps, if necessary, to achieve maximum percent sequence identity, and not considering any conservative substitutions as part of the sequence identity. Percent sequence "similarity" with respect to a preferred polypeptide of the invention can be defined as the percentage of amino acid residues in a candidate sequence that are identical to amino acid residues in the reference PAL sequence after aligning the sequences and introducing gaps, if necessary, to achieve maximum percent sequence identity, and also considering any conservative substitutions as part of the sequence identity.

Sequence alignment of polypeptides for purposes of sequence comparison can be done using a variety of multiple alignment servers, most of which are presently available on the Internet, e.g., Clustal W, MAP, PIMA, Block Maker, MSA, MEME, and Match-Box. Preferably Clustal W (Higgins et al., *Gene*, 73, 237–244 (1988); Higgins et al., *Meth. Enzymol.*, 266, 383–402 (1996)) is employed for sequence alignment of polypeptides (and also, polynucleotides). Similarly, the program BLASTP compares an amino acid query sequence against a protein database, and TBLASTN compares a protein query sequence against a nucleotide sequence database dynamically translated in all six reading frames (both strands), and can be employed in the invention.

Determinations of whether two amino acid sequences are substantially homologous (i.e., similar or identical) also can be based on FASTA searches in accordance with Pearson et al., *Proc. Natl. Acad. Sci. USA*, 85:2444–2448 (1988). Alternatively (but less preferably), percent homology is calculated as the percentage of amino acid residues in the smaller of the two sequences that align with identical amino acid residues in the sequence being compared, when four gaps in a length of 100 amino acids may be introduced to maximize alignment. See Dayhoff, in Atlas of Protein Sequence and Structure, Vol. 5, p. 124, National Biochemical Research Foundation, Washington, D.C. (1972).

In particular, preferred methods to determine sequence similarities are designed to give the largest match between the compared sequences. Methods to determine identity and similarity are codified in publicly available computer programs (e.g., such as those previously described). Preferred computer program methods to determine identity and similarity between two sequences include, but are not limited to, the GCG program package, including GAP (Devereux et al., *Nucleic Acids Research* 12(l):387 (1984); Genetics Computer Group, University of Wisconsin, Madison, Wis.), BLASTP, BLASTN, and FASTA (Altschul et al., *J. Molec. Biol.* 215:403–410 (1990)). The BLASTX program is publicly available from the National Center for Biotechnology Information (NCBI) and other sources (Altschul et al., *BLAST Manual,* NCB NLM NIH Bethesda, Md. 20894; Altschul et al., *J. Mol. Biol.,* 215:403–410 (1990)). The well-known Smith-Waterman algorithm also may be used to determine relative identity.

By way of example, using the computer algorithm GAP, two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 of the gap opening penalty), as well as a comparison matrix such as PAM 250 or BLOSUM 62 are used in conjunction with the algorithm. A standard comparison matrix (see Dayhoff et al., in: *Atlas of Protein Sequence and Structure,* vol. 5, supp.3 (1978) for the PAM250 comparison matrix; see Henikoff et al., *Proc. Natl. Acad. Sci USA,* 89:10915–10919 (1992) for the BLOSUM 62 comparison matrix) is also used by the algorithm.

Preferred parameters for polypeptide sequence comparison include the following:

Algorithm: Needleman and Wunsch, *J. Mol. Biol. (1970)* 48:443–453,

Comparison matrix: BLOSUM 62 from Henikoff and Henikoff, *Proc. Natl. Acad. Sci. USA* 89:10915–10919 (1992).

Gap Penalty: 12

Gap Length Penalty: 4

Threshold of Similarity: 0

The aforementioned parameters are the default parameters for polypeptide comparisons (along with no penalty for end gaps) using the GAP algorithm.

Preferred parameters for nucleic acid sequence comparison include the following:

Algorithm: Needleman and Wunsch, *J. Mol Biol.* 48:443–453 (1970)

Comparison matrix: matches=+10, mismatch=0

Gap Penalty: 50

Gap Length Penalty: 3

The aforementioned parameters are the default parameters for nucleic acid molecule comparisons.

Other exemplary algorithms, gap opening penalties, gap extension penalties, comparison matrices, thresholds of similarity, and the like may be used by those of skill in the art, including use of those parameters set forth in the Program Manual, Wisconsin Package, Version 9, September, 1997. The particular choices to be made will depend on the specific comparison to be made, such as DNA to DNA, protein to protein, and protein to DNA; additionally, the choice depends on whether the comparison is between pairs of sequences (in which case GAP or BestFit are generally preferred) or between one sequence and a large database of sequences (in which case FASTA or BLASTA are preferred).

Certain alignment schemes for aligning two amino acid sequences may result in matching of only a short region of the two sequences, and this small aligned region may have very high sequence identity even though there is no significant relationship between the two full-length sequences. Accordingly, in a preferred embodiment, the selected alignment method will result in an alignment that spans at least 66 contiguous amino acids of the claimed full-length polypeptide.

A polypeptide also may be considered homologous to a PAL polypeptide of the invention if polynucleotides encoding the two polypeptides hybridize with one another. A higher degree of homology is shown if the hybridization occurs under hybridization conditions of greater stringency. Control of hybridization conditions and the relationships between hybridization conditions and degree of homology are understood by those skilled in the art (see, e.g., Sambrook et al. (Eds.), *Molecular Cloning: A Laboratory Manual,* Cold Spring Harbor Laboratory Press: Cold Spring Harbor, N.Y., pp. 9.47 to 9.51 (1989)), and are as previously described, and as described in the examples that follow. Thus, a homologous polypeptide may be a polypeptide that is encoded by a polynucleotide that hybridizes with a polynucleotide encoding a polypeptide of the invention under hybridization conditions having a specified degree of stringency. Relationships based on hybridization as just described do not result in a particular "identity" or "similarity" value being assigned to compared polypeptides, but such a value generally can be inferred.

It also may be desirable that such structurally homologous polypeptides will exhibit functional homology, insofar as the homologous polypeptide has substantially the same function as the polypeptide of the invention. Structurally homologous polypeptides may be considered functionally homologous if they exhibit similar biological activity. Generally, if 24 out of 80 appropriately aligned residues (i.e., 30%; more for shorter matches, Sander et al., *Proteins,* 9, 56–68 (1991)) are identical between two naturally evolved proteins, the two polypeptides/proteins will have similar three-dimensional structures and similar functions (Chothia et al., *EMBO J.,* 5, 823–826 (1986); Feng et al., *J. Mol. Evol.,* 21, 112–125 (1985).

On the other hand, it is also known that two polypeptides or two polynucleotides can be considered to be substantially homologous in structure, and yet differ substantially in function. For example, single nucleotide polymorphisms (SNPs) among alleles may be expressed as polypeptides having substantial differences in function along one or more measurable parameters such as antibody- or ligand-binding affinity or enzymatic substrate specificity, and the like. Other structural differences, such as substitutions, deletions, splicing variants, and the like, may affect the function of otherwise structurally identical or homologous polypeptides.

The PAL polypeptides of the invention include functional derivatives of the PAL polypeptide defined in SEQ ID NO:13. Such functional derivatives include polypeptide products that possess a structural feature or a biological activity that is substantially similar to a structural feature or a biological activity of the PAL protein. Accordingly, functional derivatives include variants, fragments, and chemical derivatives of the parent PAL protein.

As used herein "variant" refers to a molecule substantially similar in structure and function to either the entire PAL molecule, or to a fragment thereof. A molecule is said to be "substantially similar" to another molecule if both molecules have substantially similar structures and/or if both molecules possess a similar biological activity. Thus, provided that two molecules possess a similar activity, they are considered variants, as that term is used herein, even if one of the molecules possesses a structure not found in the other molecule, or if the sequence of amino acid residues is not identical. Among the variant polypeptides provided under the invention are variants that comprise one or more changes in the amino acid sequence of the PAL polypeptide. Such sequence-based changes include deletions, substitutions, or insertions in the PAL polypeptide sequence, as well as combinations thereof.

Deletion variants of the PAL polypeptides are polypeptides in which at least one amino acid residue of the sequence is removed. Deletions can be effected at one or both termini of the protein, or with removal of one or more residues within (i.e., internal to) the PAL amino acid sequence. Deletion variants include, for example, all incomplete fragments of the PAL polypeptides of the invention, but particularly, PAL polypeptides comprising deletion of one, two, three, four, five, or six residues at the amino and/or carboxyl terminus. As used herein "fragment" refers to any polypeptide subset of the PAL protein. Such fragments include, for example, fragments comprising particular amino acids of the amino acid sequence defined by SEQ ID NO:13, as well as N-terminally extended fragments of that sequence and C-terminal truncates thereof. Fragments of PAL that exhibit a biological activity characteristic of PAL (e.g., any biological activity characteristics of PAL) are desirable. Identification of such fragments is well known in the art, and is further described herein.

Substitution variants are provided, including polypeptides in which at least one amino acid residue of a PAL polypeptide is removed and replaced by an alternative residue. In one aspect, the substitutions preferably are conservative in nature, however, the invention also embraces substitutions that are non-conservative (e.g., as in cases where an altered biological activity is desired). A conservative substitution is recognized in the art as a substitution of one amino acid for another amino acid that has similar property. Any substitution can be made, with conservative substitutions (as further described herein) being preferred. Directed amino acid substitutions may be made based on well defined physicochemical parameters of the canonical and other amino acids (e.g., the size, shape, polarity, charge, hydrogen-bonding capacity, solubility, chemical reactivity, hydrophobicity, hydrophilicity, or the amphipathic character of the residues) as well as their contribution to secondary and tertiary protein structure. Substitution variants can include polypeptides comprising one or more conservative amino acid substitutions, i.e., a substitution of one amino acid by another having similar physicochemical character, as desired. To illustrate, the canonical amino acids can be grouped according to the categories below, and conservative substitutions for this purpose can be defined according to these groupings:

| | |
|---|---|
| Aliphatic Side Chains | Gly, Ala; Val, Leu, Ile |
| Aromatic Side Chains | Phe, Tyr, Trp |
| Aliphatic Hydroxyl Side Chains | Ser, Thr |
| Basic Side Chains | Lys, Arg, His |
| Acidic Side Chains | Asp, Glu |
| Amide Side Chains | Asn, Gln |

-continued

| | |
|---|---|
| Sulfur-Containing Side Chains | Cys, Met |
| Secondary Amino Group | Pro |

Substitutions preferably are made in accordance with Table 1 (below) when it is desired to control the characteristics of the PAL molecule. The conservative substitutions generally include those which are categorized as part of the Clustal W program as showing "strong similarity" or "weak similarity", as set out in Table 1.

TABLE 1

| | Exemplary Conservative Substitutions | |
|---|---|---|
| Original Residue | Strong Similarity | Weak Similarity |
| Ala | Gly; Ser | Cys; Thr; Val |
| Arg | Lys | Asp; Glu; His; Asn; Gln |
| Asn | Gln | Asp; Glu; Gly; His; Lys; Arg; Ser; Thr |
| Asp | Glu | Gly; His; Lys; Asn; Gln; Arg; Ser |
| Cys | | Ala; Ser |
| Gln | Asn | Asp; Glu; His; Lys; Arg; Ser |
| Glu | Asp | His; Lys; Asn; Gln; Arg; Ser |
| Gly | Ala | Asp; Asn; Ser |
| His | Tyr | Asp; Glu; Phe; Lys; Asn; Gln; Arg |
| Ile | Leu; Val; Met | Phe |
| Leu | Ile; Val; Met | Phe |
| Lys | Arg | Asp; Glu; His; Asn; Gln; Ser; Thr |
| Met | Leu; Ile; Val | Phe |
| Phe | Tyr; Trp | His; Ile; Leu; Met |
| Pro | | Ser; Thr |
| Ser | Thr; Ala | Cys; Asp; Glu; Gly; Lys; Asn; Pro; Gln |
| Thr | Ser | Ala; Lys; Asn; Pro; Val |
| Trp | Tyr; Phe | |
| Tyr | Trp; Phe; His | |
| Val | Ile; Leu; Met | Ala; Thr |

Substantial changes in structure and/or function of a PAL polypeptide are made by selecting conservative substitutions that show only weak similarity (as opposed to strong similarity), or are more progressive than those in Table 1, i.e., selecting residues that differ more significantly in their effect on maintaining: (a) the secondary structure of the polypeptide backbone in the area of the substitution, (b) the charge or hydrophobicity of the molecule at the target site, and/or (c) the bulk of the side chain. The substitutions that, in general, are more progressive are those in which: (a) glycine and/or proline is substituted by another amino acid, or is deleted or inserted; (b) a hydrophilic residue is substituted for a hydrophobic residue; (c) a cysteine residue is substituted for (or by) any other residue; (d) a residue having an electropositive side chain is substituted for (or by) a residue having an electronegative charge; and/or (e) a residue having a bulky side chain is substituted for (or by) one not having such a side chain.

Substitution variants, however, also can include noncanonical or non-naturally occurring amino acid residues substituted for amino acid residues in the principal sequence (e.g., as set forth in 37 C.F.R. §1.822). Substitution variants include those polypeptides in which amino acid substitutions have been introduced by modification of polynucleotides encoding a PAL polypeptide.

Insertion variants also desirably are provided, in which at least one amino acid residue is present in addition to a PAL amino acid sequence (e.g., including a PAL amino acid sequence having deletions and/or substitutions). Insertions may be located at either or both termini of the polypeptide, or may be positioned within (i.e., internal to) the PAL amino acid sequence. Insertion variants also include fusion proteins in which the amino or carboxy terminus of the PAL polypeptide is fused to another polypeptide. Examples of such fusion proteins include but are not limited to immunogenic polypeptides, proteins with a long circulating half-life (e.g., immunoglobulin constant regions), marker proteins (e.g., green fluorescent protein) and proteins or polypeptides that facilitate purification of the desired PAL polypeptide (e.g., FLAG® tags, polyhistidine sequences, and the like). Another example of a terminal insertion is a fusion of a signal sequence, whether heterologous or homologous to the host cell, to the N-terminus of the molecule to facilitate the secretion of the derivative from recombinant hosts. Intrasequence insertions (i.e., insertions within a PAL molecule sequence) preferably range from about 1 to about 50 residues, more preferably from about 1 to about 10 residues, and most preferably from about 1 to about 5 residues.

Polypeptide variants of the invention also include mature PAL products, e.g., PAL products wherein any leader or signal sequences are removed, as well as products having additional amino terminal residues (e.g., one or more additional methionine residue at position −1 or −n). Other such variants are particularly useful for recombinant protein production in prokaryotic or eukaryotic host cells.

The invention also encompasses PAL variants having additional amino acid residues resulting from use of specific expression systems. For example, use of commercially available vectors that express a desired polypeptide as a glutathione-S-transferase (GST) fusion product yields the desired polypeptide having an additional glycine residue at position −1 ($Gly^{-1}$-PAL) upon cleavage of the GST component from the desired polypeptide. Variants that result from expression in other vector systems are also contemplated, as are fusion proteins wherein the amino and/or carboxy termini of a PAL polypeptide is fused to another polypeptide, such as a constant region of an immunoglobulin chain or fragment thereof, or a targeting moiety such as an antibody or antibody fragment.

If desired, the polypeptides of the invention can be modified, for instance, by glycosylation, amidation, carboxylation, or phosphorylation, or by the creation of acid-addition salts, amides, esters, in particular C-terminal esters, and N-acyl derivatives of the polypeptides of the invention. The polypeptides also can be modified to create peptide derivatives by forming covalent or noncovalent complexes with other moieties. Covalently-bound complexes can be prepared by linking the chemical moieties to functional groups on the side chains of amino acids comprising the polypeptides, or at the N- and/or C-terminus. Further modifications will be apparent to those of ordinary skill in the art, and are encompassed by the invention.

In particular, the invention provides PAL polypeptide products that are chemical derivatives of the PAL polypeptide defined in SEQ ID NO:13. As used herein, the term "chemical derivative" refers to molecules that contain additional chemical moieties that are not normally a part of the naturally-occurring molecule. Such moieties desirably can impart desirable properties to the derivative molecule, such as increased solubility, absorption, biological half-life, and the like. Thus, chemical derivatives of PAL polypeptides include polypeptides bearing modifications other than (and/or in addition to) insertion, deletion or substitution of amino acid residues. Preferably, the modifications are covalent in nature, and include, for example, chemical bonding with polymers, lipids, non-naturally occurring amino acids, and other organic and inorganic moieties. In particular, derivatives of the invention preferably can be prepared to increase the ability of a PAL polypeptide to be employed for the production of phenylalanine, phenylalanine analogs, and optically active unnatural amino acids having phenylalanine-like structures.

For example, methods are known in the art for modifying a polypeptide to include one or more water-soluble polymer attachments such as polyethylene glycol, polyoxyethylene glycol, or polypropylene glycol. Particularly preferred are PAL products that have been covalently-modified with polyethylene glycol (PEG) subunits. Water-soluble polymers can be bonded at specific positions, for example at the amino terminus of the PAL products, or randomly attached to one or more side chains of the polypeptide. Additional derivatives include PAL species immobilized on a solid support, pin microparticle, or chromatographic resin, as well as PAL species modified to include one or more detectable labels, tags, chelating agents, and the like.

Derivatization with bifunctional agents can be used to cross-link PAL to a water-insoluble support matrix. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization. Immobilization of PAL may be of particular utility in its purification and/or assay.

Expression of pal variants can be expected to have utility in investigating a biological activity characteristic of a wild-type PAL polypeptide. pal variants can be designed to retain all biological or immunological properties characteristic for PAL, or to specifically disable one or more particular biological or immunological properties of PAL. For example, fragments and truncates may be designed to delete a domain associated with a particular property, or substitutions and deletions may be designed to inactivate a property associated with a particular domain. Forced expression (overexpression) of such variants ("dominant negative" mutants) can be employed to study the function of the protein in vivo in its natural host by observing the phenotype associated with the mutant.

Functional derivatives of PAL having up to about 200 residues may be conveniently prepared by in vitro synthesis. If desired, such fragments may be modified using methods known in the art by reacting targeted amino acid residues of the purified or crude protein with an organic derivatizing agent that is capable of reacting with selected side chains or terminal residues. The resulting covalent derivatives may be used to identify residues important for biological activity. Other methods such as are known in the art similarly can be employed.

Functional derivatives of PAL having altered amino acid sequences can also be prepared by mutating the DNA encoding PAL. Any combination of amino acid deletion, insertion, and substitution may be employed to generate the final construct, provided that the final construct possesses the desired activity. Obviously, the mutations that will be made in the DNA encoding the functional derivative must not place the sequence out of reading frame and preferably will not create complementary regions that could produce secondary mRNA structure (see, e.g., EP Patent Publication No. 75,444).

While the site for introducing a variation in the amino acid sequence is predetermined, the mutation per se need not be predetermined. For example, to optimize the performance of a mutation at a given site, random mutagenesis, such as linker scanning mutagenesis, can be conducted at a target codon or target region to create a large number of derivatives which could then be expressed and screened for the optimal combination of desired activity. Alternately, site-directed mutagenesis or other well-known techniques may be employed to make mutations at predetermined sites in a DNA known sequence.

The technique of site-directed mutagenesis is well known in the art, as exemplified by publications such as Sambrook et al., supra, and McPherson (Ed.), *Directed Mutagenesis: A Practical Approach,* IRL Press, Oxford (1991). Site-directed mutagenesis allows the production of pal functional derivatives through use of specific oligonucleotide sequences that encode the DNA sequence of the desired mutation. Site-directed mutagenesis methods and materials are commercially available, e.g., the QuikChange™ kit available from Stratagene (La Jolla Calif.). One can selectively generate precise amino acid deletions, insertions, or substitutions using this method. Amino acid sequence deletions according to the invention preferably range from about 1 to about 50 residues, more preferably from about 1 to about 30 residues, even more desirably from about 1 to about 10 residues, and typically are contiguous.

Mutations designed to alter the activity of PAL may be guided by the introduction of the amino acid residues that are present at homologous positions in other phenylalanine ammonia lyase proteins (particularly PAL proteins of evolutionarily similar genus/species). It is difficult to predict a priori the exact effect any particular modification, e.g., substitution, deletion, insertion, etc., will have on the biological activity of PAL. However, one skilled in the art will appreciate that the effect will be evaluated by routine screening assays. For example, a derivative typically is made by linker scanning site-directed mutagenesis of the DNA encoding the native PAL molecule. The derivative is then expressed in a recombinant host, and, optionally, purified from the cell culture, for example, by immunoaffinity chromatography. The activity of the cell lysate or the purified derivative is then screened in a suitable screening assay for the desired characteristic. For example, a change in the immunological character of the functional derivative, such as affinity for a given antibody, is measured by a competitive type immunoassay. Changes in other parameters of the expressed product may be measured by the appropriate assay.

pal Polynucleotides

The present invention provides, inter alia, novel purified and isolated polynucleotides encoding yeast PAL polypeptides. The polynucleotides of the invention include DNA sequences and RNA transcripts, and both sense and complementary antisense strands. DNA sequences of the invention preferably include cDNA or genomic sequences. "Nucleic acid" as used herein refers to an oligonucleotide or polynucleotide sequence, and fragments or portions thereof, and to DNA or RNA of cellular or synthetic origin (or mixtures thereof), which may be double-stranded or single-stranded, whether representing the sense or antisense strand. The term nucleic acid is used interchangeably with the term "polynucleotide", which can have any length. By comparison, an "oligonucleotide" is a nucleic acid species that has less than about 50 bp. An exemplary double-stranded polynucleotide according to the invention can have a first strand (i.e., a coding strand) having a sequence encoding a PAL polypeptide, along with a second strand (i.e., a "complementary" or "non-coding" strand) having a sequence deducible from the first strand according to the Watson-Crick base-pairing rules for DNA. Double-stranded or "duplex" structures may be DNA:DNA, DNA:RNA, or RNA:RNA nucleic acids. A preferred double-stranded polynucleotide according to the invention is a cDNA having a nucleotide sequence defined by SEQ ID NO:12 (e.g., residues 37 to 2196 or portions thereof) or a genomic DNA having a sequence defined by SEQ ID NO:28 (e.g., residues 1 to 2589 or portions thereof, particularly residues 1 to 361, 449 to 880, 961 to 1295, 1365 to 1529, 1587 to 1748, 1822 to 1947, 2008 to 2589, and/or residues 2008 to 2586). An exemplary single-stranded polynucleotide according to the invention is a messenger RNA (mRNA) encoding a PAL polypeptide. Another exemplary single-stranded polynucleotide is an oligonucleotide probe or primer that hybridizes to the coding or non-coding strand of a polynucleotide defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). Other alternative nucleic acid structures, e.g., triplex structures, are also contemplated by the invention.

The PAL cDNA of the invention comprises the protein-coding region for a PAL polypeptide and includes allelic variants of the preferred polynucleotides of the invention, such as single nucleotide polymorphisms of the wild-type gene. Allelic variants are known in the art to be modified forms of the wild-type (predominant) gene sequence, and which similarly are reflected as changes in cDNA from the variant as compared to cDNA from a wild-type gene. Allelic variants are detected as cDNAs from naturally occurring sequences, as opposed to cDNAs from non-naturally occurring variants, which arise from in vitro manipulation.

The invention in particular comprehends cDNA, which is obtained through reverse transcription of a RNA polynucleotide encoding PAL followed by second strand synthesis of a complementary strand to provide a double-stranded DNA (e.g., as described in the Examples which follow). Also, the invention provides genomic DNA encoding PAL. For instance, the invention desirably provides a cDNA sequence that encodes a polypeptide having the amino acid sequence defined by SEQ ID NO:13. The invention also desirably provides a genomic DNA that encodes a polypeptide having the amino acid sequence of SEQ ID NO:13. In preferred embodiments, the invention provides polynucleotides comprising a nucleotide sequence defined by SEQ ID NO:12 (e.g., residues 37 to 2196 or portions thereof) or by SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586).

As noted, a particularly preferred polynucleotide sequence according to the invention is defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). However, because the genetic code is redundant or "degenerate" in its information-encoding properties, different nucleotide sequences may encode the same polypeptide sequence, as is well known in the art. Accordingly, the invention comprises the alternative (degenerate) nucleotide sequences that encode PAL polypeptides of the invention and functional equivalents thereof. For example, the invention includes polynucleotides comprising nucleotide sequences that are substantially identical to the pal sequence of SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). More particularly, the invention includes polynucleotides whose corresponding nucleotide sequences have at least 80%, preferably at least 90%, more preferably at least 95%, and still more preferably at least 99% identity with a nucleotide sequence defined in SEQ ID NO: 12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586).

Along these lines, the sequence (e.g., one synthesized in a laboratory) can be partially or wholly theoretical, e.g., obtained by reference to or based on a pal polynucleotide or polypeptide sequence. Exemplary theoretical sequences include the derived consensus set forth in SEQ ID NOS:20 and 21.

In particular, the present invention preferably provides an isolated and purified yeast phenylalanine ammonia lyase polynucleotide comprising the sequence of SEQ ID NO:20, wherein residues 117, 135, 190, 191, 195, 276, 1196 to 1198, 1724 to 1735, 1880, 1881, and 2187 to 2475 are absent, residues 13, 34, 46, 115, 164, 251, 266, 315, 330, 333, 340, 348, 423, 450, 456, 468, 555, 570, 675, 681, 716, 723, 783, 921, 1176, 1380, 1383, 1407, 1446, 1449, 1452, 1488, 1542, 1554, 1563, 1617, 1677, 1683, 1776, 1872, 1895, 1950, 1971, and 1976 are B (i.e., are selected from the group consisting of C or G or T (or U)), residues 49, 119, 331, 463, 715, 1270, 1684, 1708, 1762, 1768, 2001, 2145, and 2183 are D (i.e., are selected from the group consisting of A or G or T (or U)), residues 59, 73, 102, 145, 233, 264, 357, 483, 758, 1042, 1241, 1470, 1509, 1690, 1745, 1962, and 2151 are H (i.e., are selected from the group consisting of A or C or T (or U)), residues 51, 57, 144, 168, 201, 312, 405, 475, 963, 1043, 1281, 1308, 1675, 1678, 1681, 1693, 1952, and 2146 are V (i.e., are selected from the group consisting of A or C or G), residues 79, 729, 1710, and 1873 are Y (i.e., are selected from the group consisting of C or T (or U)), residues 84, 199, and 1723 are W (i.e., are selected from the group consisting of A or T (or U)), residues 82, 200, 732, and 744 are S (i.e., are selected from the group consisting of C or G), residues 106, 108, 284, and 743 are M (i.e., are selected from the group consisting of A or C), residue 730 is K (i.e., are selected from the group consisting of G or T (or U)), residues 76 and 77 are A, residues 68, 75, 1855, 1857, 1858, 1860, 1862, and 1874 are C, and residues 69, 1856, 1859, 1861, 1875 are T. The invention further desirably provides an isolated and purified yeast phenylalanine ammonia lyase polynucleotide comprising the sequence of SEQ ID NO:29.

As used herein, "identity" is a measure that can be used to compare sequences. Identity differs from "homology", which is a conclusion drawn from identity or similarity data that two sequences (i.e., genes) share a common evolutionary history. In particular, identity is the number of positions in an alignment of sequences that have the same residue (i.e., amino acid or nucleic acid). Percent sequence identity with respect to polynucleotides of the invention can be defined as the percentage of nucleotide bases in a candidate sequence that are identical to nucleotides in the pal-encoding sequence after aligning the sequences and introducing gaps, if necessary, to achieve maximum percent sequence identity. Computer software is available (from commercial and public domain sources) for calculating percent identity in an automated fashion. Similarity is the number of positions in an alignment of sequences that have a similar residue (i.e., amino acid residue, this is not done for nucleic acid sequences).

In particular, alignment of nucleotide sequences for purposes of similarity comparisons can be done using, e.g., the standard tools BLAST (Basic Local Alignment Tool, Altschul et al., *Meth. Enzymol.,* 266, 466–480 (1996), or, the nucleotide derivatives of this program, BLASTN (compares a nucleotide query against a nucleotide sequence database), BLASTX (compares the six-frame conceptual translation of a nucleotide query sequence (both strands) against a protein sequence database (Madden et al., *Meth. Enzymol.,* 266, 131–140 (1996)) or FASTA (Pearson, *Proc. Natl. Acad. Sci.,* 85, 2444–2448 (1988)). Other appropriate programs similarly can be employed for sequence alignment and sequence comparison such as is known in the art. A particularly preferred program for making such comparisons is Clustal W.

Variant polynucleotides of the invention further include fragments of the nucleotide sequence defined in SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586) and homologs thereof. The disclosure of full-length polynucleotides encoding PAL polypeptides makes readily available to the person having ordinary skill in the art every possible fragment of the full-length polynucleotides. For instance, these can be produced by cleavage of the full length protein, or by synthesis of only a portion of the protein (i.e., using recombinant or chemical means). Preferably, fragment polynucleotides of the invention comprise sequences unique to the PAL-encoding nucleotide sequence, and therefore hybridize under highly stringent or moderately stringent conditions only (i.e., specifically) to polynucleotides encoding PAL or fragments thereof containing the unique sequence. Polynucleotide fragments of cDNA sequences of the invention can comprise not only sequences unique to the coding region, but also include fragments of the full-length sequence derived from untranslated sequences (e.g., the leader sequence). Sequences unique to polynucleotides of the invention are recognizable through sequence comparison to other known polynucleotides, and can be identified through use of computer software routinely used in the art, e.g., alignment programs available in public sequence databases, as previously described.

The invention also provides fragment polynucleotides that are conserved in one or more polynucleotides encoding members of the PAL family of polypeptides. Such fragments include sequences characteristic of PAL polypeptides, referred to as "signature" sequences. The conserved signature sequences many times can be discerned following simple sequence comparison of polynucleotides-encoding members of the PAL family. Polynucleotide fragments of the invention can be labeled in a manner that permits their detection, including radioactive and non-radioactive labeling.

Hybridization according to the invention includes the process of forming partially or completely double-stranded nucleic acid molecules through sequence-specific association of complementary single-stranded nucleic molecules. The invention, therefore, further encompasses the use of nucleic acid species that hybridize to the coding or non-coding strands of a polynucleotide that encodes a PAL protein. Preferred hybridizing species hybridize to the coding or non-coding strand of the nucleotide sequence defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). Also encompassed by the present invention are species that would hybridize to a PAL-encoding polynucleotide but for the redundancy of the genetic code, i.e., polynucleotides that encode the same amino acid sequence but rely on different codon usage.

Hybridizing species include, for example, nucleic acid hybridization or amplification probes (e.g., oligonucleotides or polynucleotides) that are capable of detecting nucleotide sequences (e.g., cDNA or genomic sequences) encoding PAL or closely related molecules, such as cDNAs of genomic alleles. The specificity of the probe, i.e., whether it is derived from a highly conserved, conserved, or non-conserved region or domain, and the stringency of the hybridization or amplification conditions (high, intermediate, or low) will determine whether the probe identifies only cDNAs made naturally occurring PAL, or made from related sequences. Probes for the detection of related nucleotide sequences are selected from conserved or highly conserved regions of PAL family members and such probes may be used in a pool of degenerate probes. For the detection of identical nucleotide sequences, or where maximum specificity is desired, oligonucleotide probes are selected from the non-conserved nucleotide regions or unique regions of pal polynucleotides. As used herein, the term "non-conserved nucleotide region" refers to a nucleotide region that is unique to pal disclosed herein and does not occur in related pal family members.

Specificity of hybridization is typically characterized in terms of the degree of stringency of the conditions under which the hybridization is performed. The degree of stringency of hybridization conditions can refer to the melting temperature ($T_m$) of the nucleic acid binding complex (see, e.g., Berger and Kimmel, "Guide to Molecular Cloning Techniques," *Methods in Enzymology,* Vol. 152, Academic Press, San Diego Calif. (1987)). "Maximal stringency" typically occurs at about $T_m$–5° C. (5° C. below the $T_m$ of the probe); "high stringency" at about 5° C. to 10° C. below $T_m$; "intermediate stringency" at about 10° C. to 20° C. below $T_m$; and "low stringency" at about 20° C. to 25° C. below $T_m$.

Also, the stringency of hybridization can refer to the physicochemical conditions employed in the procedure. To illustrate, exemplary moderately stringent hybridization conditions are: hybridization in 3× saline sodium citrate (SSC), 0.1% sarcosyl, and 20 mM sodium phosphate, pH 6.8, at 65° C.; and washing in 2×SSC with 0.1% sodium dodecyl sulfate (SDS), at 65° C. Exemplary highly stringent hybridization conditions are: hybridization in 50% formamide, 5×SSC, at 42° C. overnight, and washing in 0.5×SSC and 0.1% SDS, at 50° C. It is understood in the art that conditions of equivalent stringency can be achieved through variation of temperature and buffer, or salt concentration as described Ausubel et al., (Eds.), *Current Protocols in Molecular Biology,* John Wiley & Sons (1994), pp. 6.0.3–6.4.10. Modifications in hybridization conditions can be determined empirically or calculated precisely based on the length of the oligonucleotide probe and the percentage of guanosine/cytosine (GC) base pairing of the probe. The hybridization conditions can be calculated as described in Sambrook et al., (Eds.), *Molecular Cloning: A Laboratory Manual,* Cold Spring Harbor Laboratory Press: Cold Spring Harbor, N.Y. (1989), pp. 9.47–9.51.

The artisan will appreciate that hybridization under more stringent conditions enables the identification of species having a higher degree of homology or sequence identity with the target sequence. By contrast, hybridization under less stringent conditions enables identification of species having a lesser but still significant degree of homology or sequence identity with the target sequence. Therefore, also included within the scope of the present invention are nucleic acid species that are capable of hybridizing to the nucleotide sequence of SEQ ID NO: 12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586) under conditions of intermediate (moderate) to maximal stringency. Preferably, the hybridizing species hybridize to the coding or non-coding strands of a polynucleotide defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586) under highly stringent conditions.

The polynucleotides of the invention include polynucleotides (i.e., nucleic acid species of any length) and oligonucleotides (i.e., nucleic acid oligomers typically from about 5 to about 50 nucleotides in length) that hybridize to either the coding or the non-coding strands of a nucleic acid (e.g., a cDNA or genomic DNA) encoding a PAL amino acid sequence. In particular, the invention comprises polynucleotides and oligonucleotides that hybridize to the coding or non-coding strand of a polynucleotide defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). A length of the polynucleotide or oligonucleotide is preferred such that the polynucleotide or oligonucleotide is capable of hybridizing to the target nucleic acid molecule. With use of an oligonucleotide for hybridization, desirably the oligonucleotide should not be longer than necessary. Accordingly, desirably the oligonucleotide should contain at most from about 30 to 50 nucleotides, preferably at most from about 20 to about 25 nucleotides, and more preferably at most from about 10 to about 15 nucleotides. With use of a polynucleotide for hybridization, optionally a pal fragment contained within a vector can be employed in its entirety for hybridization. Such polynucleotides and oligonucleotides may be used as described herein as primers for DNA synthesis (e.g., as primers in PCR; "amplimers"), as probes for detecting the presence of target DNA in a sample (e.g., northern or Southern blots and in situ hybridization), as therapeutic agents (e.g., in antisense therapy), or for other purposes. Oligonucleotides can be single- or double-stranded, with the double-stranded forms having one or both ends blunted or stepped.

The oligonucleotides may be obtained or derived by known methods from natural sources. Alternatively, the oligonucleotides may be produced synthetically according to methods known in the art. Such methods include, for example, cloning and restriction of appropriate sequences or direct chemical synthesis by any suitable method, such as the phosphotriester method (e.g., see Narang et al., *Methods Enzymol.,* 68, 90 (1979)); the phosphodiester method (e.g., Brown et al., *Methods Enzymol.,* 68, 109 (1979)); the diethylphosphoramidite method (e.g., Beaucage et al., *Tetrahedron Lett.,* 22, 1859 (1981)); the solid support method (e.g., U.S. Pat. No. 4,458,066); and any other appropriate method.

A preferred source for isolation of a polynucleotide that encodes PAL is strain ATCC PTA-2224, as described in Example 5. The present invention accordingly further provides an isolated and purified yeast polynucleotide that encodes a yeast phenylalanine ammonia lyase polypeptide, wherein the polynucleotide preferably is obtained from strain ATCC PTA-2224. The present invention also desirably provides an isolated and purified yeast polynucleotide that encodes the sequence of SEQ ID NO: 13, wherein the polynucleotide is obtained from strain ATCC PTA-2224. The invention further preferably provides an isolated and purified yeast polynucleotide that has the coding sequence specified in SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586), and encodes a yeast phenylalanine ammonia lyase polypeptide, preferably wherein the polynucleotide is obtained from strain ATCC PTA-2224.

The pal polynucleotides of the invention include variants, which are polynucleotides that encode PAL or a functional equivalent thereof, and which can include deletions, insertions, or substitutions of nucleotide residues. As used herein a "deletion" is a change in a nucleotide or amino acid sequence in which one or more nucleotides or amino acid residues, respectively, are absent. As used herein an "insertion" or "addition" is a change in a nucleotide or amino acid sequence that results in the addition of one or more nucleotides or amino acid residues, respectively. As used herein a "substitution" is a change in a nucleotide or amino acid sequence in which one or more nucleotides or amino acids are replaced by different nucleotides or amino acids, respectively.

Polynucleotide variants also included within the scope of the present invention are alleles or alternative naturally occurring forms of pal sequences (e.g., pal cDNA or genomic sequences corresponding to pal genes found in nature). Alleles result from naturally occurring mutations, i.e., deletions, insertions or substitutions, in the genomic nucleotide sequence, which may or may not alter the structure or function or the expressed polypeptides. Each of these types of mutational changes may occur alone, or in combination with the others, one or more times in a given allelic sequence. Single nucleotide polymorphisms (SNPs) may occur, in which a single base mutation may define an altered polypeptide, which in turn may be associated with an overt phenotypic difference. Of course, SNPs may be silent, as they may not change the encoded polypeptide, or any change they do encode may have no effect on phenotype. These changes at the gene level can be reflected in cDNA sequences obtained according to the invention.

The invention further embraces natural homologs of the yeast pal DNA that occur in other yeast species, preferably other species of *Rhodotorula,* and more preferably other microbial species. Such species homologs, in general, share significant homology at the nucleotide level within the protein-coding regions of pal from *R. graminis.* Thus, the invention encompasses polynucleotides that share at least 75%, at least 80%, at least 85%, at least 90%, at least 95%, at least 98%, or at least 99% nucleotide identity with the protein-coding region of a polynucleotide encoding a *R. graminis* PAL polypeptide, e.g., the polynucleotide defined by SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586). Percent sequence "identity" with respect to polynucleotides of the invention can be defined as the percentage of nucleotide bases in a candidate sequence that are identical to nucleotides in the pal-encoding sequence after aligning the sequences and introducing gaps, if necessary, to achieve maximum percent sequence identity. Computer software is available (from commercial and public domain sources) for calculating percent identity in an automated fashion.

The invention includes polynucleotides that have been engineered to selectively modify the cloning, processing, and/or expression of the product encoded by the pal polynucleotide sequence. Mutations may be introduced using techniques well known in the art, e.g., site-directed mutagenesis to insert new restriction sites, to alter glycosylation patterns, or to change codon preferences inherent in the use of certain expression systems, while simultaneously maintaining control of the amino acid sequence of the expressed polypeptide product. For example, codons preferred by a particular prokaryotic or eukaryotic host cell can be selected to increase the rate of pal polynucleotide expression or to produce recombinant RNA transcripts having desirable properties, such as longer half-lives.

The pal polynucleotides can be synthesized, wholly or partly, using chemical methods well known in the art. "Chemically synthesized," as used herein and is understood in the art, refers to purely chemical, as opposed to enzymatic, methods for producing polynucleotides. "Wholly" chemically synthesized polynucleotide sequences are therefore produced entirely by chemical means; "partly" chemically synthesized polynucleotides embrace those wherein only portions of the resulting nucleic acid were produced by chemical means. Suitable chemical methods for synthesizing DNA have been described, e.g., by Caruthers, *Science,* 230, 281–285 (1985), as well as numerous other references.

According to the invention, pal polynucleotides molecules may be modified to increase intracellular stability and half-life. Possible modifications include, but are not limited to, the addition of flanking sequences of the 5' and/or 3' ends of the molecule or the use of phosphorothioate or 2'-O-methyl rather than phosphodiester linkages within the backbone of the molecule. Other modifications such as are known in the art are encompassed by the invention.

The invention also provides pal peptide nucleic acid (PNA) molecules. These pal PNAs are informational molecules that have a neutral "peptide-like" backbone with nucleobases that allow the molecules to hybridize to complementary pal-encoding DNA or RNA with higher affinity and specificity than corresponding oligonucleotides. Such PNA molecules find particular utility in in vitro applications.

A Construct According to the Invention

The invention also provides a construct, e.g., a construct comprising or encoding a PAL polypeptide sequence according to the invention. A "construct" is any form of molecule in which a polypeptide sequence according to the invention or its encoding polynucleotide sequence is joined to or forms part of a larger molecule. The connection between the pal polynucleotide and/or PAL polypeptide sequence and its site of attachment in the molecule preferably can be by a noncovalent bond (e.g., as in antibody/antigen binding), or by a covalent bond.

Along these lines, a "construct" includes, but is not limited to a vector (e.g., having genetic incorporation of a polypeptide coding sequence into a polynucleotide vector), or a conjugate-type vector (e.g., wherein a coding sequence, polypeptide sequence, or other moiety is noncovalently associated with a vector), or other appropriate moiety that can be employed for effecting cell entry. As used herein a "vector" is a vehicle capable of effecting entry into a cell, e.g., particularly for gene transfer, and has the general meaning of that term as understood by those of skill in the art. Preferably a vector according to the invention comprises a nucleic acid sequence that encodes a PAL polypeptide according to the invention. Optionally, the nucleic acid coding sequence can be so arranged on the vector as to form, upon translation, a fusion protein or antibody fusion (e.g., by juxtaposition of the coding sequence with other coding sequences).

The vectors according to the invention include, but are not limited to, plasmids, phages, and viruses. In particular, desirably the vector comprises a nucleic acid sequence that encodes a PAL polypeptide sequence (i.e., SEQ ID NO:13), as further described herein. The vectors according to the invention are not limited to those that can be employed solely for intracellular delivery, but also include intermediary-type vectors (e.g., "transfer vectors") that can be employed in the construction of other vectors, for instance, in the construction of other vectors that are used in the construction of those vectors that are actually employed to contact cells.

In terms of a viral vector (particularly a retroviral vector, especially a replication-deficient viral vector), such a vector can comprise either complete capsids (i.e., including a viral genome such as a retroviral genome) or empty capsids (i.e., in which a viral genome is lacking, is incomplete, or is degraded, e.g., by physical or chemical means). Preferably the viral vector comprises complete capsids, i.e., as a means of carrying one or more moieties. Since methods are available for transferring viruses, plasmids, and phages in the form of their nucleic acid sequences (i.e., RNA or DNA), a vector similarly can comprise RNA or DNA, in the absence of any associated protein such as capsid protein, and in the absence of any envelope lipid. Similarly, since liposomes effect cell entry by fusing with cell membranes, a vector can comprise liposomes, with nucleic acids encoding the coat protein. Such liposomes are commercially available, for instance, from Life Technologies, Bethesda, Md. (now Invitrogen, Carlsbad, Calif.), as well as from other vendors, and can be used according to the recommendations of the manufacturer. The PAL polypeptide or pal polynucleotide (as produced using methods described herein) can be added to the liposomes either after the liposomes are prepared according to the manufacturer's instructions, or during the preparation of the liposomes.

As stated previously, a PAL polypeptide according to the invention can comprise a fusion protein or antibody fusion. Such a fusion protein or antibody fusion can be produced by means of a vector, e.g., wherein the PAL polypeptide encoding sequence, optional spacer sequence, and further peptide sequence, are in their nucleic acid form, and are operably linked so as to form a "passenger gene". Preferably a passenger gene is capable of being expressed in a cell in which the vector has been internalized. A "spacer" sequence is an optional sequence that desirably can be employed to ensure the appropriate spacing of nucleic acid sequences. Preferably the spacer can comprise either coding or noncoding DNA, and desirably comprises from about 1 to about 1000 bp, preferably from about 1 to about 100 bp, and even more preferably from about 1 to about 10 bp.

A "nucleic acid" is a polynucleotide (DNA or RNA). A "gene" is any nucleic acid sequence coding for a protein or a nascent RNA molecule. A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. Whereas a gene can comprise coding sequences plus any non-coding sequences (e.g., introns, and optionally regulatory sequences such as promoters and the like), a "coding sequence" or "coding region" does not include any non-coding (e.g., regulatory) DNA. The coding sequence of the pal genomic DNA is interrupted by introns. A gene or coding sequence is recombinant if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and can be provided in the form of either DNA, PNA (peptide nucleic acid), or RNA.

Non-coding sequences or regulatory sequences include (but are not limited to) promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

The foregoing describes standard experiments that are easily done by and well known to one skilled in the art. Automated equipment for polypeptide or DNA synthesis is commercially available. Host cells, cloning vectors, DNA expression controlling sequences, oligonucleotide linkers, and other reagents and components are also commercially available.

Method of Intracellular Delivery

The PAL polynucleotide and/or polypeptide sequences of the invention optionally can be introduced intracellularly for various applications (as well as to facilitate production and isolation of PAL). According to the invention, a cell can be any cell, and, preferably, is either a eukaryotic cell or a prokaryotic cell. A eukaryotic cell is a cell which possesses a nucleus surrounded by a nuclear membrane. Preferably for in vitro applications (e.g., industrial applications), the eukaryotic cell is of a unicellular species (e.g., a unicellular yeast cell), and, for therapeutic/diagnostic applications (e.g., in vivo applications) is a mammalian (optimally, human) cell.

Cells that can be employed for applications other than industrial applications thus include, but are not limited to, a wide variety of different cell types such as avian cells, and mammalian cells including but not limited to rodent, primate (such as chimpanzee, monkey, ape, gorilla, orangutan, or gibbon), feline, canine, ungulate (such as ruminant or swine), as well as, in particular, human cells. For in vitro applications including industrial applications, the cell preferably is any species of *Escherichia, Bacillus, Schizosaccharomyces, Pichia, Saccharyomyces,* *Streptomyces, Pseudomonas, Erwinia,* and *Clostridia,* and desirably the cell is a yeast cell. For industrial applications, it particularly is preferred that that host organism is an industrial strain (i.e., a production strain), such as an industrial strain of *Escherichia coli, Bacillus subtilis, Pichia pastoris, Saccharomyces cerevisiae, Schizosaccharomyces pombe, Pseudomonas putida, Erwinia chrysanthemi, Bacillus stearothermophilus, Erwinia* sp., *Clostridia* sp., *Rhodosporidum, Toruloides,* and the like. Desirably a cell is one in which the pal polynucleotide sequence is stably maintained, or at least is maintained for a period of time (i.e., typically from anywhere up to three months, and potentially even after three months, including indefinitely) after entry into the cell. Optimally, nascent RNA is transcribed from the pal sequences, as further described herein.

A cell thus can be present as a single entity, or can be part of a larger collection of cells. Such a "larger collection of cells" can comprise, for instance, a cell culture (either mixed or pure), a tissue (e.g., muscle or other tissue), an organ (e.g., heart, lung, liver, gallbladder, urinary bladder, eye, and other organs), an organ system (e.g., skeletal system, circulatory system, respiratory system, gastrointestinal system, urinary system, nervous system, integumentary system or other organ system), or an organism (e.g., a bird, non-human mammal, human, or the like).

The method by which introduction into a cell of a construct, polypeptide, or polynucleotide according to the invention is accomplished comprises contacting the cell with the moiety, preferably so as to result in a cell having it transferred therein. Such "contacting" can be done by any means known to those skilled in the art, and described herein, by which the apparent touching or mutual tangency of the cell and the moiety can be effected. For instance, contacting can be done by mixing these elements in a small volume of the same solution. Alternately, the cell and the moiety need not necessarily be brought into contact in a small volume, as, for instance, in cases where the construct, polypeptide or polynucleotide is administered to a host, and travels within the host by the bloodstream or other bodily fluid.

The method of the present invention can be employed to contact cells that are located either in vitro or in vivo, for instance for research, diagnosis, or therapy (e.g., reduction of PKU), or for industrial uses (e.g., manufacture of phenylalanine, phenylalanine analogs, and other optically active unnatural amino acids having phenylalanine-like structures). According to the invention "contacting" comprises any means by which a product is introduced intracellularly; the method is not dependent on any particular means of introduction and is not to be so construed. Means of introduction are well known to those skilled in the art, and also are exemplified herein.

Accordingly, introduction of the products of the invention (e.g., vectors, compositions, polynucleotides and/or polypeptides) can be effected, for instance, either in vitro (e.g., in an ex vivo type method of gene therapy or in tissue culture studies) or in vivo by electroporation, transformation, transduction, conjugation or triparental mating, (co)transfection, (co-)infection, membrane fusion with cationic lipids, high velocity bombardment with DNA-coated microprojectiles, incubation with calcium phosphate-DNA precipitate, direct microinjection into single cells, and the like. Similarly, the products can be introduced by means of cationic lipids, e.g., liposomes. Such liposomes are commercially available (e.g., Lipofectin® Lipofectamin™, and the like, supplied by Life Technologies, GIBCO BRL, Gaithersburg, Md. (now Invitrogen, Carlsbad, Calif.), and other commercial vendors). Also, low levels of the polynucleotides and/or polypeptides may spontaneously be taken up by the cells. Other methods also are available and are known to those skilled in the art.

One skilled in the art will appreciate that suitable methods of administering a product of the present invention to an animal (e.g., a human) for purposes of gene therapy, chemotherapy, cell marking, and the like are available, and, although more than one route can be used for administration, a particular route can provide a more immediate and more effective reaction, or a more convenient or less invasive means, than another route.

PAL Polypeptide Production Systems

Knowledge of PAL-encoding DNA sequences enables the artisan to modify cells to permit or increase production of PAL. Accordingly, host cells are provided, including prokaryotic or eukaryotic cells, either stably or transiently modified by introduction of a polynucleotide of the invention to permit expression of the encoded PAL polypeptide, or stably or transiently modified by introduction of a PAL polypeptide. In particular, these cell systems desirably can be used for the production of PAL polypeptide. With use of industrial host cells (i.e., host cells adapted for high level production of polypeptide under industrial conditions, the cells optimally can be employed in industrial fermentation reactions, e.g., for the production of phenylalanine, phenylalanine analogs, and other optically active unnatural amino acids having phenylalanine-like structures.

The form in which PAL-encoding polynucleotides and PAL polypeptides are introduced into cells is further described above as a "construct" according to the invention. In particular, the invention desirably provides autonomously replicating recombinant expression constructs such as plasmid and viral DNA vectors incorporating PAL-encoding sequences.

The invention further desirably provide expression constructs comprising PAL-encoding polynucleotides operatively linked to an endogenous or exogenous expression control DNA sequence and a transcription terminator. Expression control DNA sequences include promoters, enhancers, and operators, and are generally selected based on the expression systems in which the expression construct is to be used. Preferred promoter and enhancer sequences are generally selected for the ability to increase gene expression, while operator sequences are generally selected for the ability to regulate gene expression. Preferred constructs of the invention also include sequences necessary for replication in a host cell. Expression constructs are preferably used for production of an encoded PAL polypeptide, but may also be used to amplify the construct itself.

Thus, polynucleotides of the invention may be introduced into the host cell desirably as part of a circular plasmid, or as linear DNA comprising an isolated protein coding region, contained on a viral vector, or by any other appropriate means. Methods for introducing DNA in to a host cell include transformation, transfection, electroporation, nuclear injection, or fusion with carriers such as liposomes, micelles, ghost cells, and protoplasts, to name but a few.

Any appropriate expression vector (e.g., as described in Pouwels et al., *Cloning Vectors: A Laboratory Manual* (Elsevier, N.Y.: 1985)) and corresponding suitable host can be employed for production of polypeptides/proteins according to the invention. Expression hosts include, but are not limited to, bacteria, yeast, fungal, mammalian, plant, and insect host cell systems including baculovirus systems (e.g., as described by Luckow et al., *Bio/Technology*, 6, 47 (1988)) to name but a few, and established cell lines such as the COS-7, C127, 3T3, CHO, HeLa, BHK cell line, and the like. Some suitable prokaryotic host cells include, but are not limited to, for example, *E. coli* strains SG-936, HB 101, W3110, X1776, X2282, DHI, and MRC1, *Pseudomonas* species, *Bacillus* species such as *B. subtilis, Salmonella* and *Streptomyces* species. Suitable eukaryotic host cells include yeasts, such as *Saccharomyces cerevisiae, Schizosaccharomyces pombe, Pichia pastoris* and other fungi, insect cells such as sf9 or sf21 cells (*Spodoptera frugiperda*), animal cells such as Chinese hamster ovary (CHO) cells, yeast cells such as JY, 293, and NIH3T3 cells, plant cells such as *Arabidopsis thaliana* cells, as well as any other appropriate cell, especially those previously described herein (section entitled "Method of Intracellular Delivery") for in vitro applications including industrial applications. The pal nucleotide sequence, or any portion of it, may be cloned into a vector for the production of an mRNA probe. Such vectors are known in the art, are commercially available, and may be used to synthesize RNA probes in vitro by addition of labeled nucleotides and an appropriate RNA polymerase such as T7, T3, or SP6.

The ordinary skilled artisan is, of course, aware that the choice of expression host has ramifications for the type of polypeptide/protein produced. For instance the glycosylation of peptides produced in yeast or mammalian cells (e.g., COS-7 cells) will differ from that of peptides produced in bacterial cells such as *Escherichia coli*. The type of host cell, the form of the expressed PAL product, the conditions of growth, and the like, can be selected by the skilled artisan according to known criteria. Use of microbial host cells, particularly yeast host cells, is expected to provide for such post-translational modifications (e.g., glycosylation, truncation, lipidation, and phosphorylation) as may be needed to confer optimal biological activity on recombinant expression products of the invention. Glycosylated and non-glycosylated forms of PAL polypeptides are embraced. The protein produced by a recombinant cell preferably may be secreted or may be contained intracellularly, depending on the sequence and/or the vector used. As will be understood by those of skill in the art, expression vectors containing pal polynucleotide sequences can be designed with signal sequences that direct secretion of PAL through a particular prokaryotic or eukaryotic cell membrane.

Similarly, in the different hosts, the nature of the non-coding DNA upstream of the pal coding region should be composed of transcription/translation signals appropriate for the host. Optimally, transcriptional signals such as those of *S. cerevisiae* phosphoglycerate kinase and mating factor genes should be placed 5' to the ribosome binding site. The construct employed optionally can use standard replicons (e.g., 2 µm) and selectable markers (e.g., Leu2, Trp, and the like) to select for continued maintenance of the construct. For use in *E. coli*, well known promoters such as lambda PL, tac, trp, rac, or lac, as well as others, optionally can be employed, preferably with use of appropriate bacterial ribosome binding sites. For such constructs, optionally Co/EI, RSF1010, and RI (runaway) replicons can be employed.

Host cells of the invention are useful in methods for large-scale production or use of PAL polypeptide products. For example, recombinant PAL can be produced and isolated from host cells for use in in vitro binding assays such as drug screening assays. In such methods, the host cells are grown in a suitable culture medium and the desired polypeptide product is isolated from the cells or from the medium in which the cells are grown. Such host cells (e.g., industrial or producing strains) similarly can be employed in industrial fermentation cultures for producing phenylalanine, phenylalanine analogs, and other optically active unnatural amino acids having phenylalanine-like structures.

The polypeptide product optionally can be isolated by purification methods known in the art, and as described in the following examples, and including such conventional chromatographic methods such as immunoaffinity chromatography, receptor affinity chromatography, hydrophobic interaction chromatography, lectin affinity chromatography, size exclusion filtration, cation or anion exchange chromatography, high performance liquid chromatography (HPLC), reverse-phase HPLC, and the like.

Still other methods of purification include those in which the desired protein is expressed and purified as a fusion protein in which the PAL polypeptide is ligated to a heterologous amino acid sequence. Suitable heterologous sequences can include a specific tag, label, or chelating moiety that is recognized by another agent. For example, it is possible to produce a PAL protein fused to a selected heterologous protein selected to be specifically identifiable. A fusion protein also may be engineered to contain a cleavage site (e.g., a factor XA or enterokinase sensitive sequence) located between the PAL sequence and the heterologous protein sequence, to permit the PAL protein to be cleaved from the heterologous protein and subsequently purified. Cleavage of the fusion component may produce a form of the desired protein having additional amino acid residues resulting from the cleavage process.

Exemplary heterologous peptide domains include metal-chelating peptides such as histidine-tryptophan modules that allow purification on immobilized metals (Porath, *Protein Expr. Purif.*, 3:263–281 (1992)), and protein A domains that allow purification on immobilized immunoglobulin. Another useful system is the divalent cation-binding domain and antibodies specific thereto used in the peptide extension/immunoaffinity purification system, for instance, as described in U.S. Pat. Nos. 4,703,004, 4,782,137, 4,851,431, and 5,011,912. This system is commercially available as the FLAG® system from Immunex Corp. (Seattle Wash.). Another suitable heterologous fusion partner is glutathione S-transferase (GST), which can be affinity purified using immobilized glutathione. Other useful fusion partners include immunoglobulins and fragments thereof, e.g., Fc fragments.

Identification of host cells expressing recombinant PAL in certain instances may be helpful in identifying appropriate expression systems. Accordingly, expression constructs of the invention may also include sequences encoding one or more selectable markers that permit identification of host cells bearing the construct in operative condition. It is also contemplated that, in addition to the insertion of heterologous promoter DNA, amplifiable marker DNA (e.g., ada, dhfr, and the multifunctional CAD gene that encodes carbamyl phosphate synthase, aspartate transcarbamylase, and dihydroorotase, to name but a few) and/or intron DNA may be inserted along with the heterologous promoter DNA. If linked to the PAL-encoding sequence, amplification of the marker DNA by standard selection methods results in co-amplification of the PAL-encoding sequences in the cells. Detection of expression of the marker gene in response to induction or selection usually indicates expression of pal as well. Alternatively, if the pal polynucleotide is inserted within a marker gene sequence, recombinant cells containing pal can be identified by the absence of marker gene function.

Host cells that contain the coding sequence for PAL and that express pal also may be identified by a variety of other procedures known to those of skill in the art. These procedures include, but are not limited to, PCR amplification, hybridization, enzyme assay, or immunoassay techniques, that include membrane-based, solution-based, or chip-based technologies for the detection and/or quantification of the nucleic acid or protein. For measuring PAL activity, preferably an enzyme assay is performed.

The presence of the pal polynucleotide sequence can be detected by DNA-DNA or DNA-RNA hybridization or amplification using fragments of pal disclosed in SEQ ID NO:12 (e.g., residues 37 to 2196 or portions thereof) or SEQ ID NO:28 (e.g., residues 1 to 2589 or portions, thereof, particularly residues 1 to 361, 449 to 880, 961 to 1295, 1365 to 1529, 1587 to 1748, 1822 to 1947, 2008 to 2589, and/or residues 2008 to 2586) as probes. Nucleic acid amplification-based assays involve the use of oligonucleotides based on the pal sequence to detect transformants containing pal DNA or RNA. Labeled hybridization or PCR probes for detecting pal polynucleotide sequences can be made by various methods, including oligolabeling, nick translation, and end-labeling. Pal polynucleotides preferably are detected by PCR amplification.

In one embodiment of the present invention, PAL or a variant thereof and/or a host cell line that expresses the PAL or variant thereof may be used to screen for antibodies, peptides, or other molecules, such as organic or inorganic molecules, that act as modulators of a biological or immunologic activity of PAL. For example, anti-PAL antibodies capable of neutralizing the activity of PAL may be used in vivo (i.e., in yeast cells or others) to inhibit PAL-mediated activity. Alternatively, screening of peptide libraries or organic libraries made by combinatorial chemistry with recombinantly expressed pal or variants thereof, or cell lines expressing PAL or variants thereof, may be useful for identification of therapeutic molecules that function by modulating a biological or immunologic activity of PAL. Synthetic compounds, natural products, and other sources of potentially biologically active materials can be screened in a number of ways deemed routine by those of skill in the art.

PAL Polynucleotide and Polypeptide Probes

The present invention further provides a method of detecting the presence of a PAL-encoding polynucleotide or a PAL polypeptide in a sample. The method involves use of a labeled probe that recognizes the presence of a defined target in the sample. The probe preferably is an antibody that recognizes a PAL polypeptide, or an oligonucleotide (or polynucleotide) that recognizes a polynucleotide encoding PAL polypeptide.

The probes of the invention can be detectably labeled in accordance with methods known in the art. In general, the probe can be modified by attachment of a detectable label (reporter) moiety to the probe, or a detectable probe can be manufactured with a detectable label moiety incorporated therein. The detectable label moiety can be any detectable moiety, many of which are known in the art, including radioactive atoms, electron dense atoms, enzymes, chromogens and colored compounds, fluorogens and fluorescent compounds, members of specific binding pairs, and the like.

Methods for labeling oligonucleotide probes have been described, for example, by Leary et al., *Proc. Natl. Acad. Sci., USA.*, 80:4045 (1983); Renz and Kurz, *Nucleic Acids Res.*, 12:3435 (1984); Richardson and Gumport, *Nucleic Acids Res.*, 11:6167 (1983); Smith et al., *Nucleic Acids Res.*, 13:2399 (1985); Meinkoth and Wahl, *Anal Biochem.*, 138:267 (1984). Other methods for labeling polynucleotides are described, for example, in U.S. Pat. Nos. 4,711,955, 4,687,732, 5,241,060, 5,244,787, 5,328,824, 5,580,990, and 5,714,327, and still further methods such as are known in the art can be employed.

Methods for labeling antibodies have been described, for example, by Hunter et al. (1962) and by David et al., *Biochemistry*, 13:1014–1021 (1974). Additional methods for labeling antibodies have been described in U.S. Pat. Nos. 3,940,475 and 3,645,090.

The label moiety according to the invention preferably is radioactive. Some examples of useful radioactive labels include $^{32}P$, $^{125}I$, $^{131}I$, and $^{3}H$. Use of radioactive labels has been described in U.K. patent document No. 2,034,323, and U.S. Pat. Nos. 4,358,535, and 4,302,204.

Some examples of non-radioactive labels that can be employed include, but are not limited to, enzymes, chromogens, atoms and molecules detectable by electron microscopy, and metal ions detectable by their magnetic properties.

Some useful enzymatic labels include enzymes that cause a detectable change in a substrate. Some useful enzymes (and their substrates) include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels has been described, for example, in U.K. 2,019,404, EP 63,879, and by Rotman, *Proc. Natl. Acad. Sci. USA*, 47:1981–91 (1961). Other enzymatic labels similarly can be employed in the invention.

Useful reporter moieties include (but are not limited to), for example, fluorescent, phosphorescent, chemiluminescent, and bioluminescent molecules, as well as dyes. Some specific colored or fluorescent compounds useful in the present invention include, for example, fluoresceins, coumarins, rhodamines, Texas red, phycoerythrins, umbelliferones, Luminol®, and the like. Chromogens or fluorogens, i.e., molecules that can be modified (e.g., oxidized) to become colored or fluorescent or to change their color or emission spectra, are also capable of being incorporated into probes to act as reporter moieties under particular conditions.

The label moieties may be conjugated to the probe by methods that are well known in the art. The label moieties may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, label moieties such as enzymes and chromogens may be conjugated to antibodies or nucleotides by means of coupling agents, such as dialdehydes, carbodiimides, dimaleimides, and the like. The label moiety may also be conjugated to the probe by means of a ligand attached to the probe by a method described above and a receptor for that ligand attached to the label moiety. Any of the known ligand-receptor binding pair combinations is suitable. Some suitable ligand-receptor pairs include, for example, biotin-avidin or biotin-streptavidin, and antibody-antigen.

Methods of Using pal Polynucleotides and PAL Polypeptides

The scientific value of the information contributed through the disclosures of the DNA and amino acid sequences of the present invention is apparent to one skilled in the art. As one series of examples, knowledge of the sequence of a cDNA or a genomic DNA for PAL makes possible (e.g., through use of Southern hybridization or polymerase chain reaction (PCR)) the identification of genomic DNA sequences encoding PAL and pal expression control regulatory sequences, and will aid in mutagenesis to obtain variants which have enhanced enzyme properties. DNA/DNA hybridization procedures carried out with DNA sequences of the invention under moderately to highly stringent conditions are also expected to allow the isolation of DNAs encoding allelic variants of pal. Similarly, non-yeast species genes encoding proteins homologous to PAL can also be identified by Southern and/or PCR analysis. As an alternative, complementation studies can be useful for identifying other yeast PAL products as well as non-yeast proteins, and DNAs encoding the proteins, sharing one or more biological properties of PAL. Oligonucleotides of the invention are also useful in hybridization assays to detect the capacity of cells to express pal. Polynucleotides of the invention may also be the basis for diagnostic methods useful for identifying a genetic alteration in the pal locus that underlies a disease state.

Oligonucleotides and polynucleotides of the invention, as described herein, may be used in methods to amplify DNA for various purposes. "Amplification" according to the method of the invention refers to any molecular biology technique for detection of trace levels of a specific nucleic acid sequence by exponentially amplifying a template nucleic acid sequence. In particular, suitable amplification techniques include such techniques as the polymerase chain reaction (PCR), the ligase chain reaction (LCR) and variants thereof. PCR is known to be a highly sensitive technique, and is in wide use. PCR is described, for example, in Innis et al., *PCR Protocols: A Guide to Methods and Applications*, Academic Press, Inc., San Diego (1990); Dieffenbach and Dveksler, *PCR Primer: A Laboratory Manual*, Cold Spring Harbor Laboratory Press, Plainview N.Y. (1995); and U.S. Pat. Nos. 4,683,195, 4,800,195, and 4,965,188. LCR is more recently developed and is described in Landegren et al. (Science 241:1077 (1988)) and Barany et al. (PCR Methods and Applications 1:5 (1991)). An LCR kit is available from Stratagene. LCR is known to be highly specific, and is capable of detecting point mutations. In certain circumstances, it is desirable to couple the PCR and LCR techniques to improve precision of detection. Other amplification techniques may be employed in accordance to the invention.

Oligonucleotide amplification primers are often provided as matched pairs of single-stranded oligonucleotides; one with sense orientation (5'→3') and one with antisense (3'←5') orientation. Such specific primer pairs can be employed under optimized conditions for identification of a specific gene or condition. Alternatively, the same primer pair, nested sets of oligomers, or even a degenerate pool of oligomers, may be employed under less stringent conditions for detection and/or quantitation of closely related DNA or RNA sequences.

Oligonucleotides and polynucleotides can be used in various methods known in the art to extend the specified nucleotide sequences. These methods permit use of a known sequence to determine an unknown adjacent sequence, thereby enabling detection and determination of upstream sequences such as promoters and regulatory elements. Exemplary methods are described in Gobinda et al., *PCR Methods Applic.*, 2:318–322 (1993)); Triglia et al., *Nucleic Acids Res.*, 16:8186 (1988); Lagerstrom et al., *PCR Methods Applic.*, 1:111–119 (1991); Parker et al., *Nucleic Acids Res.*, 19:3055–3060 (1991). Commercial kits are also available, e.g., the PromoterFinder™ kit available from Clontech (Palo Alto Calif.).

For example, restriction-site polymerase chain reaction is a direct method that uses universal primers to retrieve unknown sequence adjacent to a known locus. See, e.g., Gobinda et al., *PCR Methods Applic.*, 2:318–22 (1993). In this method, genomic DNA is first amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia et al., *Nucleic Acids Res.*, 16:8186 (1988)). The primers may be designed using Oligo 4.0 (National Biosciences, Inc., Plymouth Minn.), or another appropriate program, to be 22–30 nucleotides in length, to have a GC content of 50% or more, and to anneal to the target sequence at temperatures about 68°–72° C. This method uses several restriction enzymes to generate a suitable fragment in the known region of a gene. The fragment is then circularized by intramolecular ligation and used as a PCR template.

Capture PCR is a method for PCR amplification of DNA fragments adjacent to a known sequence in yeast and yeast artificial chromosome (YAC) DNA (Lagerstrom et al., *PCR Methods Applic.*, 1:111–119 (1991)). Capture PCR also requires multiple restriction enzyme digestions and ligations to place an engineered double-stranded sequence into an unknown portion of the DNA molecule before PCR. Parker et al., *Nucleic Acids Res.*, 19:3055–3060 (1991)), teach walking PCR, a method for targeted gene walking that permits retrieval of unknown sequence. PromoterFinder™ is a kit available from Clontech (Palo Alto, Calif.) that uses PCR, nested primers, and special libraries to "walk in" genomic DNA. This process avoids the need to screen libraries and is useful in finding intron/exon junctions.

Such methods can be used to explore genomic libraries to extend 5' sequence and to obtain endogenous pal genomic sequence, including elements such as promoters, introns, operators, enhancers, repressors, and the like. Preferred libraries for screening for full-length cDNAs are ones that have been size-selected to include larger cDNAs. In addition, randomly primed libraries are preferred in that they will contain more sequences that contain the 5' and upstream regions of genes.

The oligonucleotide probes may also be used for mapping the endogenous genomic sequence. The sequence may be mapped to a particular chromosome or to a specific region of the chromosome using well known techniques. These include in situ hybridization to chromosomal spreads (Venna et al., *Yeast Chromosomes: A Manual of Basic Technique*, Pergamon Press, New York N.Y. (1988)), flow-sorted chromosomal preparations, or artificial chromosome constructions such as YACs, bacterial artificial chromosomes (BACs), bacterial P1 constructions, or single chromosome cDNA libraries.

The DNA sequence information provided by the present invention also makes possible the development, e.g., through homologous recombination or "knock-out" strategies (Capecchi, *Science*, 244:1288–1292 (1989)), of microbes that fail to express functional pal or that express a variant of pal. Such microbes are useful as models for studying the activities of PAL.

As described herein, the invention provides antisense nucleic acid sequences that recognize and hybridize to polynucleotides encoding PAL. Modifications of gene expression can be obtained by designing antisense sequences to the control regions of the pal gene, such as the promoters, enhancers, and introns. Oligonucleotides derived from the transcription initiation site, e.g., between −10 and +10 regions of the leader sequence, are preferred. Antisense RNA and DNA molecules may also be designed to block translation of mRNA by preventing the transcript from binding to ribosomes. The worker of ordinary skill will appreciate that antisense molecules of the invention include those that specifically recognize and hybridize to pal DNA (as determined by sequence comparison of pal DNA to DNA encoding other known molecules). The antisense molecules of the invention also include those that recognize and hybridize to DNA encoding other members of the PAL family of proteins. Antisense polynucleotides that hybridize to multiple DNAs encoding other members of the PAL family of proteins are also identifiable through sequence comparison to identify characteristic or signature sequences for the family of PAL proteins. Accordingly, such antisense molecules preferably have at least 95%, more preferably at least 98%, and still more preferably at least 99% identity to the target pal sequence.

Antisense polynucleotides are particularly relevant to regulating expression of pal by those cells expressing pal mRNA. Antisense polynucleotides (preferably 10 to 20 bp oligonucleotides) capable of specifically binding to pal expression control sequences or pal RNA are introduced into cells, e.g., by a viral vector or a colloidal dispersion system such as a liposome. The antisense oligonucleotide binds to the pal target nucleotide sequence in the cell and prevents transcription or translation of the target sequence. Phosphorothioate and methylphosphonate antisense oligonucleotides are specifically contemplated for therapeutic use under the invention. The antisense oligonucleotides may be further modified by poly-L-lysine, transferrin polylysine, or cholesterol moieties at their 5' ends. For a recent review of antisense technology, see Delihas et al., *Nature Biotechnology*, 15:751–753 (1997).

The invention further comprises methods to modulate pal expression by means of ribozyme technology. For a review, see Gibson and Shillitoe, *Mol. Biotechnol.*, 7:125–137 (1997). Ribozyme technology can be used to inhibit translation of pal mRNA in a sequence-specific manner through: (i) the hybridization of a complementary RNA to a target mRNA; and (ii) cleavage of the hybridized mRNA through endonuclease activity inherent to the complementary RNA. Ribozymes can be identified by empirical methods such as using complementary oligonucleotides in ribonuclease protection assays, but more preferably are specifically designed based on scanning the target molecule for accessible ribozyme cleavage sites (Bramlage et al., *Trends Biotechnol.*, 16:434–438 (1998)). Delivery of ribozymes to target cells can be accomplished using either exogenous or endogenous delivery techniques well known and practiced in the art. Exogenous methods can include use of targeting liposomes or micro-injection. Endogenous methods include use of viral vectors and non-viral plasmids.

Ribozymes can specifically modulate expression of pal when designed to be complementary to regions unique to a polynucleotide encoding PAL. "Specifically modulate," therefore is intended to mean that ribozymes of the invention recognize only a polynucleotide encoding PAL. Similarly, ribozymes can be designed to modulate expression of all or some of the PAL family of proteins. Ribozymes of this type are designed to recognize nucleotide sequences conserved all or some of the polynucleotides encoding the PAL family members.

The invention further embraces methods to modulate transcription of pal through use of oligonucleotide-directed triple helix formation (also known as Hogeboom base-pairing methodology). For a review, see Lavrovsky et al., Biochem. Mol. Med., 62:11–22 (1997). Triple helix formation is accomplished using sequence-specific oligonucleotides that hybridize to double stranded DNA in the major groove as defined in the Watson-Crick model. This triple helix hybridization compromises the ability of the original double helix to open sufficiently for the binding of polymerases, transcription factors, or regulatory molecules. Preferred target sequences for hybridization include promoter and enhancer regions to permit transcriptional regulation of pal expression. Oligonucleotides that are capable of triple helix formation can alternatively be coupled to DNA damaging agents, which can then be used for site-specific covalent modification of target DNA sequences. See Lavrovsky et al. supra.

Both antisense RNA and DNA molecules and ribozymes of the invention can be prepared by any method known in the art for the synthesis of RNA molecules. These include techniques for chemically synthesizing oligonucleotides such as solid-phase phosphoramidite chemical synthesis. Alternatively, RNA molecules may be generated by in vitro or in vivo transcription of DNA sequences encoding the antisense RNA molecule. Such DNA sequences can be incorporated into a variety of vectors with suitable RNA polymerase promoters such as T7 or SP6. Alternatively, antisense cDNA constructs that synthesize antisense RNA constitutively or inducibly can be introduced into cell lines, cells, or tissues.

Mutations in a gene that result in loss of normal function of the gene product may exhibit a deleterious phenotype in yeast, and introduction of the gene in mammals may have a beneficial effect. The invention thus comprehends introduction of the gene (i.e., "gene therapy") to either introduce or restore PAL activity as indicated in treating those disease states characterized by a deficiency or absence of phenylalanine ammonia lyase activity associated with the PAL enzyme. Delivery of functional PAL-encoding sequence to appropriate cells is effected ex vivo, in situ, or in vivo by use of vectors, and more particularly viral vectors (e.g., adenovirus, adeno-associated virus, or retrovirus), or ex vivo by use of physical DNA transfer methods (e.g., liposomes or chemical treatments). See, for example, Anderson, *Nature*, 392(6679 Suppl):25–30 (1998). Alternatively, it is contemplated that in other disease states, preventing the expression or inhibiting the activity of PAL will be useful in treating those disease states. Antisense therapy or gene therapy can be applied to negatively regulate the expression of pal polynucleotide sequences.

The DNA and amino acid sequence information provided by the present invention also makes possible the systematic analysis of the structure and function of PAL proteins. DNA and amino acid sequence information for PAL also permits identification of molecules with which a PAL polypeptide will interact. Agents that modulate (i.e., increase, decrease, or block) PAL activity may be identified by incubating a putative modulator with PAL and determining the effect of the putative modulator on PAL activity. The selectivity of a compound that modulates the activity of the PAL polypeptide can be evaluated by comparing its activity on the PAL to its activity on other proteins.

Selective modulators may include, for example, antibodies and other proteins or peptides that specifically bind to a PAL polypeptide or a PAL-encoding polynucleotide, oligonucleotides or polynucleotides that specifically bind to PAL-encoding polynucleotides, and other non-peptide compounds (e.g., isolated or synthetic organic molecules) that specifically react with PAL polypeptides or PAL-encoding polynucleotides. Mutant forms of pal, such as those that affect the biological activity or cellular location of the wild-type pal, are also contemplated according to the invention. Still other selective modulators include those that recognize specific regulatory or PAL-encoding nucleotide sequences. Modulators of PAL activity may be therapeutically useful in treatment of a wide range of diseases and physiological conditions in which aberrant PAL activity is involved, or may be useful in the commercial production of phenylalanine, phenylalanine analogs, or other optically-active unnatural amino acids having phenylalanine-like structures.

Given the relationship of phenylalaline with phenylketonuria and potentially cancer, and the use of a phenylalanine-like architecture in the pharmacophores of protease inhibitors presently employed in treating human immunodeficiency virus and human cytomegalovirus infections, a PAL-encoding polynucleotide sequence may be used for the diagnosis of diseases resulting from, associated with, or ameliorated by pal expression or PAL activity e.g., phenylketonuria, cancer, human immunodeficiency virus infection, and/or cytomegalovirus infection. Qualitative or quantitative methods may include Southern or Northern analysis, dot blot, or other membrane-based technologies; PCR technologies; dipstick, pin or chip technologies; and ELISA or other multiple-sample format technologies, which all can be carried out either in the presence or absence of exogenous pal polynucleotide or PAL polypeptide e.g., phenylketonuria, cancer, human immunodeficiency virus infection, and/or cytomegalovirus infection. These types of techniques are well known in the art and have been employed in commercially available diagnostic kits.

Such assays may be tailored to evaluate the efficacy of a particular therapeutic treatment regimen and may be used in animal studies, in clinical trials, or in monitoring the treatment of an individual patient, or can be employed in microbial (e.g., yeast studies). To provide a basis for the diagnosis of disease, a normal or standard profile for pal expression must be established. This is accomplished by combining a biological sample taken from a normal subject with a pal polynucleotide, under conditions suitable for hybridization or amplification. Standard hybridization may be quantified by comparing the values obtained for normal subjects with a dilution series of positive controls run in the same experiment where a known amount of a purified pal polynucleotide is used. Standard values obtained from normal samples may be compared with values obtained from samples from subjects (or yeast samples) potentially affected by a disorder or disease related to pal expression. Deviation between standard and subject values establishes the presence of the disease state. If disease is established, an existing therapeutic agent is administered, if so desired, and treatment profile or values may be generated. The assay may be repeated on a regular basis to evaluate whether the values progress toward or return to the normal or standard pattern. Successive treatment profiles may be used to show the efficacy of treatment over a period of several days or several months.

In particular, anti-PAL antibodies may be useful for the diagnosis of conditions, disorders, or diseases characterized by or associated with abnormal expression of a PAL polypeptide, and/or to detect yeast aberrant or excessive PAL production. Assays (including diagnostic assays) for PAL polypeptides include methods that employ a labeled antibody to detect a PAL polypeptide in a biological sample such as a body fluid, cells, tissues, sections, or extracts of such materials. Preferably, the polypeptide or the antibody will be labeled by linking them, either covalently or noncovalently, with a detectable label moiety as described herein. Antibody-based methods for detecting the presence of PAL polypeptides in biological samples are based on previously described assays for detecting the presence of proteins with antibodies, and follow known formats, such as enzyme-linked immunosorbent assay (ELISA), radioimmunoassay (RIA), and X fluorescence-activated cell sorting (FACS) and flow cytometry, Western analysis, sandwich assays, and the like. These formats are normally based on incubating an antibody with a sample suspected of containing the PAL protein and detecting the presence of a complex between the antibody and the protein. The antibody is labeled either before, during, or after the incubation step. The specific concentrations of antibodies, the temperature and time of incubation, as well as other such assay conditions, can be varied, depending upon various factors including the concentration of antigen in the sample, the nature of the sample, etc. Those skilled in the art will be able to determine operative and optimal assay conditions for each determination by employing routine experimentation. See, e.g., Hampton et al., *Serological Methods: A Laboratory Manual*, APS Press, St Paul Minn. (1990).

To provide a basis for the quantitation of PAL protein in a sample or for the diagnosis of disease, normal or standard values of PAL polypeptide expression must be established. This is accomplished by combining body fluids or cell extracts taken from a normal sample or from normal subjects, either animal or yeast, with antibody to a PAL polypeptide. The amount of standard complex formation may be quantified by comparing it with a dilution series of positive controls where a known amount of antibody is combined with known concentrations of a purified PAL polypeptide. Then, standard values obtained from normal samples may be compared with values obtained from samples from test sample, e.g., subjects potentially affected by a disorder or disease related to pal expression. Deviation between standard and test values establishes the presence of the disease state.

The invention further provides a method for increasing the expression or activity of PAL (i.e., including "increasing" in the sense of supplying this activity to a host that normally does not contain it) and/or for industrial uses. The method comprises administering a pal polynucleotide, a PAL polypeptide, and/or a PAL agonist in an amount effective for increasing pal expression or PAL activity. This method may be employed in yeast or mammals. As employed in mammals, the method may prove useful in the treatment of any condition whose symptoms or pathology is mediated by or ameliorated by pal expression or PAL activity (e.g., for mammals, phenylketonuria and/or cancer prophylaxis/therapeutics). In terms of industrial uses (e.g., in yeast or other appropriate production host), PAL produced by recombinant means can be used in the commercial production of phenylalanine, phenylalanine analogs, and other optically active unnatural amino acids having phenylalanine-like structures. For instance, the enzyme can be employed instead of a fermentation culture for the production of phenylalanine, phenylalanine analogs, and other optically active unnatural amino acids having phenylalanine-like structures, or can be added into a fermentation culture that already contains a PAL producing strain. Other possibilities and variations would be apparent to those skilled in the art.

"Treating" as used herein refers to preventing a disorder from occurring in a mammal (especially a human) that may be predisposed to the disorder, but has not yet been diagnosed as having it; inhibiting the disorder, i.e., arresting its development; relieving the disorder, i.e., causing its regression, or ameliorating the disorder, i.e., reducing the severity of symptoms associated with the disorder. "Disorder" is intended to encompass medical disorders, diseases, conditions, syndromes, and the like, without limitation.

In particular, the method of the invention may be employed to treat mammals (i.e., especially humans) therapeutically or prophylactically, for instance, mammals that are or may be subject to phenylketonuria. The invention also relates to a method of treating neoplastic tissue growth, e.g., cancer, in a mammal, comprising administering to the mammal an effective amount of PAL. In this embodiment, the method may further comprise adjuvant administration of a chemotherapeutic or anti-cancer drug and/or radiation therapy.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, cancers invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Expression vectors derived from retroviruses, adenovirus, herpes, or vaccinia viruses, or from various bacterial plasmids, may be used for delivery of recombinant pal sense or antisense molecules to the targeted cell population. Methods that are well known to those skilled in the art can be used to construct recombinant vectors containing pal. See, for example, the techniques described in Sambrook et al., supra, and Ausubel et al., supra. Alternatively, recombinant pal can be delivered to target cells in liposomes.

The full-length cDNA or genomic sequences, and/or regulatory elements obtained therefrom, enable researchers to use a pal polynucleotide as a tool in sense (Youssoufian and Lodish, *Mol. Cell. Biol.*, 13:98–104 (1993)) or antisense (Eguchi et al., *Annu. Rev. Biochem.*, 60:631–652 (1991)) investigations of gene function. Oligonucleotides, designed from the cDNA or control sequences obtained from the genomic DNA, can be used in vitro or in vivo to inhibit expression. Such technology is now well known in the art, and sense or antisense oligonucleotides or larger fragments can be designed from various locations along the coding or control regions.

Additionally, pal expression can be modulated by transfecting a cell or tissue with expression vectors that express high levels of a pal polynucleotide fragment in conditions where it would be preferably to block a biological activity of PAL. Such constructs can flood cells with untranslatable sense or antisense sequences. Even in the absence of integration into the DNA, such vectors may continue to transcribe RNA molecules until all copies of the vector are disabled by endogenous nucleases. Such transient expression may be accomplished using a non-replicating vector or a vector incorporating appropriate replication elements.

Methods for introducing vectors into cells or tissue include those methods discussed herein. In addition, several of these transformation or transfection methods are equally suitable for ex vivo therapy. Furthermore, the pal polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Preparation of Antibodies Immunoreactive with PAL Polypeptides

The present invention allows for the production of antibodies with specificity for PAL polypeptide. Antibodies to PAL may be produced by any method known in the art typically including, for example, the immunization of laboratory animals with preparations of purified native PAL, purified recombinant PAL, purified recombinant peptide fragments of PAL, or synthetic peptides derived from the PAL predicted amino acid sequence. This is discussed in Harlow et al. (Eds.), *Antibodies: A Laboratory Manual*, Cold Spring Harbor Laboratory, Cold Spring Harbor N.Y. (1988). Also, antibodies that have been described in the art and are known to react with PAL can be employed according to the invention.

PAL Compositions

The present invention thus further relates to PAL polypeptide-containing compositions including pharmaceutical compositions. Pharmaceutical compositions optionally comprise PAL polypeptide or pal polynucleotide, or comprise a chemical or biological compound ("agent") that is active as a modulator of pal expression or PAL activity, along with a biocompatible pharmaceutical carrier, adjuvant, or vehicle. The active agent in the compositions (e.g., pharmaceutical compositions) accordingly may be selected from among all or portions of pal polynucleotide sequences, pal antisense molecules, PAL polypeptides, protein, peptide, or organic modulators of PAL bioactivity, such as inhibitors, antagonists (including antibodies) or agonists. Preferably, the agent is active in treating a medical condition that is mediated by, characterized by, or ameliorated by, pal expression or PAL activity. The composition can include the agent as the only active moiety or in combination with other nucleotide sequences, polypeptides, drugs, or hormones mixed with excipient(s) or other pharmaceutically acceptable carriers. Compositions other than pharmaceutical compositions optionally comprise liquid, i.e., water or a water-based liquid. Desirably, such a composition employed for industrial fermentation optimally contains components necessary for such fermentation, e.g., culture media, plus any stabilizers, additives, antibodies, host cells, or others. A composition employed for industrial fermentation further optionally can comprise added PAL polypeptide.

Pharmaceutically acceptable excipients to be added to pharmaceutical compositions also are well-known to those who are skilled in the art, and are readily available. The choice of excipient will be determined in part by the particular method used to administer the product according to the invention. Accordingly, there is a wide variety of suitable formulations for use in the context of the present invention. The following methods and excipients are merely exemplary and are in no way limiting.

Techniques for formulation and administration of pharmaceutical compositions may be found in *Remington's Pharmaceutical Sciences*, 18th Ed., Mack Publishing Co, Easton Pa., 1990, and are well known to those skilled in the art. The choice of excipient will be determined in part by the particular method used to administer the product according to the invention. Accordingly, there is a wide variety of suitable formulations for use in the context of the present invention. The following methods and excipients are merely exemplary and are in no way limiting.

The pharmaceutical compositions of the present invention may be manufactured using any conventional method, e.g., mixing, dissolving, granulating, dragée-making, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations may influence the physical state, stability, rate of in vivo release, and rate of in vivo clearance of the administered agent. Depending on the condition being treated, these pharmaceutical compositions may be formulated and administered systemically or locally.

The pharmaceutical compositions may be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Surgical techniques include implantation of depot (reservoir) compositions, osmotic pumps, and the like. A preferred route of administration for treatment of inflammation would be local or topical delivery for localized inflammation such as arthritis, and intravenous delivery for reperfusion injury or for systemic conditions such as septicemia.

The pharmaceutical compositions are formulated to contain suitable pharmaceutically acceptable carriers, and may optionally comprise excipients and auxiliaries that facilitate processing of the active compounds into preparations that can be used pharmaceutically. The administration modality will generally determine the nature of the carrier. For example, formulations for parenteral administration may comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solutions, or physiologically buffered saline. For tissue or cellular administration, penetrants appropriate to the particular barrier to be permeated are used in the formulation. Such penetrants are generally known in the art. For preparations comprising proteins, the formulation may include stabilizing materials, such as polyols (e.g., sucrose) and/or surfactants (e.g., nonionic surfactants), and the like.

Alternatively, formulations for parenteral use may comprise suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Emulsions, e.g., oil-in-water and water-in-oil dispersions, can also be used, optionally stabilized by an emulsifying agent or dispersant (surface-active materials; surfactants). Liposomes containing the active agent may also be employed for parenteral administration.

Alternatively, the pharmaceutical compositions comprising the agent in dosages suitable for oral administration can be formulated using pharmaceutically acceptable carriers well known in the art. The preparations formulated for oral administration may be in the form of tablets, pills, capsules, cachets, dragées, lozenges, liquids, gels, syrups, slurries, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragée cores. Note that oral formulations may employ liquid carriers similar in type to those described for parenteral use, e.g., buffered aqueous solutions, suspensions, and the like.

Preferred oral formulations include tablets, dragées, and gelatin capsules. These preparations may contain one or excipients, which include, without limitation:

a) diluents such as sugars, including lactose, dextrose, sucrose, mannitol, or sorbitol;

b) binders such as magnesium aluminum silicate, starch from corn, wheat, rice, potato, etc.;

c) cellulose materials such as methyl cellulose, hydroxypropylmethyl cellulose, and sodium carboxymethyl cellulose, polyvinyl pyrrolidone, gums such as gum arabic and gum tragacanth, and proteins such as gelatin and collagen;

d) disintegrating or solubilizing agents such as cross-linked polyvinyl pyrrolidone, starches, agar, alginic acid or a salt thereof such as sodium alginate, or effervescent compositions;

e) lubricants such as silica, talc, stearic acid or its magnesium or calcium salt, and polyethylene glycol;

f) flavorants, and sweeteners;

g) colorants or pigments, e.g., to identify the product or to characterize the quantity (dosage) of active compound; and h) other ingredients such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds may be dissolved or suspended in suitable fluids, such as fatty oils, liquid paraffin, or liquid polyethylene glycol with or without stabilizers.

Dragée cores can be provided with suitable coatings such as concentrated sugar solutions, which may also contain gum arabic, talc, polyvinyl pyrrolidone, carbopol gel, polyethylene glycol, and/or titanium dioxide, lacquer solutions, and suitable organic solvents or solvent mixtures.

The pharmaceutical composition may be provided as a salt of the active agent, which can be formed with many acids, including but not limited to hydrochloric, sulfuric, acetic, lactic, tartaric, malic, succinic, etc. Salts tend to be more soluble in aqueous or other protonic solvents that are the corresponding free base forms.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through pre-clinical in vitro and in vivo studies, later confirmed in humans during the course of clinical trials. Thus, for any compound used in the method of the invention, a therapeutically effective dose in mammals, particularly humans, can be estimated initially from biochemical and/or cell-based assays. Then, dosage can be formulated in animal models to achieve a desirable circulating concentration range that modulates pal expression or PAL activity. As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which is typically expressed as the ratio $LD_{50}/ED_{50}$. Compounds that exhibit large therapeutic indices are preferred. The data obtained from such cell culture assays and additional animal studies can be used in formulating a range of dosage for human use. The dosage of such compounds lies preferably within a range of circulating concentrations that include the $ED_{50}$ with little or no toxicity. Of course, similar studies can be conducted to ensure addition of PAL in either its polypeptide or polynucleotide-encoding form to microbial fermentation cultures can be carried out, e.g., to ensure optimal manufacture of L-phenylalanine (for instance, from ammonia and t-cinnamate), or production of phenylalanine analogs, and other optically active unnatural amino acids having phenylalanine-like structures.

For the method of the invention, any effective administration regimen regulating the timing and sequence of doses may be used. Doses of the agent preferably include pharmaceutical dosage units comprising an effective amount of the agent. As used herein, "effective amount" refers to an amount sufficient to provide or modulate pal expression or PAL activity and/or to derive a measurable change in a physiological parameter of the host cell or subject through administration of one or more of the pharmaceutical dosage units.

Exemplary dosage levels for a human subject are of the order of from about 0.001 milligram of active agent per kilogram body weight (mg/kg) to about 100 mg/kg. Typically, dosage units of the active agent comprise from about 0.01 mg to about 10,000 mg, preferably from about 0.1 mg to about 1,000 mg, depending upon the indication, route of administration, etc. Depending on the route of administration, a suitable dose may be calculated according to body weight, body surface area, or organ size. The final dosage regimen will be determined by the attending physician in view of good medical practice, considering various factors that modify the action of drugs, e.g., the agent's specific activity, the severity of the disease state, the responsiveness of the patient, the age, condition, body weight, sex, and diet of the patient, the severity of any infection, and the like. Additional factors that may be taken into account include time and frequency of administration, drug combination(s), reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in yeast clinical trials. Appropriate dosages may be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, may be preferred for continuous infusion.

Compositions comprising a compound of the invention formulated in a pharmaceutical acceptable carrier may be prepared, placed in an appropriate container, and labeled for treatment of an indicated condition. Conditions indicated on the label may include, but are not limited to, treatment and diagnosis of phenylketonuria. Kits are also contemplated, wherein the kit comprises a dosage form of a pharmaceutical composition and a package insert containing instructions for use of the composition in treatment of a medical condition.

EXAMPLES

The following examples further illustrate the present invention but, of course, should not be construed as in any way limiting its scope.

The examples presuppose an understanding of conventional methods well-known to those persons having ordinary skill in the art to which the examples pertain, e.g., the construction of vectors and plasmids, the insertion of genes encoding polypeptides into such vectors and plasmids, or the introduction of vectors and plasmids into host cells. Such methods are described in detail in numerous publications including, for example, Sambrook et al., *Molecular Cloning: A Laboratory Manual,* Cold Spring Harbor Laboratory Press (1989), Ausubel et al. (Eds.), *Current Protocols in Molecular Biology,* John Wiley & Sons, Inc. (1994); and Ausubel et al. (Eds.), *Short Protocols in Molecular Biology,* 4th ed., John Wiley & Sons, Inc. (1999).

Example 1

Obtaining a Polynucleotide that Encodes *Rhodotorula graminis* Phenylalanine Ammonia Lyase This example describes the isolation and sequencing of a phenylalanine ammonia lyase cDNA.

The mutant strain of the yeast *Rhodotorula graminis, strain (ATCC* 20804), has been shown to produce 4-to-5 fold higher levels of inducible phenylalanine ammonia lyase (PAL) (Omdorffet al., 1988; U.S. Pat. No. 4,757,015).

Cells of *R. graminis* strain ATCC 20804 were obtained from American Type Culture Collection (10801 University Boulevard, Manassas, Va. 20110–2209), and maintained in 20% glycerol in liquid nitrogen. About 3 mls of cells from cryostorage were used to inoculate a Fernbach flask containing 1 L of PAL Fernbach Medium. Cells were grown at 28° C. for 30 hours with shaking at about 250 rpm. This initial culture was used to inoculate 12 L of PAL Fermentation Medium, which was incubated at 28° C. (pH 6, 1 vvm air flow) with shaking at about 250 rpm for up to about 30 hours, with some aliquots removed at earlier times.

PAL Fernbach Medium comprises 10 g/L Amberex 695 yeast extract (e.g., Red Star Bioproducts, Juneau, Wis.), 52.5 ml/L HFCS High Fructose Corn Syrup, and 0.1 ml/L Mazur antifoam agent (e.g., made by PPG Industries Inc., Gurnee, Ill.). The pH of this medium was adjusted to 6.1 (e.g., with 45% KOH). PAL Fermentation Medium comprises 5 g/L Amberex 695 yeast extract, 2.0 g/L ammonium phosphate, 9.0 g/L L-phenylalanine, and 1.5 g/L L-isoleucine, 0.4 ml Mazur antifoam agent.

The PAL gene was cloned using RT-PCR (reverse transcriptase-polymerase chain reaction). In a first step, total RNA was isolated from exponentially growing cells of ATCC 20804 using the RNeasy kit from Qiagen Inc. (Valencia, Calif.), according to manufacturer's instructions. A cDNA preparation was made from the RNA with the GIBCO BRL (Rockville, Md., now Invitrogen, Carlsbad, Calif.) Superscript Preamplification kit. The cDNA was then amplified with touchdown PCR using degenerate primers (OLI 61, set forth as SEQ ID NO:1, and OLI 63, set forth as SEQ ID NO:2) designed from the *R. rubra* PAL amino acid sequence and the codon usage patterns of the *R. graminis* mandelate dehydrogenase genes.

Touchdown PCR parameters were as follows. There was one cycle at 94° C., 4 minutes. This was followed by 2 cycles each, decreasing by one degree with each two rounds of amplification as noted: 94° C., 30 seconds; 63° C.–51° C., 20 seconds; 72° C. 2.5 minutes. This was followed by 25 cycles each: 94° C., 30 seconds; 50° C., 20 seconds; 72° C., 2.5 minutes. The final cycle was at 72° C., 10 minutes.

A PCR fragment of the desired size (approximately 2.1 kilobases, the size corresponding to the PAL coding sequence of *R. rubra*) was isolated and cloned into the vector pBR322 and submitted for double stranded sequencing to Lark Technologies Inc. (Houston, Tex.).

The sequences of the specific ends of the *R. graminis* PAL gene were obtained using the DNA sequence determined above. Namely, the 5' end of the PAL gene was cloned, using the cDNA prepared above, with the GIBCO BRL (now Invitrogen, Carlsbad, Calif.) 5' RACE kit. The 3' end of the cDNA was tailed with dC nucleotides and then amplified with a forward primer AAP (set forth as SEQ ID NO:3), which hybridizes to the polyC tail, and a gene-specific reverse primer GSP2 (set forth as SEQ ID NO:4) designed from the *R. graminis* PAL DNA sequence. After another round of amplification with nested primers AUAP (set forth as SEQ ID NO:5) and GSP4 (set forth as SEQ ID NO:6), the fragment was cloned into the pCMV Sport-βgal vector and submitted to Lark Technologies, Inc. for sequencing. More specifically, for 5' RACE amplifications, for the amplification, there was 1 cycle at 94° C., 2 minutes. This was followed by 30 cycles: 94° C., 30 seconds; 57° C., 20 seconds; 72° C., 70 seconds. This was followed by one cycle at 72° C., 5 minutes.

The 3' end of the PAL gene was cloned using the 3' RACE kit from GIBCO BRL (now Invitrogen, Carlsbad, Calif.). First strand synthesis was performed using total RNA isolated from ATCC 20804 cells for the RT-PCR experiments. An oligo dT primer was employed that contains an adapter sequence AP (set forth as SEQ ID NO:7). The 3' end was amplified with a forward gene-specific primer (GSP5) (set forth as SEQ ID NO:8) and a reverse primer (AUAP) (set forth as SEQ ID NO:5). After another round of amplification using primers AUAP and GSP6 (set forth as SEQ ID NO:9), the fragment was cloned into pCMV Sport-βgal and submitted to Lark Technologies for sequencing. For 3' RACE amplifications, the same parameters were used as for the 5' RACE amplification.

Example 2

Comparing the *Rhodotorula graminis* Phenylalanine Ammonia Lyase Polypeptide and Polynucleotide Sequence With Those of Other Strains Other strains also can be employed in accordance with the invention to isolate PAL sequences. For instance, *R. graminis* strain KGX39 can be employed. This example accordingly describes the sequencing of the PAL cDNA of the parental *R. graminis* strain, KGX39.

The PAL gene of KGX39 was isolated in a manner similar to ATCC 20804, but rather than using the degenerate primers described in Example 1, specific primers (i.e., OLI 77 (set forth as SEQ ID NO:10) and OLI 78 (set forth as SEQ ID NO:11)) which correspond to sequences before and after the coding region of the ATCC 20804 PAL gene, were used to amplify PAL. The PAL fragment was cloned into the vector pBR322 and submitted to Lark Technologies for double-stranded sequencing. KGX39 PAL also was cloned using primers OLI 74 (set forth as SEQ ID NO:22) and OLI 75 (set forth as SEQ ID NO:23) which amplified just the coding region. These clones also were sequenced.

Based on the sequence information generated, the sequence of the coding region of KGX39 appears to be identical to that of ATCC 20804 with the possible exception of a single base change. Namely, as reflected in the sequences at SEQ ID NOS:12 and 13, the sequence obtained for ATCC 20804 contains a GTC at codon 153 (SEQ ID NO: 12 numbering), coding for Val, whereas the sequence obtained for KGX39 contains GCC, coding for Ala. In view of the sequence obtained for genomic clones, it appears more likely that residue 153 is Val, coded for by GTC. This suggests that any difference in PAL activity between ATCC 20804 and its parent may be due to a mutation in the genomic coding sequence (e.g., a regulatory mutation), or a difference in the polypeptides that interact with PAL.

Example 3

Comparing the *Rhodotorula graminis* Phenylalanine Ammonia Lyase Polypeptide and Polynucleotide Sequence With Those of Other Species Using the nucleotide sequence of ATCC 20804 PAL (set forth as SEQ ID NO: 12) determined as described above, a search of sequences of other species was performed. For certain of these comparisons, the search was done using the polypeptide sequence anticipated (set forth as SEQ ID NO:13) based on translation of the polynucleotide sequence.

Initially, the search for similar sequences was conducted with BLASTP (default parameters) using the *R. rubra* sequence, before the *R. graminis* sequence was known. The 28 sequences obtained showing the best homology were then analyzed using the PILEUP Multiple Sequence Alignment program (with Gap Weight: 12; Gap Length Weight: 4). After the *R. graminis* sequence was determined, it was added to the analysis.

Of these sequences uncovered, all 29 show homology in what is believed to be the active site. A visual inspection revealed strong and substantial differences between the sequences as compared to the PAL polypeptide (e.g., compare, for instance, the *Muscaria amanita* polynucleotide and polypeptide sequences at SEQ ID NOS:14 and 15, respectively), except for the yeast sequences Gi129592spp1024poly_Rhorb (*Rhodotorula rubra* PAL species) and Gi129593spp 11544paly_Rhoto (*Rhodosporidium toruloides* species), which appeared to have at least some similarity to the *R. graminis* PAL polypeptide.

The Clustal W program was then used to compare the *R. graminis* PAL polynucleotide and polypeptide sequence against the corresponding sequences in *R. toruloides* (i.e., GenBank Accession Number X51513) and *R. mucilaginosa* (i.e., GenBank Accession Number X13094 which formerly referred to *R. rubra* was updated as Accession Number X13095 to correspond to the re-classification of the strain as *Rhodotorula mucilaginosa,* and then was replaced by modified Accession Number X13094). In making these comparisons, only the exons of the sequences were included. The *R. toruloides* PAL counterpart sequences are set forth as SEQ ID NO:18 (polynucleotide) and SEQ ID NO:19 (polypeptide). The *R. rubra/mucilaginosa* PAL counterpart sequences are set forth as SEQ ID NO:16 (polynucleotide) and SEQ ID NO:17 (polypeptide).

A comparison of these sequences with those of *R. graminis* is depicted in FIGS. 1A–1B (polypeptide sequence) and in FIGS. 2A–2F (polynucleotide sequence). The sequences displayed 62.9% identity, and 90.2% similarity at the amino acid level (FIGS. 1A–1B). The sequences displayed 56% identity, and 86% similarity at the nucleic acid level (FIGS. 2A–2F). The overall consensus between the sequences are set out in the Figures, as well as in SEQ ID NO:20 (polynucleotide sequence) and SEQ ID NO:21 (polypeptide sequence).

Example 4

Isolation of the *Rhodotorula graminis* Phenylalanine Ammonia Lyase Polypeptide

For these studies, the yeast strain *Rhodotorula graminis,* ATCC 20804 was grown in a 20-liter *Biolafitte fermentor* using glucose-fed batch fermentation. The pH was maintained at 6.0 with use of 25% (v/v) $H_2SO_4$ or 10 N NaOH. The temperature was held at 28° C. for 18 hours, followed by rapid cooling to less than 10° C. The cells were removed and concentrated via ultrafiltration, and stored generally as frozen beads, prepared by dripping into liquid nitrogen. These growth and storage conditions allowed for maximum PAL activity.

The inoculum was prepared as described in Example 1. Fermentation was carried out by maintaining the culture under cell growth conditions (agitation is 500 rpm, and the air flow is 1 vvm (12 slpm) at 28° C.). When the initial glucose level falls to less than 1 g/L, then glucose is added back to 12 g/L (268g). When the glucose level again drops to less than 1 g/L, 500 ml of 25% Amberex 695 and isoleucine feed (1.0 g/L concentrations in fermentor) are added. After peak PAL activity is determined, the tank is sparged and the headspace is overlaid with nitrogen. The sparge is shut off once the tank is anaerobic, the rpm is lowered to 250, and the tank is cooled to less than 20° C. When the fermentor is less than 20° C., the cells are harvested via ultrafiltration.

PAL activity of ATCC 20804 was determined by adding 20 μl of PAL cells (6–15 mg/ml), 50 mM Tris buffer, pH 8.8) to 980 μl of a solution containing 50 mM Tris buffer (pH 8.8), 25 mM L-phenylalanine, and 0.001% (w/v) of cetylpyridinium chloride. The mixture was incubated at 30° C. in a spectrophotometer, and the appearance of cinnamate was followed at 280 nm (or the corresponding λmax for other substrates tested). The rate of increase in optical density was measured during a period of linear increase. The ratio of the change in optical density at 280 nm per minute to the optical density (660 nm) of the cells in the reaction mixture, was used as a means to determine "specific activity" of the PAL strain (αλmax/min)/(optical density, or "od", 660 nm). Activities of purified PAL fractions were determined by adding 50 μl of each fraction to 150 μl assay solution to each well in a 96-well microtiter plate. The plate was incubated at 30° C., and ΔA280 monitored with mixing between readings.

For enzyme purification, washed whole *R. graminis* cells were suspended in a 5× volume of 50 mM potassium phosphate buffer, pH 7.0, containing 25% (v/v) glycerol. The cells were disrupted using an M-110EH micofluidizer (Microfluidics, Newton, Mass.) at 25,000 psi. The crude lysate was centrifuged to remove cell debris and obtain the PAL-containing cell extract. The extract was brought to a 30% ammonium sulfate saturation, and the precipitate was removed by centrifugation. The supernatant was then brought to a 65% ammonium sulfate saturation, and the enzyme-containing precipitate was removed by centrifugation. The pellet was resuspended in 50 mM Tris buffer (pH 8.5) containing about 25% (v/v) glycerol (buffer A). This was designated the ammonium sulfate ("AS") fraction. The AS fraction was loaded onto an XK50 column (Pharmacia, Peapack, N.J.) packed with 150 ml phenyl Sepharose HP (Pharmacia, Peapack, N.J.) equilibrated in 50 mM potassium phosphate buffer (pH 7.0) containing 1.7 ammonium sulfate and 10% (v/v) glycerol (buffer A). The column was eluted using a reverse linear gradient from 1.7–0 M ammonium sulfate (buffer B). The enzyme eluted at an ammonium sulfate concentration of approximately 170 mM, so the gradient was adjusted to 0.34 to 0 M ammonium sulfate, with the initial equilibration at 80% buffer B. The active fractions were pooled and designated the HIC fraction. The HIC fraction was brought to an 85% ammonium sulfate concentration, and the precipitated protein containing 95% of the activity was stored as a frozen pellet. The pellet was resuspended in a 25 mM potassium phosphate buffer pH 7.0 containing 10% (v/v) glycerol, and dialyzed against 50 mM potassium phosphate, pH 7.0. Next, the concentrated/dialyzed HIC fraction was run on a AX1000 weak anion exchange column, 250×21.4 mm (SynChrom, Linden Ind.), using a 0.05–0.5M potassium phosphate (pH 7.0) gradient containing 10% (v/v) glycerol. The active fractions eluted at a conductivity of approximately 25 mS/cm, and were pooled and designated the AX fraction. The AX fraction was brought to an 85% ammonium sulfate concentration, and the precipitated protein containing 95% of the activity was stored as a frozen pellet. The enzyme was judged to be approximately 75% pure by SDS-PAGE analysis.

Protein was determined by the method of Bradford assay, using bovine serum albumin as a standard.

Example 5

Construction of pY141

This example describes the construction of plasmid pY141, which comprises the polynucleotide sequence of SEQ ID NO:12, and which encodes the sequence of SEQ ID NO:13. The PAL fragment was amplified from the cloned PAL described in Example 1 using primers OLI 105 (set forth as SEQ ID NO:24) and OLI 80 (set forth as SEQ ID NO:25) and the Clontech Advantage-HF PCR kit (Clontech Laboratories, Inc., Palo Alto, Calif.) according to manufacturer's directions. Touchdown PCR parameters were used as follows: One cycle each, decreasing by one degree with each round of amplification as noted: 94° C., 30 seconds; 70–62° C., 20 seconds; 72° C., 1 minute. This was followed by 20 cycles each: 94° C., 30 seconds; 61° C., 20 seconds; 72° C., 1 minute. The final cycle was at 72° C., 5 minutes. A PCR fragment of the desired size (approximately 2.1 kilobases) was isolated and ligated to the large EcoRI/SphI fragment of vector pBR322, resulting in plasmid pY141.

Plasmid pY141 was introduced into the host cell *E. coli* XL1-Blue, and the resultant strain RY624 was deposited with ATCC (American Type Culture Collection), 10801 University Boulevard, Manassas, Va. 20110–2209, on Jul. 12, 2000 as strain PTA-2224.

Example 6 pal Gene Sequence

This example described the isolation and sequencing of *R. graminis* phenylalanine ammonia lyase genomic DNA. The pal gene was isolated from wild-type strain KGX 39 and mutant strain ATCC 20804.

The genomic clones were prepared by amplification of the appropriate chromosomal DNA with oligonucleotides OLI 89 (SEQ ID NO:26) and OLI 90 (SEQ ID NO:27). Chromosomal DNA was prepared using the Qiagen Genomic DNA Buffer Kit, following the manufacturer's protocol for yeast DNA isolation. For the genomic KGX39 PAL clone, the Clontech Advantage HF PCR kit was used with the following touchdown PCR parameters. There was one cycle at 95° C., 1 minute. This was followed by 1 cycle each, decreasing by one degree with each round of amplification as noted: 94° C., 30 seconds; 68° C. –61° C., 20 seconds; 72° C., 1 minute. This was followed by 20 cycles: 94° C., 30 seconds; 60° C., 20 seconds; 72° C., 1 minute. The final cycle was 72° C., 5 minutes. The PCR fragment was isolated and cloned into a pBR322-based vector (i.e., for convenience, pPOT5 constructed at NSC Technologies, Mount Prospect, Ill., although any pBR322-based vector conceivably could be employed). The PCR fragment was submitted for double stranded sequencing to ACGT, Inc. (Northbrook, Ill.).

For the genomic ATCC 20804 PAL clone, the Stratagene Pfu DNA polymerase kit was used with the following PCR parameters. There was one cycle at 95° C., 1 minute. This was followed by 25 cycles: 94° C., 35 seconds; 68° C., 35 seconds, 75° C., 4 minutes. The final cycle was 72° C., 5 minutes. The PCR fragment was isolated and cloned into a pBR322-based vector (pPOT5) and sequenced by ACGT, Inc. (Northbrook, Ill.).

Example 7

Sequence of the *Rhodotorula graminis* Phenylalanine Ammonia Lyase Gene

This example describes the *R. graminis* PAL genomic sequence.

Based on the sequence information generated (set forth as SEQ ID NO:28), the PAL gene isolated for both KGX39 (FIG. 4) and ATCC 20804 (FIG. 3) appears to be identical except that the sequence obtained for ATCC 20804 contains a GCC at codon 2 (SEQ ID NO:12 numbering), coding for Ala, whereas the sequence obtained for KGX39 contains GCA, which also codes for Ala. This discrepancy between the genomic sequences obtained, and the discrepancy in the cDNA sequences obtained (already discussed) creates a lack of identity in the cDNA and genomic sequences at codons 2 and 153. A further difference between the cDNA and genomic sequences is observed at nucleotide 2688 in SEQ ID NO:28, i.e., a T, whereas the corresponding position in SEQ ID NO:12, nucleotide 2298, is a C. This difference in noncoding DNA, like the other aforementioned differences, could be the result of a sequencing error. More important, as compared with the cDNA sequences, the coding region of the genomic sequences (as described in SEQ ID NO:28) is interrupted by the presence of introns at residues 362 to 448, 881 to 960, 1296 to 1364, 1530 to 1586, 1749 to 1821, and 1948 to 2007 (SEQ ID NO:28 numbering).

All of the references cited herein, and particularly U.S. Ser. No. 09/624,693 filed Jul. 24, 2000, and PCT International Application PCT/US01/23270 filed Jul. 24, 2001, are hereby incorporated in their entireties by reference for all that they disclose.

While this invention has been described with an emphasis upon certain preferred embodiments, it will be obvious to those of ordinary skill in the art that variations in the preferred embodiments may be used, and that it is intended that the invention may be practiced otherwise than as specifically described herein. Accordingly, this invention includes all modifications encompassed within the spirit and scope of the invention as defined by the following claims.

What is claimed is:

1. An isolated and purified polynucleotide that encodes a yeast phenylalanine ammonia lyase polypeptide comprising the sequence of SEQ ID NO:13.

2. An isolated and purified polynucleotide that encodes a yeast phenylalanine ammonia lyase polypeptide comprising the sequence of SEQ ID NO:21.

3. An isolated and purified yeast phenylalanine ammonia lyase polynucleotide comprising the sequence of SEQ ID NO:20.

4. An isolated and purified yeast phenylalanine ammonia lyase polynucleotide comprising the sequence of SEQ ID NO:20, wherein nucleotides 117, 135, 190, 191, 195, 276, 1196 to 1198, 1724 to 1735, 1880, 1881, and 2187 to 2475 are absent, nucleotides 13, 34, 46, 115, 164, 251, 266, 315, 330, 333, 340, 348, 423, 450, 456, 468, 555, 570, 675, 681, 716, 723, 783, 921, 1176, 1380, 1383, 1407, 1446, 1449, 1452, 1488, 1542, 1554, 1563, 1617, 1677, 1683, 1776, 1872, 1895, 1950, 1971, and 1976 are B, nucleotides 49, 119, 331, 463, 715, 1270, 1684, 1708, 1762, 1768, 2001, 2145, and 2183 are D, nucleotides 59, 73, 102, 145, 233, 264, 357, 483, 758, 1042, 1241, 1470, 1509, 1690, 1745, 1962, and 2151 are H, nucleotides 51, 57, 144, 168, 201, 312, 405, 475, 963, 1043, 1281, 1308, 1675, 1678, 1681, 1693, 1952, and 2146 are V, nucleotides 79, 729, 1710, and 1873 are Y, nucleotides 84, 199, and 1723 are W, nucleotides 82, 200, 732, and 744 are S, nucleotides 106, 108, 284, and 743 are M, nucleotides 730 is K, nucleotides 76 and 77 are A, nucleotides 68, 75, 1855, 1857, 1858, 1860, 1862, and 1874 are C, and nucleotides 69, 1856, 1859, 1861, 1875 are T.

5. An isolated and purified polynucleotide encoding a yeast phenylalanine ammonia lyase polypeptide that comprises the sequence of SEQ ID NO:13 but is N-terminally truncated by the absence of one or more of amino acids 1 through 6 of SEQ ID NO: 13.

6. An isolated and purified polynucleotide encoding a yeast phenylalanine ammonia lyase polypeptide that comprises the sequence of SEQ ID NO:13 but is C-terminally truncated by the absence of one or more of amino acids 715 through 720 of SEQ ID NO: 13.

7. An isolated and purified yeast phenylalanine ammonia lyase polynucleotide comprising nucleotides 37 to 2196 of SEQ ID NO:12.

8. An isolated and purified yeast polynucleotide that encodes phenylalanine ammonia lyase and specifically hybridizes under high stringency conditions to nucleotides 37 to 2196 of SEQ ID NO:12, and said high stringency conditions comprise hybridization in 50% formamide, 5×SSC, at 42° C. overnight, and washing in 0.5×SSC and 0.1% SDS, at 50° C.

9. A construct that comprises a phenylalanine ammonia lyase polynucleotide according to claim 1.

10. A host cell that comprises the construct of claim 9.

11. A construct that comprises a phenylalanine ammonia lyase polynucleotide according to claim 7.

12. A host cell that comprises the construct of claim 11.

13. A method of obtaining an isolated and purified phenylalanine ammonia lyase polypeptide, said method comprising the steps of:

(a) growing the host cell according to claim 10 under conditions where the polypeptide is produced; and (b) isolating the polypeptide from the host cell or the medium in which the host cell is grown.

* * * * *

UNITED STATES PATENT AND TRADEMARK OFFICE
CERTIFICATE OF CORRECTION

PATENT NO. : 6,967,097 B2
APPLICATION NO. : 09/939408
DATED : November 22, 2005
INVENTOR(S) : Roberta K. Yoshida et al.

It is certified that error appears in the above-identified patent and that said Letters Patent is hereby corrected as shown below:

On The Title Page Item (54):

At line (54), "PHENYLALAININE" should be -- PHENYLALANINE --.

At line (73), "PCBU Services, Inc., Wilmington, DE (US)" should be -- Excelsyn Molecular Development Limited, Holywell (GB) --.

At Column 1, line 1, "PHENYLALAININE" should be -- PHENYLALANINE --.

Signed and Sealed this

Fourth Day of September, 2007

JON W. DUDAS
*Director of the United States Patent and Trademark Office*